United States Patent
Sørum

(10) Patent No.: US 12,403,187 B2
(45) Date of Patent: Sep. 2, 2025

(54) BACTERIAL VACCINE

(71) Applicant: BELLEVACC AS, Ås (NO)

(72) Inventor: Henning Sørum, Oslo (NO)

(73) Assignee: BELLEVACC AS, Ås (NO)

( * ) Notice: Subject to any disclaimer, the term of this patent is extended or adjusted under 35 U.S.C. 154(b) by 262 days.

(21) Appl. No.: 17/419,855

(22) PCT Filed: Dec. 20, 2019

(86) PCT No.: PCT/EP2019/086639
§ 371 (c)(1),
(2) Date: Jun. 30, 2021

(87) PCT Pub. No.: WO2020/141103
PCT Pub. Date: Jul. 9, 2020

(65) Prior Publication Data
US 2022/0072116 A1  Mar. 10, 2022

(30) Foreign Application Priority Data

Dec. 31, 2018 (NO) .................................. 20181683

(51) Int. Cl.
*A61K 39/085* (2006.01)
*A61K 39/02* (2006.01)
(Continued)

(52) U.S. Cl.
CPC ........ *A61K 39/085* (2013.01); *A61K 39/0208* (2013.01); *A61K 39/092* (2013.01); *A61K 39/107* (2013.01); *A61P 31/04* (2018.01)

(58) Field of Classification Search
CPC .............. A61K 39/085; A61K 39/0208; A61K 39/092; A61K 39/107; A61K 2039/521;
(Continued)

(56) References Cited

U.S. PATENT DOCUMENTS

2007/0020291 A1  1/2007  Bethke et al.
2015/0132341 A1  5/2015  Sorum
(Continued)

FOREIGN PATENT DOCUMENTS

KR       101610914 B1    4/2016
KR    20180106570 A    10/2018
(Continued)

OTHER PUBLICATIONS

Domingue, Gerald J. "Demystifying pleomorphic forms in persistence and expression of disease: Are they bacteria, and is peptidoglycan the solution?" Discovery medicine (2010), 9 pages.
(Continued)

*Primary Examiner* — Jana A Hines
(74) *Attorney, Agent, or Firm* — Meunier Carlin & Curfman LLC

(57) ABSTRACT

The present document discloses a method for producing a bacterial vaccine composition against bacterial diseases in animals, such as tetrapods or fish, wherein said bacterial vaccine composition comprises inactivated bacteria of the bacterium causing said bacterial diseases. The method involves exposing the bacteria to different growth conditions and then preparing a bacterial vaccine composition where the bacteria are exposed to different growth conditions. With vaccines prepared by the present method, bacterial diseases that previously had not been able to be cured could be treated or the effect of the treatment was more long-lasting.

16 Claims, 11 Drawing Sheets

(51) Int. Cl.
A61K 39/09 (2006.01)
A61P 31/04 (2006.01)

(58) Field of Classification Search
CPC .... A61K 2039/552; A61K 2039/55566; A61K 2039/55583; A61K 2039/70; A61P 31/04
See application file for complete search history.

(56) References Cited

U.S. PATENT DOCUMENTS

2016/0296614 A1 10/2016 Sørum
2018/0193441 A1 7/2018 Rubio Nistal et al.

FOREIGN PATENT DOCUMENTS

| RU | 2016144119 A | 5/2018 | |
| WO | 9611258 A1 | 4/1996 | |
| WO | 9612734 A1 | 5/1996 | |
| WO | 0240515 A2 | 5/2002 | |
| WO | 2005112993 A1 | 12/2005 | |
| WO | 2007068058 A1 | 6/2007 | |
| WO | WO-2013010260 A1 * | 1/2013 | ............. C07K 14/20 |
| WO | WO-2013171236 A1 * | 11/2013 | ......... A61K 39/0208 |
| WO | 2015074946 A1 | 5/2015 | |
| WO | 2018007632 A1 | 1/2018 | |

OTHER PUBLICATIONS

Gudding, R. & Van Muiswinkel, W. B. (2013). A history of fish vaccination: science-based disease prevention in aquaculture. Fish & shellfish immunology, 35(6), 1683-1688.
Roberts, N. et al. (2014). Intratumoral injection of Clostridium novyi-NT spores induces antitumor responses. Science translational medicine, 6(249), 249ra111-249ra111.
Lavy, A., Keren, R., Haber, M., Schwartz, I., & Ilan, M. (2014). Implementing sponge physiological and genomic information to enhance the diversity of its culturable associated bacteria. FEMS microbiology ecology, 87(2), 486-502.
Rouf, A., Kanojia, V., Naik, H. R., Naseer, B., & Qadri, T. (2017). An overview of microbial cell culture. Journal of Pharmacognosy and Phytochemistry, 6(6), 1923-1928.
Sommerset, I., Krossøy, B., Biering, E., & Frost, P. (2005). Vaccines for fish in aquaculture. Expert review of vaccines, 4(1), 89-101.
International Search Report and Written Opinion mailed Apr. 2, 2020 in PCT/EP2019/086639 (11 pages).
Hjerde E, Karlsen C, Scrum H, Parkhill J, Willassen NP, Thomson NR. Co-cultivation and transcriptome sequencing of two co-existing fish pathogens Moritella viscosa and Aliivibrio wodanis. BMC Genomics. Jun. 10, 2015; 16:447.
Angelidis P. et al. "Efficacy of a *Listonella anguillarum* (syn. vibrio anguillarum) vaccine for juvenile sea bass *Dicentrarchus labrax*", Dis Aquat Organ (2006) 71:19-24.
Johnson KA. et al. "Duration of immunity in salmonids vaccinated by direct immersion with yersinia ruckeri and vibrio anguillarum bacterins", J Fish Dis (1982) 5:207-13.
Schrøder MB. et al. "Two serotypes of vibrio salmonicida isolated from diseased cod (*Gadus morhua* l.); virulence, immunological studies and vaccination experiments", Fish Shellfish Immunol (1992)2:211-21.
Liu X. et al. "Efficacy of chitosan oligosaccharide as aquatic adjuvant administrated with a formalin-inactivated vibrio anguillarum vaccine", Fish Shellfish Immunol (2015) 47:855-60.
Nguyen HT. et al, A formalin-inactivated vaccine provides good protection against vibrio harveyi infection in orange-spotted grouper (*Epinephelus coioides*). Fish Shellfish Immunol (2017) 65:118-26.
Cao J. et al. "Construction of vibrio mimicus ghosts as a novel inactivated vaccine candidate and its protective efficacy against ascites disease in grass carps (*Ctenopharyngodon idella*)", Aquaculture (2018) 485:147-53.
Cao J. et al, "Identification of fish source vibrio alginolyticus and evaluation of its bacterial ghosts vaccine immune effects", Microbiologyopen (2018).
Jeong Yu et al. "Protective efficiency of an inactivated vaccine against streptococcus iniae in olive flounder, paralichthys olivaceus" Arch Polish Fish (2016) 24:23-32.
Du et al. "Current status and development prospects of aquatic vaccines," Front. Immunol. 13:1040336. doi: 10.3389/fimmu.2022.1040336. Nov. 10, 2022.

* cited by examiner

| Groups | Ulcer scoring | | | | |
| --- | --- | --- | --- | --- | --- |
| | 3 | 0 | 1 | 2 | Total |
| Elanco Pentium Forte Plus | 6 | 35 | 52 | 3 | 96 |
| IMM A | 29 | 15 | 42 | 9 | 95 |
| IMMB | 30 | 10 | 46 | 8 | 94 |
| IP A | 16 | 18 | 47 | 6 | 87 |
| IP B | 23 | 21 | 44 | 8 | 96 |
| IP C | 24 | 22 | 46 | 3 | 95 |
| IP D | 21 | 22 | 44 | 9 | 96 |
| Saline | 25 | 16 | 47 | 6 | 94 |
| Totalsum | 174 | 159 | 368 | 52 | 753 |

BACTERIAL VACCINE

TECHNICAL FIELD

The present disclosure concerns a method for producing a bacterial vaccine composition against bacterial diseases in animals, such as fish or tetrapods, such as mammals.

BACKGROUND OF THE DISCLOSURE

Certain bacterial pathogens are able to evade the host immune system of an animal and cause acute or chronic infections. While acute bacterial infections often can be treated by antibiotics, the eradication of chronic infections is difficult. A chronic infection is characterized by a bacterial population that escapes the immune system and commonly the effects of antibiotics. It is verified that many pathogenic bacteria are able to produce capsules or other surface antigens that confuse the immune system resulting in inefficient protection against the infection. In chronic infections, the pathogenic bacteria have a lower multiplication rate, and they are not easily killed or inhibited by antibiotics as many antibiotics require metabolic activity to exert their action.

It is thus challenging to treat chronic bacterial infections in all animals, including vertebrates, and the available treatments often include very long-term treatment with antibiotics. The difficulty applies to tetrapods, such as mammals, including humans, birds and amphibia alike, and to fish, including teleostei.

Animal health, for both tetrapods and fish, is crucial for livestock and pet species. For instance, fish farming involves raising fish, such as salmonids, carp, tilapia, and catfish in tanks, net pens or other enclosures. The farmed fish are often contained at high densities, which increases the risk for infections by, e.g. parasites such as fish lice, intestinal worms, fungi, virus and bacteria. In order to control such infections, the fish farming industry often relies on the use of antibiotics and chemical control agents, which is undesirable, e.g. due to the spread of these toxic agents to the environment and the fear for development of bacterial antibiotic resistance in the society.

A common problem to farmed fish is bacteria that cause wounds and ulcers in the skin of the fish which both reduce the animal welfare and later the quality of the slaughtered fish because of scar tissue. The ulcer bacteria also cause septicemia that increases the percentage of fish that die because of the infection. Examples of bacteria which have been associated with such diseases are *Moritella viscosa, Bizionia piscinecroseptica, Aliivibrio friggiae, Tenacibaculum dicentrarchi* and *Aliivibrio wodanis*. Acute bacterial infections in farmed fish that develop into outbreaks with high loss in the population in a limited time create a high concentration of bacterial pathogens that cause the effective spread of the infection between the individuals in the population. Some of the fish pathogens causing epidemic outbreaks are *Aliivibrio salmonicida, Aeromonas salmonicida, Vibrio anguillarum, Edwardsiella piscicida*, and *Aeromonas hydrophila*. The ports of infection for bacterial pathogens are not well studied, but both the gills, the intestine and the skin are considered important.

Mammals like dogs, cows, sheep, horses and humans suffer from many clinical variants of bacterial infections, as do poultry. Staphylococcal skin infections are common in dogs and may vary from superficial to deep infections often at several predilection areas like the skin around the mouth and on the feet in addition to the skin covering the ventral side of the dog. The staphylococcal infections lead to chronic changes in the skin and the subcutaneous tissues including abscessa, pustules and thickened skin with a high degree of itching and discomfort for periods of months and years. Often are these dogs affected by staphylococcal infections in both ears in addition to the skin infections.

It is observed that dogs of certain dog breeds have a higher frequency of chronic skin infections caused by *Staphylococcus pseudintermedius* than others, which may indicate some weakness in the immune system unabling the dog to control the staphylococci in the skin.

The staphylococcal skin infections in dogs are difficult to treat. The most effective treatment so far are long antibiotic cures with cephalexin for 3 to 5 weeks. The effect comes relatively slow, and after 3-4 weeks the symptoms are improved. However, when the antibiotic cure is terminated the symptoms return after a couple of weeks, and the condition needs repetitive antibiotic treatments during the year, and the infection may continue for several years, often the rest of the life of the dog. Dogs that are affected are normally not going to be cured permanently and many dog owners become tired and worn out by using various topical treatments that only superficially control the skin infection. The dogs suffer from itching and the secondary inflammations of licking and scratching. The behaviour of the affected dogs is to a large extent a result of the symptoms of the skin infection. The most severe cases of dogs with deep chronic furunculosis are often euthanized after some years of suffering and hard work by the owner.

The use of cephalexins in treating furunculosis in dogs is the major cause of development of antibiotic resistance in *S. pseudintermedius*. In recent years, the spread of methicillin resistant *S. pseudintermedius* (MRSP) has increased in the dog population most probably as a result of the use of cephalexin to control skin infections in dogs. This phenomenon resembles the situation in human medicine where methicillin resistant *Staphylococcus aureus* (MRSA) is an emerging problem in most countries.

In veterinary medicine, skin infections caused by staphylococci are the diseases that result in the highest consumption of critically important antibiotics also for use in human medicine, and it is highly important to reduce the consumption of antibiotics to these dogs to reduce the frequency in development of antibiotic resistance in staphylococci.

Vaccination has been used or proposed as a means for treating and/or preventing bacterial infections. Antibiotic treatment of outbreaks of acute bacterial infections is used in most countries. Routinely use of antibiotics often causes antibiotic resistant bacterial pathogens.

Due to the problems discussed above among others, fish farming industries often face a high loss of the farmed fish with negative economic consequences for the fish farmer. Thus, increasing the survival of the fish and increasing the net output in relation to the amount of feed used is highly desirable. The focus on reducing antibiotic use in husbandry and all parts of medicine is high. Animal owners, veterinarians, human doctors, national and international regulatory bodies as well as WHO and FAO are very much concerned about the development of antibiotic resistance, and the phenomenon is among the top priorities globally. To date, vaccines against bacterial infections in all animals are not highly effective in particular against chronic infections, or they may vary in their effect from batch to batch leaving the vaccines containing bacterial inactivated toxins the most effective in the prevention of disease and harm from bacterial infections. This situation has led to an overuse of antibiotics.

An objective of the present disclosure is to overcome or at least mitigate some of the problems associated with the prior art.

SUMMARY OF DISCLOSURE

The present document is directed to a method for producing a bacterial vaccine composition against a bacterial disease in an animal, such as a tetrapod and/or a fish, wherein said bacterial vaccine composition comprises inactivated bacteria of the bacterium causing said bacterial disease, said method comprising preparing one or more of cultures A to H by:

i) preparing a culture A by first preparing a pre-culture a. by inoculating said bacterium in 0.5 to 3.5%, such as 0.9% NaCl, and incubating before transferring said pre-culture a. to a nutrient-rich bacterial growth medium, such as Luria broth with 0.5% to 3.5%, such as 0.9% NaCl, and incubating under microaerophilic conditions to prepare culture A;

ii) preparing a culture B by first preparing a pre-culture a. by inoculating said bacterium in 0.5 to 3.5%, such as 0.9% NaCl and incubating before transferring said pre-culture a. to cell culture medium for fish or mammalian cells, such as RPMI medium 1640, DMEM+GlutaMAX®, AIM-V+AlbuMAx®, or Leibowitz medium, and incubating under microaerophilic conditions to prepare culture B;

iii) preparing a culture C by first preparing a pre-culture b. by inoculating said bacterium in a cell culture medium for fish or mammalian cells, such as RPMI medium 1640, DMEM+GlutaMAX, AIM-V+AlbuMAx, or Leibowitz medium, and incubating before transferring said pre-culture b. to a solution typically comprising about 0.5 to 15% (w/v) gelatin, such as 3.2% (w/v), with 0.05 to 1.5% glucose, such as 1% glucose, such as in a ratio of ¼ of culture b. to the gelatin/glucose solution and incubating under microaerophilic conditions to prepare culture C;

iv) preparing a culture D by first preparing a pre-culture c. by inoculating said bacterium in blood, plasma or serum, e.g. from horses, and incubating before transferring said pre-culture c. to brain heart infusion medium with 0.05 to 1.5% glucose, such as 1% glucose, such as in a ratio of ¼ of culture c. to brain heart infusion medium and incubating under microaerophilic conditions to prepare culture D;

v) preparing a culture E by inoculation said bacterium in enrichment broth and incubating under aerobic conditions to prepare culture E;

vi) preparing a culture F by transferring bacteria from culture E or from enrichment medium containing for example blood, plasma and/or serum to 0.5 to 3.5% NaCl, such as 0.9% NaCl;

vii) preparing a culture G by transferring bacteria from culture E or from enrichment medium containing for example blood, plasma and/or serum, to a cell culture medium for fish or mammalian cells, such as RPMI medium 1640, DMEM+GlutaMAX, AIM-V+AlbuMAX, or Leibowitz medium;

viii) preparing a culture H by transferring bacteria from culture E or from enrichment medium containing for example blood, plasma and/or serum to blood or plasma serum, e.g. from horses;

ix) inactivating the bacteria of cultures A-H;

x) optionally washing the inactivated cultures of step ix), such as in phosphate buffered saline (PBS); and xi) if more than one culture is prepared, mixing the optionally washed and resuspended inactivated cultures to prepare the bacterial vaccine composition;

wherein step xi) of mixing optionally may be performed before step ix) or before step x) instead of after step x);

with the proviso that if culture E is prepared, then at least one of cultures A-D or F-H is also prepared.

Step ix) may be performed directly following step viii).

The bacterial disease may be a co-infection.

The method may comprise preparing two or more of the cultures A-H.

The method may comprise preparing three or more of the cultures A-H, such as three, four, five, six, seven, or eight of the cultures A-H.

One of the cultures in the bacterial vaccine composition prepared may be culture A.

One of the cultures in the bacterial vaccine composition prepared may be culture D.

One of the cultures in the bacterial vaccine composition prepared may be culture B.

One of the cultures in the bacterial vaccine composition prepared may be culture C.

When one of the cultures in the bacterial vaccine composition prepared is culture E at least one of cultures A-D or F-H is also prepared.

One of the cultures in the bacterial vaccine composition prepared may be culture F.

One of the cultures in the bacterial vaccine composition prepared may be culture G.

One of the cultures in the bacterial vaccine composition prepared may be culture H.

The method may comprise preparing all of cultures A-H.

The cultures of the bacterial vaccine composition may comprise or consist of cultures E, F, and H.

The cultures of the bacterial vaccine composition may comprise or consist of cultures A, B, C, G, and H.

The cultures of the bacterial vaccine composition may comprise or consist of cultures B, C, E, G, and H.

The cultures of the bacterial vaccine composition may comprise or consist of cultures A, B, C, F, and G.

The cultures of the bacterial vaccine composition may comprise or consist of cultures A, B, C, E, and H.

The cultures of the bacterial vaccine composition may comprise or consist of cultures B, C, E, G, and H.

The cultures of the bacterial vaccine composition may comprise or consist of cultures A, B, D, E, G, and H.

The cultures of the bacterial vaccine composition may comprise or consist of cultures A, B, C, D, and G.

The ratio of cultures A-H may be:

| Culture | Relative % |
| --- | --- |
| A | 8.6% |
| B | 8.6% |
| C | 8.6% |
| D | 8.6% |
| E | 40% |
| F | 8.6% |
| G | 8.6% |
| H | 8.6% |

The ratio of cultures A-H may be:

| Culture | Relative % |
| --- | --- |
| A | 10% |
| B | 10% |

-continued

| Culture | Relative % |
|---------|-----------|
| C | 10% |
| D | 15% |
| E | 40% |
| F | 5% |
| G | 5% |
| H | 5% |

The cell-culture medium for fish or mammalian cell may be Leibowitz medium.

The method may include a step of mixing the bacterial vaccine composition obtained in said method with an adjuvant, such as Freunds Incomplete Adjuvant (FICA) and Curdlan. The FICA and Curdlan may be present in a ratio of 40% to 60%, 50% to 50% or 60% to 40%.

The bacterium may be selected from the group consisting of *Staphylococcus pseudintermedius, Aeromonas salmonicida, Tenacibaculum dicentrarchi, Moritella viscosa, Aliivibrio wodanis. Vibrio anguillarum, Aliivibrio salmonicida, Aliivibrio friggiae, Bizionia piscinecroseptica, Aliivibrio hodis, Aliivibrio heliae, Photobacterium pisciinfectiosa, Staphylococcus aureus, Streptococcus equi.*

The animal may be a tetrapod, such as a mammal, bird or amphibia alike.

The mammal may be a dog, a cat, a horse, a cow, a sheep, a goat, a pig, or a human.

The bird may be a chicken, a hen or a turkey.

The fish may be a teleost, such as salmon, sea bass, or trout.

The present document is also directed to a bacterial vaccine composition obtainable or obtained by the herein disclosed method.

The present document is also directed a bacterial vaccine composition as disclosed herein for use in the treatment and/or prevention of a bacterial disease caused by said bacterium in said bacterial vaccine composition. The present document is also directed to the use of a bacterial vaccine composition as disclosed herein for the manufacture of a vaccine for the treatment and/or prevention of bacterial diseases caused by said bacterium in said bacterial vaccine composition. The present document is also directed to a method for treating or preventing a bacterial infection, said method comprising administering a pharmaceutically effective amount of a bacterial vaccine composition as disclosed herein to a subject in need thereof.

The bacterial disease may e.g. be an infection caused by *Staphylococcus pseudintermedius*, such as a skin infection, such as deep furunculosis or superficial impetigo and/or ear infection. The bacterial disease may also be winter ulcer, ulcer rot, fin rot, vibriosis, cold-water vibriosis or furunculosis.

The bacterial vaccine composition may be administered via bath vaccination, dip vaccination, intraperitoneally, subcutaneously, topically and/or by oral vaccination.

Other features and advantages of the disclosure will be apparent from the following detailed description, drawings, examples, and from the claims.

Definitions

The term "bacterial disease" in the context of the present document may be a bacterial disease caused by one type (such as a species or strain) of a bacterium or a disease caused by two or more bacterial species, such as a co-infection caused by two or more bacterial species. The "bacterial disease" may in this context also refer to two or more separate bacterial diseases.

The term "bacterium causing said bacterial disease", such as in the term "bacterial vaccine composition comprises inactivated bacteria of the bacterium causing said bacterial disease", is in the context of the present document intended to include bacteria of one strain or species, and a combination of two or more bacteria causing the same (such as a co-infection caused by two or more different bacterial species) or different diseases.

The term "gelatin" is in the context of the present document intended to include all forms of collagen, including type 1 collagen and type 2 collagen. Gelatin is an irreversibly hydrolyzed form of collagen, wherein the hydrolysis results in the reduction of protein fibrils into smaller peptides, which will have broad molecular weight ranges associated with physical and chemical methods of denaturation, based on the process of hydrolysis. This is the form of collagen that is readily available for industrial use and for vaccine production. Further, the term "gelatin" in the context of the present document include gelatin-related proteins, such as fibrin or any other components of the connective tissue that is produced by connective tissue cells as polymer proteins, typically by fibrocytes or fibroblasts that can produce various forms of connective tissue proteins. All variants of these can be used, alone or in combination according to the present document. For example, gelatin may be used.

The term "salt" and the chemical formula NaCl, sodium chloride, is used in a broad sense, covering natural occurring salt, comprising chloride ions, such as calcium, potassium, and magnesium salts of chloride present in sea and mineral salt. Thus, when a range is disclosed as for example 5 to 35 g NaCl, then the term "NaCl" could comprise these other salts.

Cumulative mortality in V-3445 after cohabitation challenge with *Aeromonas salmonicida* ss *salmonicida* for 47 days. 96 shedders challenged by ip-injection of *A. salmonicida* ss *salmonicida*. G10 are challenged by ip-injection of saline. G1 has no *A. salmonicida* ss *salmonicida* bactrin and had only 23 fish while G2 had 1.5%, G3 had 3%, G4 had 5%, G5 had 10%, G6 had 15%, G7 had 20% and G8 had 25% *A. salmonicida* ss *salmonicida* bactrin and G9 was vaccinated with a registered and marketed vaccine for Atlantic salmon with 18% bactrin from *A. salmonicida* ss *salmonicida* and with 50% mineral oil. The test vaccines G1 to G8 contained 20% mineral oil.

FIG. 2

Cumulative mortality of Cumulative mortality in V-3559 after a bath challenge with *Moritella viscosa* at day 0. All eight groups are hosted in the same tank. IMM A and IMM B are immersion vaccinated in a 1:10 dilution of the water based bacterins while IP A, IP B, IP C and IP D are intraperitoneally vaccinated by injection of 0.1 ml of vaccine, all vaccination 400 day-degrees (atu) before challenge. Because of unexpected low mortality in the control group injected saline the smolts were stressed twice after 3 weeks by lowering the water level for one hour.

Figures 3A, 3B:
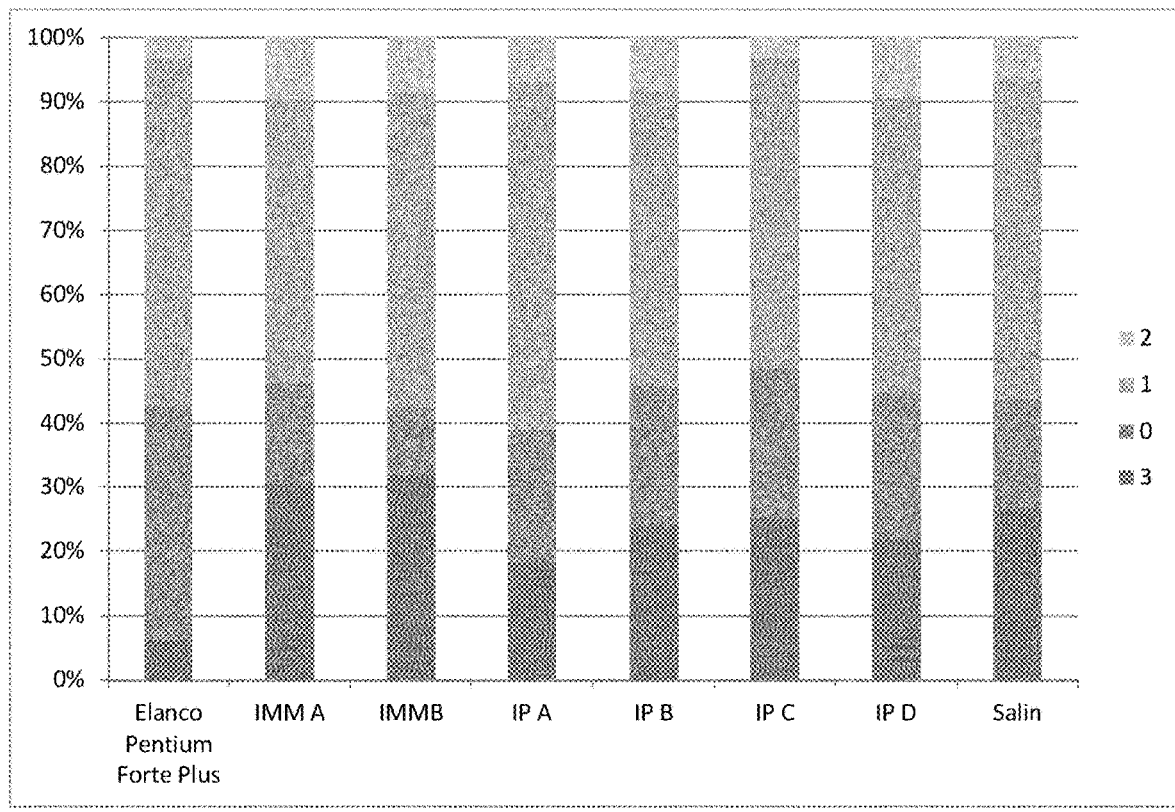

FIGS. 3*a* and 3*b*

Ulcer scoring of all Atlantic smolt involved in the V-3559 study. The smolts were sorted in four groups according to the severity of the changes in the skin. Group 3 had a normal skin with no changes, Group 0 had bleedings and oedema in the scale pockets with raised scales, Group 1 had perforated skin with one or more ulcers of a size of up to 5 mm in diameter and Group 2 more than one large or deep ulcer perforating into the muscle layer subcutaneously.

FIG. 4

Fish in group A were bath challenged 42 days after vaccination with a mix of *Moritella viscosa*, *A. wodanis* and *Tenacibaculum* sp. by adding 1000 mL culture at a concentration of O.D. 1.0 to the fish tanks. This challenge did, however, not induce mortality at the anticipated rate. This group was thus challenged again 75 days later—this time with I.P injection of 0.1 mL *Aliivibrio salmonicida* (O.D. 1.0 concentration). The last challenge induced a rapid increase in mortality rates and the group was terminated after 6 days.

Fish in group B were challenged with natural sea water 42 days after vaccination. This challenge did only induce marginal mortality even after 75 days. Thus in order to achieve a mortality rate that will be sufficient for efficacy testing a challenge with a *Moritella viscosa* bath after 75 days and an *Aliivibrio friggiae* i.p. challenge was done on the $117^{th}$ day after sea water challenge.

FIG. 5

Survival in group A of example 4 from Day 1 to end of study at Day 131. At Day 43 two strains of *Moritella viscosa* and one strain of *Aliivibrio wodanis* were used in bath challenge and at Day 117 *Aliivibrio salmonicida* was used in ip challenge of the remaining Atlantic salmon.

FIG. 6

Survival curves of fish in group A of example 4 from day 117 to end of study at day 131. Prior to day 117 mortality was low. At day 117 fish were IP challenged with *Aliivibrio salmonicida* (day 0 in figure).

FIG. 7

Survival in group B of example 4 from Day 1 to end of study at Day 194. At Day 117 three strains of *Moritella viscosa* were used in a bath infection for one hour and at Day 160 *Aliivibrio friggiae* was used in ip challenge of the remaining Atlantic salmon.

FIG. 8

Survival curves of fish in Group B of example 4 from challenge at day 160 to end of study at day 194. Prior to day 160 mortality was low. At day 160 fish were IP challenged (day 0 in figure) with *Aliivibrio friggiae*.

FIG. 9

Details of the paw of dog 4 before and after (10 days later) treatment with the vaccine. In the left image, there is a red infection between the toes. In the right image the infection is reduced and the symptoms of inflammation are milder.

FIG. 10

To the left are the legs of dog 5 with dog 6 in the background. Dog 5 has infectious wounds on the legs. To the right, after treatment, the skin of dog 5 has healed. These are typical picture of the skin of the dogs before and after treatment with the vaccine.

FIG. 11

A typical picture of the skin of the mandibula of a dog before (left) and after (right) treatment with the vaccine.

FIG. 12

The pony Danica: The large ulcer was surgically removed. After vaccination the infection in the skin reduced and no new ulcers grew.

DETAILED DESCRIPTION

The present document is directed to a method for producing an improved bacterial vaccine composition against bacterial diseases in animals, a bacterial vaccine composition obtained or obtainable by such a method and medical uses thereof. The method involves exposing the bacteria to different growth conditions and then preparing a bacterial vaccine composition with the bacteria exposed to the different growth conditions. It was surprisingly found that when vaccines were prepared by the present method, bacterial diseases that previously had not been able to be cured could be treated and/or that the effect of the treatment was more long-lasting. Another effect that was observed was that the side-effects of inflammation and fibrin production in the abdomen could be avoided due to a lower necessary amount of adjuvant in the bacterial vaccine composition, see Example 2.

The various tissues of an animal body have various levels of the common factors included in the media used for preparing the different cultures in the method of the present document. By using such tissue factors in the media it was possible to build an optimal antigen composition of a bacterial vaccine composition which mimics the conditions the bacteria live before and during a bacterial infection and during restoration after an infection.

Without wishing to be bound by theory, it is thus believed that the present method allows for the preparation of bacterial vaccine compositions comprising bacteria with an antigenic presentation which better mimics the antigenic presentation of the bacteria in the various tissues of an animal's body under conditions prevailing when the diseases caused by bacteria occur, than commonly used methods for preparing vaccines allow for. The bacterial vaccine composition of the present document thus allows for a better vaccination effect. This effect is due to the presence of different tissue factors in the media used for preparing the different cultures A-H disclosed herein.

Thus, depending on the bacterial disease to be treated and/or prevented different combinations of cultures A-H may be used. If for example a blood infection is to be treated, then the cultures that mimic the conditions in blood should be prepared while if a skin infection is to be treated, the cultures that mimic the conditions in skin should be prepared. For some infections it is good to use all variants of antigens (i.e. all of cultures A-H) and then compose different levels of the various antigen types depending on what is expected during the start of the infectious condition and the development during inflammation. Preventive vaccines needs to have focus on the carrier state in the tissues and the initial development of the pathogenesis of a bacterial infection.

For exemplary purposes only, the following bacterial vaccine compositions, wherein the cultures comprises or consists of the below mentioned cultures, may be prepared for treating the following bacterial diseases (factors and conditions during the preparation of the different cultures which are of importance for each specific type of bacterial disease (infection) are given within parenthesis):

Septicemic (blood) infection: E F H (factors common in blood and high oxygen levels)

Dermal and sub-dermal (skin) infections: cultures A B C G H (cell rich, connective tissue, blood factors)

Soft connective tissue: cultures B C E G H (cell rich collagen rich, low oxygen common, low nutrients)

Cartilage and bone infections: cultures A B C F G (little blood, low oxygen, rich in collagen, low in nutrients)

Mucosal membrane infections including intestinal, airway and sexual organ surfaces: cultures A B C E H (little blood, low oxygen, nutrient rich, blood factors)

Lung infections: cultures B C E G H (cell rich, blood factors, high oxygen, collagen and elastin high)

Parenchymatous organs as liver, kidney, spleen: cultures A B D E G H (cell rich, blood factors, low oxygen in periods, rich in nutrients)

Central nervous system: cultures A B C D G (low in oxygen, rich in cells, high in connective tissue as glia and myelin)

Method for Producing the Bacterial Vaccine Composition

The present document is therefore directed to a method for producing a bacterial vaccine composition against bacterial disease in animals, such as fish or mammals, wherein said bacterial vaccine composition comprises inactivated bacteria of the bacterium (or bacteria for co-infections), causing said bacterial disease, said method comprising preparing one or more of cultures A to H by:

i) preparing a culture A by first preparing a pre-culture a. by inoculating said bacterium in 0.5 to 3.5%, such as 0.9% NaCl and incubating from minutes to hours before transferring said pre-culture a. to a nutrient-rich bacterial growth medium, such as Luria broth (10 g tryptone, 5 g yeast extract, 5 to 35 g (such as 9 g) NaCl per liter) with 0.5 to 3.5%, such as 0.9% NaCl, and incubating under microaerophilic conditions to prepare culture A;

ii) preparing a culture B by first preparing a pre-culture a. by inoculating said bacterium in 0.5 to 3.5%, such as 0.9% NaCl and incubating before transferring said pre-culture a. to cell culture medium for fish or mammalian cells, such as RPMI medium 1640, DMEM+GlutaMAX, AIM-V+AlbuMAX, or Leibowitz medium, and incubating under microaerophilic conditions to prepare culture B;

iii) preparing a culture C by first preparing a pre-culture b. by inoculating said bacterium in cell culture medium for fish or mammalian cells, such as RPMI medium 1640, DMEM+GlutaMAX, IM-V+AlbuMAX, or Leibowitz medium, and incubating from minutes to hours before transferring said pre-culture b. to a solution comprising typical 3.2% (w/v) (variation from below 0.5 to 15% (w/v)) gelatin (hydrolyzed gelatin or any other intact or partially degraded form of all types of gelatin; typical a mixture of type 1 from soft tissues and type 2 from cartilage and bone tissues and others of the close to 30 forms of gelatin) with 1% glucose (0.05 to 1.5%) and incubating under microaerophilic conditions to prepare culture C;

iv) preparing a culture D by first preparing a pre-culture c. by inoculating said bacterium in blood, plasma or serum, e.g. from horses, and incubating from minutes to hours before transferring said pre-culture c. to brain heart infusion medium (BHI) with 1% glucose (0.05 to 1.5%) and incubating under microaerophilic conditions to prepare culture D;

v) preparing a culture E by inoculating said bacterium in enrichment broth that may vary depending on the various bacteria involved, normally a nutrient-rich medium but sometimes a medium with a low level of nutrients or with certain nutrients or components added or removed, and incubating under aerobic conditions to prepare culture E;

vi) preparing a culture F by transferring bacteria from culture E or from enrichment medium containing for example blood, plasma and/or serum to 0.5 to 3.5%, such as 0.9% NaCl;

vii) preparing a culture G by transferring bacteria from culture E or from enrichment medium containing for example blood, plasma and/or serum to a cell culture medium for fish or mammalian cells, such as RPMI medium 1640, DMEM+GlutaMAX, AIM-V+AlbuMAx, or Leibowitz medium;

viii) preparing a culture H by transferring bacteria from culture E or from enrichment medium containing for example blood, plasma and/or serum to blood, plasma or serum, e.g. from horses;

ix) inactivating the bacteria in cultures A-H;

x) optionally washing the inactivated cultures of step vii), such as in phosphate buffered saline (PBS); and xi) if more than one culture is prepared, mixing the optionally washed and resuspended inactivated cultures to prepare the bacterial vaccine composition;

wherein step xi) of mixing the cultures optionally may be performed before step ix) or before step x) instead of after step x);

with the proviso that if culture E is prepared, then at least one of cultures A-D or F-H is also prepared.

The ratio of pre-culture to culture medium in steps i)-iv) is for example ¼ although also other ratios can be used, such as ½, ⅓, ⅕, ⅙, ⅐, ⅛, ⅑ or ⅒. The exact inoculum-to-fresh culture ratio is not critical. However it is preferable to add less inoculum volume than the volume of fresh medium.

The bacterium of interest is preferably taken from a fresh bacterial culture on e.g. enrichment medium (broth or plates), containing for example blood, plasma or serum, e.g. blood plates.

Typically, the bacterial vaccine composition prepared comprises only one bacterial strain and/or species although it may be possible to prepare a bacterial vaccine composition comprising two or more bacterial strains and/or species/sub-species cultured separately or cultured as co-cultures of two or more bacterial strains, sub-species or species. Such a bacterial vaccine composition comprising two or more bacterial strains and/or species/sub-species may be prepared either by including the two or more bacterial strains and/or species/sub-species in each of the cultures A-H during the preparation thereof or by preparing separate cultures A-H with the different bacterial strains and/or species/sub-species and mixing them together before or after inactivating the bacteria. For example, the bacterial vaccine composition prepared may comprise several bacterial species, sub-species or strains of the same species each causing a separate disease, several different bacteria causing a disease as a co-infection, or a mix of bacterial species, sub-species or strains of several co-infections. In the context of the present document, even if the bacterial vaccine composition comprises more than one strain, sub-species and/or species of bacteria and even if the bacterial vaccine composition may be used to treat more than one bacterial disease, these variations are all encompassed in the expression "said bacterial vaccine composition comprises inactivated bacteria of the bacterium causing said bacterial disease" and the like, i.e. this expression is not limited to the treatment and/or prevention of a single bacterial disease caused by a single bacterial species, sub-species or strain.

In the present method, one or more of cultures A-H are prepared and if more than one of the cultures A-H is to be present in the vaccine, the cultures are mixed after or before inactivation to prepare the bacterial vaccine composition. The present method typically comprises preparing two or more of the cultures A-H, such as three, four, five, six, seven or all eight of cultures A-H. Preferably, all of cultures A-H are prepared.

Typically, one of the cultures prepared in the present method is culture A and/or culture D. After the one or more of cultures A-H is/are prepared, the bacteria are inactivated. The term "inactivated" refers to that the bacteria, due to one or more modifications, have lost their virulence, but are still able to induce an immune response in a recipient, which immune response is sufficient to provide an immunizing effect. Methods for inactivating bacteria include e.g. the use of formalin, heat inactivation, inactivation by use of radiation or antibiotics, and attenuation of bacterial cells.

Normally formalin is used for inactivating bacteria included in bacterial vaccine compositions. Formalin inactivation of bacteria may typically be performed by adding formalin to a bacterial culture, such as about 1% formalin, for e.g. two hours or overnight, before washing the killed bacteria. However, formalin is considered to be an active denaturing agent of proteins resulting in a discrepancy between the acquired immunological memory based on denatured bacterial surface proteins and the natural proteins of the pathogen approaching the host. This "blurred" image of the pathogen may be sharper by inactivating the bacterial cells prepared for the vaccine by a temperature above the level where the bacteria can survive but still below the temperature when the bacterial proteins denatured by heat, typically above 40-42° C. The same sharp immunological memory image of the outlook of the pathogen is also acquired by inactivating the bacteria by radiation or chemicals degrading specifically the nucleic acids. However, studies have indicated that formalin-killed bacteria in general may be stronger antigens and thereby cause a better immune reaction than the natural antigens.

Heat may also be used as an inactivation method. Typically, a temperature of from about 30° C. to about 50° C., such as from about 30° C. to about 40° C., is used. The time for heat treatment is typically from about 1 hour to about 24 hours, such as from 5 to about 24 hours, such as from about 10 to about 20 hours, such as for 5, 6, 7, 8, 9, 10, 11, 12, 13, 14, 15, 16, 17, 18, 19, 20, 21, 22, 23, 24 hours. Heat inactivation with relatively low temperature keeps the antigens natural without being denatured, and therefore is particularly useful in the present context. Heat treatment may for example be carried out by heating the bacteria to about 30° C. for a time period sufficient for inactivating the bacteria normally grown at low temperature of close to 10° C., such as e.g. about 16 hours Attenuation as a means for effecting inactivation of bacteria may be performed by repeated cultivations with or without mutagenic chemicals in the culture, by radiation or any other relevant measure until random mutations occur in one or more genes relevant for successful pathogenesis. Alternatively, attenuation of the bacteria by directed knock-out mutations of one or more of the virulence genes may be used. Attenuation of the bacteria thus means a weakening of the bacteria so that their ability to cause disease is reduced or lost while they are still able to induce an immune response when administered to a subject.

The viability of the bacterial cells after inactivation may be controlled by cultivation on a suitable growth medium.

Inactivation and viability check may, for example, be put in effect in the following manner: Formalin in a final concentration of 0.6% is added to the bacterial cultures prepared. The resulting solution with bacterial cells and formalin is stirred in room temperature (22° C.±2° C.) in 48 hours. The cultures are then centrifuged, washed 2× and resuspended in PBS (phosphate buffered saline). After inactivation, all bacteria are re-cultivated on blood plates (or other enrichment plates) to control the sterility. These controls are incubated for at least one week. The vegetative cells of culture E (if present) are adjusted with PBS to an OD600=1.0. The bacteria are resuspended in the volumes they are cultured in. The inactivated cultures are then stored at +4° C.

After inactivating the bacteria, the bacterial cells are optionally washed, such as in PBS. This washing may be performed by centrifuging the cells to form a pellet containing the bacterial cells, pouring off the liquid and resuspending the bacteria in e.g. PBS. The cells may be washed one or more times, such as two or three times.

If more than one of cultures A-H is prepared, two or more of the cultures may be mixed before the cultures are inactivated, or after inactivation. In the latter case, the mixing may be performed before or after washing and resuspending the inactivated cultures. Not all of the cultures need to be mixed at the same time point and step in the method, but some may e.g. be mixed before inactivation and some only after (before and/or after washing and resuspending), i.e. not all of the prepared cultures need to be mixed with each other at the same step.

More than one strain of different taxa may also be co-cultured as pre-cultures to the protocol and also added as additional strain to a live culture at a secondary or tertiary step of the various parts of the protocol.

Bacterial isolates (i.e. the bacterium/bacteria that causes the disease to be treated with the produced bacterial vaccine composition) that can be applied in the described method for producing a bacterial vaccine composition may typically be isolated from a diseased individual to which the bacterium is contributing to the disease or from an individual that is carrying the bacterium that may cause disease but that has not developed the disease. The isolate may represent a strain that infects many individuals in an outbreak of disease or it may be an isolate that typically cause disease in one single or in a few individuals. The bacterial isolate may or may not be identified in either relevant way to a known bacterial taxum before being stored in either way for instance in freezer, as freeze-dried or as stab culture before being cultured as pre-culture to this protocol. At some occasions the culture may be taken directly from the primary culture or after being passed through a research animal, cell culture or the natural host for the use as pre-culture for this protocol. Bacterial isolates of different species or sub-species being the causative agents of two or more separate diseases can be prepared with the protocol described in this document and mixed into one single vaccine that protects against more than two different diseases. Separate vaccines made according to this protocol comprised of one or two or more bacterial strains can be used to protect against or treat various diseases in the same individual.

Bacterial isolates used as pre-culture(s) for the present method (vaccine preparation protocol) may be cultured as single isolates typically representing mono-infections in the affected host or may be cultured as combined cultures of two or more co-cultured bacteria as pre-culture for this protocol representing mixed infections or co-infections causing disease.

The pre-cultures used for the vaccine preparation protocol described here may represent one bacterial strain or more than one and up to a long series of single bacterial strains and/or co-cultures of bacterial strains cultured as single cultures as pre-cultures for the vaccine preparation protocol or as co-cultures of bacteria not included as single strains in the pre-culture. The strains may be the causative agent of one or more diseases.

The combination of many single strains of bacteria and various mixtures of two or more bacterial strains is also relevant for the various steps of the vaccine preparation protocol for instance by mixing single strain cultures in the second or third successive manipulation step of the live bacterial strains at any step in the vaccine preparation protocol.

The time and temperature for the incubation in the different steps of the method according to the present document will depend on the bacterium of interest but the temperature will in general be the one commonly used for growing the bacterium of interest i.e. the body temperature typical for the host of the bacterial infection typically varying from about 8 to about 12° C. in salmonids to about 37 to about 38° C. in mammals and the time will in general be the time necessary to allow for a late exponential phase or early stationary phase culture to form varying from overnight (i.e. about 16 hours) to about 5 days or more depending on the bacteria and host species of origin, such as 1, 2, 3, 4, 5, 6, 7, 8, 9, or 10 days. However, in some steps of the method, no incubation time or a very short incubation time is necessary.

Preparation of Culture A

Culture A is prepared by first preparing a pre-culture a. by inoculating the bacterium of interest in about 0.5 to 3.5%, such as 0.9% NaCl, and incubating, such as for 1 to 2 hours (but both shorter and longer incubation time are also functional), before transferring said pre-culture a. to a nutrient-rich bacterial growth medium, such as Luria broth (10 g tryptone, 5 g yeast extract, and 9 g NaCl per liter) with about 0.5 to 3.5%, such as 0.9% NaCl, for example in a ratio of ¼ of pre-culture a. to Luria broth, and incubating under microaerophilic conditions to prepare culture A. The time and temperature for the incubation will depend on the bacterium of interest but the temperature will in general be the one commonly used for growing the bacterium of interest i. e. the dominant body temperature of the host of the bacterial pathogen and the time will in general be the time necessary to allow for a late exponential phase of the growth or, for some bacteria, an early stationary phase culture to form.

Preparation of Culture B Culture B is prepared by first preparing pre-culture a. as disclosed above. Pre-culture a. is then transferred to a cell culture medium for fish or mammalian cells, such as RPMI medium 1640, DMEM+GlutaMAX, AIM-V+AlbuMAx, or Leibowitz medium. The medium to be used for preparing culture B should have a content of nutrients which is about the same as the nutrients that are present in arterial blood. The ratio of culture a. to cell culture medium may for example be ¼ of culture a. to cell culture medium. The culture is incubated under microaerophilic conditions to prepare culture B. The time and temperature for the incubation will depend on the bacterium of interest but the temperature will in general be the one commonly used for growing the bacterium of interest and will be the normal body temperature of the host of the particular infection caused by the bacterial pathogen. The time of incubation will be the time necessary to allow for a late exponential phase or early stationary phase culture to form varying from overnight (i.e. about 16 hours) to 5 days or more depending on the bacteria and host species of origin.

Preparation of Culture C

Culture C is prepared by first preparing a pre-culture b. by inoculating the bacterium of interest in cell culture medium for fish or mammalian cells, such as RPMI medium 1640, DMEM+GlutaMAX, AIM-V+AlbuMAx, or Leibowitz medium (i.e. a cell culture medium having a content of nutrients which is about the same as the nutrients that are present in arterial blood as disclosed under Culture B above), and incubating, such as for 1 to 2 hours but both shorter and longer incubation time is functional, before transferring said pre-culture b. to a solution comprising typically about 3.2% (w/v) (variation from below 0.5 to 15% (w/v)) gelatin, hydrolyzed gelatin or any other degraded form of gelatin (including various types of gelatin as type 1 from soft tissues and type 2 from cartilage and bone tissue including as many as possible of the close to 30 forms of gelatin (collagen forms) as a mix or as one single type or a mix of two or more types of gelatin dependent of the tissue where the pathogenic bacteria are located under disease development) with about 1% (or any similar concentration, typically from about 0.1 to about 1.5%) glucose or any sugar that the said bacterium is able to utilize, such as in a ratio of ¼ of culture b. to the gelatin/glucose solution and incubating under microaerophilic conditions to prepare culture C. The time and temperature for the incubation will depend on the bacterium of interest but the temperature will in general be the one commonly used for growing the bacterium of interest i. e. the body temperature typical for the host of the bacterial infection typically varying from 8 to 12° C. in salmonids to 37 to 38° C. in mammals and the time will in general be the time necessary to allow for a late exponential phase or early stationary phase culture to form varying from overnight (i.e. 16 hours) to 5 days or more depending on the bacteria and host species of origin.

Preparation of Culture D

Culture D is prepared by first preparing a pre-culture c. by inoculating the bacterium of interest in blood, plasma or serum, e.g. blood serum from horses, and incubating such as for 1 to 2 hours. However shorter and longer time of incubation can be functional before transferring said pre-culture c. to brain heart infusion medium (BHI) or similar generic medium containing tissue components from the nervous system and heart muscle tissue with 1% (0.1 to 1.5%) glucose, such as in a ratio of ¼ of culture c. to brain heart infusion medium (BHI) or similar medium and incubating under microaerophilic conditions to prepare culture D. The time and temperature for the incubation will depend on the bacterium of interest but the temperature will in general be the one commonly used for growing the bacterium of interest that will be the normal body temperature of the host of the particular infection caused by the bacterial pathogen, in general and the time will in general be the time necessary to allow for a late exponential phase or early stationary phase culture to form varying from overnight (i. e. about 16 hours) to 5 days or more depending on the bacteria and host species of origin.

Preparation of Culture E

Culture E is prepared by inoculating the bacterium of interest in an enrichment broth that typically does not contain inhibitory components to the bacterium inoculated and that contain a high level of nutrients that support growth of the bacterium inoculated. Luria broth (10 g tryptone, 5 g yeast extract, and 9 g NaCl per liter) with about 0.9% (0.5 to 3.5%) NaCl is a commonly used enrichment broth in the field of science and can be inoculated with the bacterial strain of interest and incubated under aerobic conditions to prepare culture E. The time and temperature for the incubation will depend on the bacterium of interest but the temperature will in general be the one commonly used for growing the bacterium of interest and the time will in general be the time necessary to allow for a late exponential phase or early stationary phase culture to form varying from overnight (i.e. about 16 hours) to 5 days or more depending on the bacteria and host species of origin. Culture E represents the vegetative form of the bacterial cells. If culture E is prepared, at least one more of cultures A-D or F-H has to prepared and mixed with culture E in the final vaccine preparation.

Preparation of Culture F

Culture F is prepared by transferring bacteria from culture E to 0.9% NaCl. Alternatively, instead of taking the bacteria from culture E, the bacteria may be taken from enrichment medium (broth or plates), containing for example blood, plasma or serum, e.g. blood plates. No incubation is necessary, but an incubation of minutes to hours can be done, i.e. the bacteria may be directly inactivated.

Preparation of Culture

Culture G is prepared by transferring bacteria from culture E to a cell culture medium for fish or mammalian cells, such as RPMI medium 1640, DMEM+GlutaMAX, AIM-V+ AlbuMAX, or Leibowitz medium. Alternatively, instead of taking the bacteria from culture E, the bacteria may be taken from enrichment medium (broth or plates), containing for example blood, plasma or serum, e.g. blood plates. No incubation is necessary, but an incubation of minutes to hours can be done, i.e. the bacteria may be directly inactivated.

Preparation of Culture H

Culture H is prepared by transferring bacteria from culture E to blood, plasma or serum, e.g. blood serum from horses. Alternatively, instead of taking the bacteria from culture E, the bacteria may be taken from enrichment medium (broth or plates), containing for example blood, plasma or serum, e.g. blood plates.

No incubation is necessary, but an incubation of minutes to hours can be done, i.e. the bacteria may be directly inactivated.

As mentioned above, if more than two cultures are prepared two or more of the cultures A-H (independently of whether these are prepared as single cultures or as co-cultures) may be mixed together before inactivation, after inactivation but before the optional step of washing and resuspending the inactivated cultures, and/or after the optional step of washing and resuspending the inactivated cultures. It may be preferable to inactivate the bacterial cultures before mixing two or more of them together. Also, it may be preferred to inactivate the bacterial cultures as soon as possible after cultivation (i.e. directly after cultivation).

As is described above, some of the cultures are incubated under microaerophilic conditions meaning that the cultures are incubated under conditions with lower concentrations of oxygen than in normal air, i.e. less than 21% and typically about 2-10% $O_2$.

The above method may be followed by a step of mixing the bacterial vaccine composition obtained with an adjuvant. Examples and amounts of adjuvants are disclosed elsewhere herein.

The present document is also directed to a bacterial vaccine composition obtained or obtainable by the method disclosed herein.

The Bacterial Vaccine Composition

As mentioned above, the present document is also directed to a bacterial vaccine composition obtained or obtainable by the herein disclosed method for preparing a bacterial vaccine composition. The bacterial vaccine composition is prepared using the herein disclosed method for preparing a bacterial vaccine composition.

The bacterial vaccine composition comprises inactivated bacteria of a bacterium causing said bacterial disease obtained or obtainable by a method for producing a bacterial vaccine composition as disclosed herein.

The present document thus discloses a bacterial vaccine composition against bacterial disease in animals, such as fish or mammals, wherein said bacterial vaccine composition comprises inactivated bacteria of the bacterium (or bacteria for co-infections), causing said bacterial disease, said bacterial vaccine composition being obtained or obtainable by a method comprising preparing one or more of cultures A to H by:

i) preparing a culture A by first preparing a pre-culture a. by inoculating said bacterium in 0.9% NaCl and incubating for a period of 1 to 2 hours or shorter or longer if convenient before transferring said pre-culture a. to a nutrient-rich bacterial growth medium, such as Luria broth (10 g tryptone, 5 g yeast extract, 9 g NaCl) with 0.9% (0.5 to 3.5%) NaCl in a ratio of ¼ of pre-culture a. to Luria broth and incubating under microaerophilic conditions to prepare culture A;

ii) preparing a culture B by first preparing a pre-culture a. by inoculating said bacterium in 0.9% NaCl and incubating for a period of 1 to 2 hours or shorter or longer if convenient before transferring said pre-culture a. to cell culture medium for fish or mammalian cells, such as RPMI medium 1640, DMEM+GlutaMAX, AIM-V+ AlbuMAx, or Leibowitz medium, in a ratio such as of ¼ of culture a. to cell culture medium and incubating under microaerophilic conditions to prepare culture B;

iii) preparing a culture C by first preparing a pre-culture b. by inoculating said bacterium in cell culture medium for fish or mammalian cells, such as RPMI medium 1640, DMEM+GlutaMAX, AIM-V+AlbuMAx, or Leibowitz medium, and incubating for a period of 1 to 2 hours or shorter or longer if convenient before transferring said pre-culture b. to a solution comprising typically 3.2% (w/v) between from below 0.5 to 15% (w/v) gelatin with 0.05 to 1.5% glucose such as 1%, in a ratio of such as ¼ of culture b. to the gelatin/glucose solution and incubating under microaerophilic conditions to prepare culture C;

iv) preparing a culture D by first preparing a pre-culture c. by inoculating said bacterium in blood, plasma or serum, e.g. from horses, and incubating before transferring said pre-culture c. to brain heart infusion medium with 0.05 to 1.5% glucose such as 1%, in a ratio of such as ¼ of culture c. to brain heart infusion medium and incubating under microaerophilic conditions to prepare culture D;

v) preparing a culture E by inoculation said bacterium in enrichment broth that typically does not contain inhibitory components to the bacterium inoculated and that contain a high level of nutrients that support growth of the bacterium inoculated. Luria broth (10 g tryptone, 5 g yeast extract, and 9 g NaCl per liter) with about 0.9% (0.5 to 3.5%) NaCl is a commonly used enrichment broth in the field of science and can be inoculated with the bacterial strain of interest before incubating under aerobic conditions to prepare culture E;

vi) preparing a culture F by transferring bacteria from culture E or from enrichment medium containing for example blood, plasma and/or serum to 0.9% NaCl;

vii) preparing a culture G by transferring bacteria from culture E or from enrichment medium containing for example blood, plasma and/or serum to a cell culture medium for fish or mammalian cells, such as RPMI medium 1640, DMEM+GlutaMAX, AIM-V+Albu-MAx, or Leibowitz medium;

viii) preparing a culture H by transferring bacteria from culture E or from enrichment medium containing for example blood, plasma and/or serum to blood, plasma or serum, e.g. from horses;

ix) inactivating the bacteria in cultures A-H;

x) optionally washing the inactivated cultures of step vii), such as in phosphate buffered saline (PBS); and xi) if more than one culture is prepared, mixing the optionally washed and resuspended inactivated cultures to prepare the bacterial vaccine composition; wherein step xi) of mixing optionally may be performed before step ix) or before step x) instead of after step x), with the proviso that if culture E is prepared, then at least one of cultures A-D or F-H is also prepared. Further details regarding the method steps is disclosed above.

Further details regarding the preparation and composition of such a bacterial vaccine composition are disclosed elsewhere herein. The bacterial vaccine composition may comprise or consist of one of cultures A-H with the proviso that if culture E is present, then at least one of cultures A-D or F-H is also present. The bacterial cultures of the bacterial vaccine composition typically comprises or consists of two or more of the cultures A-H, such as three, four, five, six, seven or all eight of cultures A-H.

The bacterial vaccine composition may further comprise an adjuvant and/or a pharmaceutically acceptable excipient. The choice of adjuvant is not critical, but typical examples of suitable adjuvants include, but are not limited to, FICA oil and Curdlan, such as a mix of FICA oil and Curdlan in a ratio of 40-60 wt % FICA to Curdlan, such as 40%, 50% or 60% of FICA oil to Curdlan.

In addition to the inactivated bacteria, and/or one or more components and/or antigenic part(s) thereof and/or adjuvants in a bacterial vaccine composition, emulsifiers (emulgator) may be added, such as highly refined polyoxyethylenesorbitan and sorbitan oleates, such as polysorbate 85, polysorbate 80, PEG-6 sorbitan oleate, and sorbitan oleate etc. Emulsifiers are added to stabilize the vaccine emulsion in particular when mineral oils are added as an adjuvant. When oil-in-water or water-in-oil emulsions are made they may be instable if not used soon after. It is also possible to instead if adding an external emulsifier, to emulgate mechanically and use the vaccine the same day as it is prepared. For vaccines that need to be stored, emulsifiers are often added in a mixture of up to typically 3 to 4 in accordance with procedures known to the manufacturer. A successful emulsifier-mix makes it possible to store the vaccine effectively for a longer period. Typically from 5% and up to 10 or 12% emulsifier can be part of a commercial bacterial vaccine composition. However, methods and means for preparing a bacterial vaccine composition suitable for storage are well known for the skilled practitioner within this field.

Vaccine components may be in liquid form both as hydrophilic and lipophilic, which may often then be mixed in emulsions that need to be stabilized for storage. Examples may be found in Roar Gudding (Editor) et al. "Fish Vaccinology", Developments in Biological Standardization, 484 pages.

In addition, dry vaccines may also be prepared from the compositions as disclosed herein, and then dissolved before usage. This is particularly for, dip, bath or oral vaccines that are not using oil adjuvants or the like.

The amount of the different cultures A-H when all cultures are present in the bacterial vaccine composition may e.g. be A 8.6%, B 8.6%, C 8.6%, D 8.6%, E 40%, F 8.6%, G 8.6%, and H 8.6% (volume ratio).

Alternatively, the amount of the different cultures may be A 10%, B 10%, C 10%, D 15%, E 40%, F 5%, G 5% and H 5% (volume ratio). However, other ratios between the different cultures may be used depending on the typical character of the site of infection including the way bacteria act during the various infections. Typically, each culture makes up at least 1 v/v % of the bacterial cultures in the vaccine compositions, such as 2, 3, 4, 5, 6, 7, 8, 9, or 10 v/v % thereof.

Medical Use of the Bacterial Vaccine Composition

The present document is also directed to a bacterial vaccine composition for treating and/or preventing a bacterial disease. The term "bacterial disease" may in the context of the present document be a bacterial disease caused by one type of bacterium or a disease caused by two or more bacterial species, such as a co-infection caused by two or more bacterial species. The "bacterial disease" may in this context also refer to two or more separate bacterial diseases. The bacterial vaccine composition in the context of the medical uses herein is the bacterial vaccine composition obtained or obtainable by the method disclosed herein.

The present document is thus directed to the bacterial vaccine composition disclosed herein for use in the treatment and/or prevention of a bacterial disease caused by said bacterium.

The present document is also directed to the use of the bacterial vaccine composition disclosed herein for the manufacture of a vaccine for the treatment and/or prevention of a bacterial disease caused by said bacterium.

The present document is also directed to a method for treating and/or preventing a bacterial disease, said method comprising the step of administering a pharmaceutically effective amount of the bacterial vaccine composition disclosed herein to a subject in need thereof for treating and/or preventing a bacterial disease caused by said bacterium.

As disclosed elsewhere herein, the bacterial vaccine composition may comprise bacteria from more than one bacterial strain and/or species and/or the vaccine may be used for treating one or more bacterial infections, such as a co-infection caused by two or more different bacterial species and/or different bacterial diseases caused by different bacterial species. The term "said bacterium" in the medical uses disclosed herein thus includes both single bacterial strains and/or species and combinations of two or more bacterial strains and/or species.

The bacterium causing the bacterial disease to be treated and/or prevented may be selected from the group consisting of *Staphylococcus pseudintermedius, Aeromonas salmonicida, Tenacibaculum dicentrarchi, Moritella viscosa, Aliivibrio wodanis. Vibrio anguillarum, Aliivibrio salmonicida, Aliivibrio friggiae, Bizionia piscinecroseptica, Aliivibrio hodis, Aliivibrio heliae, Photobacterium pisciinfectiosa, Staphylococcus aureus, Streptococcus equi*, although it is not limited thereto.

The subject to which the bacterial vaccine composition is to be administered is typically a tetrapod, such as a mammal, such as a dog, cat, horse, cow, sheep, goat, pig, or human, or a bird, such as chicken, hen or turkey or a vertebrate, such as a fish, such as a teleost, such as salmon, sea bass, or trout.

The bacterial disease to be prevented and/or treated with the bacterial vaccine composition is typically a chronic or acute bacterial disease, such as an infection caused by *Staphylococcus pseudintermedius*, such as in a in dog, such as skin infection, such as deep furunculosis or superficial impetigo or ear infections. Further examples of bacterial diseases that can be treated and/or prevented by use of the bacterial vaccine composition disclosed herein include, but is not limited to, winter ulcer e.g in Atlantic salmon, such as winter ulcer caused by *M. viscosa, Aliivibrio wodanis* and/or other bacteria, ulcer and/or fin rot in many fish species, vibriosis, cold-water vibriosis and furunculosis e.g. in salmonids or other farmed fish species.

The subject to which the bacterial vaccine composition is administered may already be infected by the bacterium, i.e. the bacterial vaccine composition is administered to treat or control a bacterial disease (infection), or the bacterial vaccine composition may be administered before infection has occurred, i.e. the bacterial vaccine composition is administered to prevent an infection.

The bacterial vaccine composition is typically administered intraperitoneally or subcutaneously. However, depending on the disease to be prevented and/or treated or the type of subject to be treated other administration routes may be applied, such as bath vaccination, dip vaccination or oral vaccination, e.g. as a sole entity or in the feed. Bath or dip vaccination is particularly suitable when fish are to be vaccinated and includes exposing the fish to water provided with the bacterial vaccine composition. It is also possible to administer the bacterial vaccine composition topically, e.g. to the mucous membranes, such as in the nose, in the airways, such as in the lungs, in the mouth, anally and/or through the mucous membranes of the sexual organs. These routes of administration may be particularly suitable for administration of the bacterial vaccine composition to tetrapods, such as mammals.

The disclosure of the invention will be further described in the following examples, which do not limit the scope of the invention described in the claims.

EXPERIMENTAL SECTION

Example 1: Protocol for Vaccine Production

Fresh bacterial cells were taken from enrichment plates (ex. blood plates) and used for the inoculations in the different media.
Preparation of Cultures a, B, C, and D:
Tubes with following contents, 500 µl in each tube, were prepared:
 a—Physiological saline water, e.g. 0.9% NaCl
 b—Leibowitz medium (cell culture media)
 c—Blood serum from horses
Bacterial cells were taken from blood plates (with 2.5% additional NaCl for the marine fish pathogenic bacteria and mixed well into the tubes. Pre-cultures a., b. and c. were allowed to incubate for 1 to 2 hours at the body temperature relevant for the bacteria when causing disease, i.e. 10° C. for Atlantic salmon and 37° C. for S. pseudintermedius from dogs. Then 250 µl from each of tubes a-c were transferred as follows:
 From a: 250 µl to tube A: 1000 µl LB (Luria broth) with 0.9% NaCl
 From a: 250 µl to tube B: 1000 µl Leibowitz
 From b: 250 µl to tube C: 1000 µl gelatin 3.2% with 1% glucose
 From c: 250 µl to tube D: 1000 µl BHI (brain heart infusion) with 1% glucose
This gives a total volume of 1250 µl per tube. The cultures were then incubated typical two to seven days under microaerophilic conditions.
Preparation of Culture E:
 5 ml Luria broth (10 g tryptone, 5 g yeast extract, and 9 g (25 g for the marine bacteria) NaCl per litre) in an Erlenmeyer flask was inoculated with fresh bacteria. The cultures were incubated for typical two to four days under shaking to ensure a high $O_2$-level during incubation with typical addition of fresh growth medium every day during the culture period.
Preparation of Cultures F, G, and H:
Tubes with following contents, 1000 µl in each tube, were prepared:
 F—Physiological saline water, e.g. 0.9% NaCl
 G—Leibowitz (cell culture media)
 H—Blood serum from horses
Bacterial cells were taken from blood plates and mixed well into the tubes. These cultures are used directly without incubation.

The volumes can be changed if necessary, but the volume ratio is important but may also vary depending of type of diseases.

After preparation of the bacterial cultures A-H as disclosed above, the bacteria are inactivated with 0.6% formalin. The solution with bacterial cells and formalin is stirred in room temperature (22° C.±2° C.) in 48 hours. The cultures are then centrifuged, washed 2× and resuspended in PBS (phosphate buffered saline). After inactivation, all cultures were checked for viability to ensure that all bacterial cells are inactivated. This was performed on blood plates. These controls were incubated for at least a week. The vegetative cells (E) were adjusted with PBS to an OD600=1.0. The other cultures were resuspended in the volumes they are cultured in. The inactivated bacterial cultures are then stored at +4° C.
Preparation of the Vaccine:
A 1:1 volume ratio between the inactivated bacterial cultures and a FICA (Freunds Incomplete Adjuvant)/Curdlan mix was used.

The volume ratio of the different cultures in the bacterial vaccine composition was as follows:

|    | In percentage, method 1 | In percentage, method 2 |
|----|------------------------|------------------------|
| A: | 10%                    | 8.6                    |
| B: | 10%                    | 8.6                    |
| C: | 10%                    | 8.6                    |
| D: | 15%                    | 8.6                    |
| E: | 40%                    | 40                     |
| F: | 5%                     | 8.6                    |
| G: | 5%                     | 8.6                    |
| H: | 5%                     | 8.6                    |

| Volume ratio adjuvant: Type of adjuvant | Mostly used | Also used 1 | Also used 2 |
|---|---|---|---|
| FICA (oil) | 40% | 50% | 60% |
| Curdlan    | 60% | 50% | 40% |

Curdlan: Concentration: 6.7 g/L

The Curdlan is not well mixed in PBS without adjusting the pH to a higher level. The mixing was thus performed by mixing on a stirrer for an hour without adjusting the pH, or by mixing on a stirrer and slowly adding NaOH until the mixture is homogenous. The pH is then around pH 10.5.
Mixing of the Vaccine (Bacterin and Adjuvants):
Two methods for mixing the bacterial vaccine composition:
 A: The syringe method is well known from before, using two 50 mL syringes with Luer-lock, connected together with a valve (ex. Discofix). This is working good when it's few types of bacterins.

B: Mixing in high speed with a blender for 4-6 minutes. This method is the best when the vaccine is containing several types of bacterins.

The bacterial vaccine composition was a creamy homogenous emulsion, and was stored at +4° C. until use.

Example 2: Vaccination of Farmed Atlantic Salmon Against Furunculosis

Furunculosis caused by *Aeromonas salmonicida* ss *salmonicida*, a Gram-negative salmonid pathogen is one the major threats against farming of Atlantic salmon. In 1985 furunculosis was imported from Scotland to mid-Norway with Atlantic salmon smolts. A high level of antibiotics in medicated feed was established in the attempt of controlling the disease that spread along the Norwegian coast. The vaccines available did not protect efficient against *A. salmonicida* ss *salmonicida*. The fast development of antibiotic resistance against tetracyclines, sulphonamides, trimethoprim and quinolones made the use of antibiotics inefficient before the addition of mineral oil in the adjuvant of the vaccines was tested in the mid-1990's. The mineral oil as adjuvant resulted in 80 to 90% protection. However, a side-effect from the use of mineral oil in the form of inflammation with secondary adhesions between the peritoneum and the organs of the abdomen became a problem that reduced the animal welfare and reduced the quality of the slaughter products. The efficiency of the vaccines against furunculosis has been kept since the mid-90's and the side-effects are still the same but the size of the side-effects has been reduced by reducing the volume of the dose used for intraperitoneal injection with 50% from 0.1 to 0.05 ml for some of the market leaders in the salmon vaccine market.

One of the characteristics of *A. salmonicida* ss *salmonicida* is the ability to establish healthy carriers in the population of salmonids which makes recurrent outbreaks one of the major obstacles in the control of the disease that is most common during the warmer part of the year.

In Norway it has been mandatory until recently to vaccinate all farmed salmonids efficient against furunculosis caused by *A. salmonicida* ss *salmonicida* by governmental regulation.

Clinical Efficacy Study: *Aeromonas Salmonicida* Subspecies *Salmonicida* Dose Titration Study Period:
Start date: Jul. 22, 2015
Duration 4 months (end of the animal phase of the study and final report: December 2015.

Study Population
Clinically healthy Atlantic salmon (Salmo salar) in good health status and negative vaccination status. Minimum size; 20 g. Populations entered into the study was documented to be free from exposure to the disease indications-confirmed at source. Stocking density was kept below 20 kg/m³ during the trial.

Primary Study Objective
To determine the immunity of Atlantic salmon vaccinated with a multivalent water-based vaccine for *Aeromonas salmonicida* (contains multivalent vaccine antigens). This study is a dosing study for the concentration of inactivated cells required for immunogenicity against a standard background of multivalent antigen in an oil adjuvanted vaccine.

Study Design
55 fish per treatment of test vaccines. Fish were given a vaccination with either vaccine containing increasing amounts of *A. salmonicida* cells, a negative test reference vaccine (that does not contain *A. salmonicida* vegetative cells) and a positive reference commercial vaccine according to the label recommendations and kept in clean fresh water (FW) for 400 atu (Accumulated Thermal Units) at ~12° (33 days). A similar group of fish was i.p. vaccinated with saline as a negative control group according to the label directions. The fish were weighed July 22, and the average weight was 24.1 gram. Vaccination was performed August 28 and the challenge started October 2 when the fish was 37.9 gram in average. For the challenge assessment, mortality was observed 47 days post challenge (as per Vikan's model—cohabitation), the study required mortality in the unvaccinated control population to be 60-80% for a valid test.

TABLE 1

Bacterial vaccine composition; group number and fish number

| Vaccine Group (*A. salmonicida* ss *salmonicida* percent volume of total bacterin) | Group Number | Fish Number |
| --- | --- | --- |
| 0% | Group 1 | 55 |
| 1.5% | Group 2 | 55 |
| 3% | Group 3 | 55 |
| 5% | Group 4 | 55 |
| 10% | Group 5 | 55 |
| 15% | Group 6 | 55 |
| 20% | Group 7 | 55 |
| 25% | Group 8 | 55 |
| Competitor Market Leader Novartis Animal Health Pentium Forte Plus (ILA) | Group 9 | 55 |
| Control (Saline ip) | Group 10 | 55 |

Key test parameters
622 test parr, ~25 g at vaccination
36 days acclimatization
36 days immunization FW 12C
30-50 days challenge FW 12C
PIT-tagging Number of Participants
Proposed N=55 per treatment, Estimated 550 study animals for treatments.

Main Inclusion Criteria
1. Healthy fish
2. Naive for sea water pathogens
3. Minimum weight at entry 20 g
4. Maximum weight at entry 50 g.

Main Post-Inclusion Removal (Withdrawal)
None anticipated. If mortality control group in the post vaccination period exceeds 10%, the general health of the fish can be questioned and the study should be repeated with healthy fish.

Key Activity Schedule
1. pre-vaccination and confirmation of health, including enrolment criteria (weight, appearance, physiological stage stage), Day 0.
2. vaccination procedure Day 36
3. Challenge procedure (onset) Day 70
Termination of animal phase and assessment, Day ~120.

Primary Outcome Measure
The tank is the statistical unit and all mortality data during the observation period were analyzed at the treatment level together for an overall conclusion of efficacy.

Posting of Fish and Tissues
(Use VESO confirmatory loss affirmation).
The dead fish were removed during pre-challenge (100%) and the challenge period and promptly subjected to a standard necropsy for evidence of bacterial agents. The dead fish were aseptically entered with a swab from the kidney plated on agar plates for bacteriologic evaluation (100% of the fish that die).

Outcomes
1. Mortality/Survival after cohabitation challenge with *Aeromonas salmonicida* ss *salmonicida*
2. Side effects scoring Route and Dosage Form:
Vaccine is a multivalent vaccine with oil adjuvant to be delivered by i.p. as an aid in the prevention of *A. salmonicida* and other diseases (not to be tested in this evaluation), according to the proposed label directions.

Sample Size Considerations
The study population of N=55 per treatment is in accordance with the power required for determination of statistical significance for an efficacious vaccine where the expected differentiation of vaccinated to control mortality is greater than 60%. It can also be considered to use replication in study design for fish vaccines and to allow for enough power of the test to compare the efficacy pairwise against the positive and negative references.

Protocol for Vaccine Production in Example 2:
Fresh bacterial cells of all the bacterial strains listed in Table 2 were taken from enrichment plates (blood plates for all except *Tenacibaculum* sp. for which Marine agar was used) and used for the inoculations in the different media.

Preparation of Cultures a, B, C, and D:
Tubes with following contents, 500 µl in each tube, were prepared:
  a—Physiological saline water, e.g. 0.9% NaCl
  b—Leibowitz medium (cell culture media)
  c—Blood serum from horses Bacterial cells were taken from blood plates (marine agar for *Tenacibaculum dicentrarchi*) (with 2.5% additional NaCl and mixed well into the tubes. Pre-cultures a., b. and c. were allowed to incubate for 1 to 2 hours at 10° C. Then 250 µl from each of tubes a-c were transferred as follows:

From a: 250 µl to tube A: 1000 µl LB (Luria broth) with 0.9% NaCl
From a: 250 µl to tube B: 1000 µl Leibowitz
From b: 250 µl to tube C: 1000 µl Gelatin 3.2% with 1% glucose
From c: 250 µl to tube D: 1000 µl BHI (brain heart infusion) with 1% glucose This gives a total volume of 1250 µl per tube. The cultures were then incubated five days under microaerophilic conditions.

Preparation of Culture E:
5 ml Luria broth (10 g tryptone, 5 g yeast extract, and 25 g NaCl per liter) in an erlenmeyer flask was inoculated with fresh bacteria. The cultures were incubated for four days under shaking to ensure a high $O_2$-level during incubation with addition of fresh growth medium every day during the culture period.

Preparation of Cultures F, G, and H:
Tubes with following contents, 1000 µl in each tube, were prepared:
  F—Physiological saline water, e.g. 0.9% NaCl
  G—Leibowitz (cell culture media)
  H—Blood serum from horses Bacterial cells were taken from blood plates and mixed well into the tubes. These cultures are used directly without incubation.

After preparation of the bacterial cultures A-H as disclosed above, the bacteria are inactivated with 0.6% formalin. The solution with bacterial cells and formalin was stirred in room temperature (22° C.±2° C.) in 48 hours. The cultures were then centrifuged, washed 2× and resuspended in PBS (phosphate buffered saline). After inactivation, all cultures were checked for viability to ensure that all bacterial cells are inactivated. This was performed on blood plates (Marine agar for *T. dicentrarchi*). These controls were incubated for 10 days. The vegetative cells (E) were adjusted with PBS to an OD600=1.0. The other cultures were resuspended in the volumes they are cultured in. The inactivated bacterial cultures were then stored at +4° C.

Preparation of the Vaccine:
A 1:1 volume ratio between the inactivated bacterial cultures and a FICA (Freunds Incomplete Adjuvant)/Curdlan mix was used.

The volume ratio of the different cultures in the bacterial vaccine composition was as follows:

Each protocol culture in percentage for each bacterial strain included:
  A: 10%
  B: 10%
  C: 10%
  D: 15%
  E: 40%
  F: 5%
  G: 5%
  H: 5%

Volume Ratio Adjuvant:
  Type of adjuvant
  FICA (oil) 40%
  Curdlan 60%

Curdlan:
  Concentration: 6.7 g/L

The Curdlan is not well mixed in PBS without adjusting the pH to a higher level. Both been mixing on a stirrer for an hour without adjusting the pH, and mixing on a stirrer and slowly adding NaOH till the mixture is homogenous were used. The pH is then around pH 10.5.

Mixing of the Vaccine (Bacterin and Adjuvants):
Two methods for mixing the vaccine:
  A: The syringe method is well known from before, using two 50 mL syringes with Luer-lock, connected together with a valve (ex. Discofix). This is working good when it's few types of bacterins.
  B: Mixing in high speed with a blender for 4-6 minutes. This method is the best when the vaccine is containing several types of bacterins.

The bacterial vaccine composition was a creamy homogenous emulsion, and was stored at +4° C. until use.

TABLE 2

Bacterial vaccine composition; volume in milliliter of each ingredient

| | Vaccine groups | | | | | | | |
|---|---|---|---|---|---|---|---|---|
| | Gr 1 | Gr 2 | Gr 3 | Gr 4 | Gr 5 | Gr 6 | Gr 7 | Gr 8 |
| *Ae. salm. ss salm.* | 0 | 0.3 | 0.6 | 1 | 2 | 3 | 4 | 5 |
| *M. viscosa* | 5 | 5 | 5 | 5 | 5 | 5 | 5 | 5 |
| *Al. salmonicida* | 5 | 5 | 5 | 5 | 5 | 5 | 5 | 5 |
| *V. anguillarum* | 5 | 5 | 5 | 5 | 5 | 5 | 5 | 5 |
| Total bacterins | 15 | 15.3 | 15.6 | 16 | 17 | 18 | 19 | 20 |
| Curdlan | 12 | 12 | 12 | 12 | 12 | 12 | 12 | 12 |
| Saline | 5 | 4.7 | 4.4 | 4 | 3 | 2 | 1 | 0 |
| Mineral oil | 8 | 8 | 8 | 8 | 8 | 8 | 8 | 8 |
| Total volume of vaccine | 40 | 40 | 40 | 40 | 40 | 40 | 40 | 40 |

Method Comments on Vaccine Preparation:
1. The total volume of blended inactivated bacterin and saline diluent (if added) is prepared in a test tube.
2. The total required concentration of dry weight curdlan is weighed and moistened with saline and stirred to dissolve on a magnetic stir plate with a sterile stir bar. The pH of the solution is raised from 7.2 to 11 to dissolve the curdlan and then lowered to 9 again.
3. The total volume of dissolved curdlan is added to the tube with the bacterin.
4. The total volume of oil required is added to the tube with the other contents of bacterin and curdlan.
5. Contents are transferred into a sterile blend container and emulsified at a minimum speed and for 4 minutes until a cream-like suspension is developed.
6. Contents are then transferred by sterile pipet to the glass vial or tube for experimental use.

A total of 622 Atlantic salmon parr (breed 14SaBo05-K) were weighed July 22 with an average weight of 24.1 g, vaccinated August 28 with 0.1 ml vaccine intraperitoneally and 96 non-vaccinated shedders were injected with approx. 1×10³ cfu of *A. salmonicida* ss *salmonicida* on October 2 when the average weight was 37.9 gram.

Results

The mortality among the shedders of *A. salmonicida* ss *salmonicida* in V-3445 started 5 days after intraperitoneal challenge of the shedders and 90% of the shedders were dead 9 days after challenge. The first dead fish were discovered day 11 after challenge of the shedders and the mortality started to increase in most groups on day 13 after challenge. The mortality passed 60% in the saline control group (G10) 44 days after challenge with no dead fish between day 35 and day 44 and when the trial was terminated 47 days after challenge the mortality in the negative (saline) control was 65% (FIG. 1). The mortality in the control group was expected to be closer to 80% after 35 days so the low mortality led to the decision to continue the trial longer than planned. G1 had no *A. salmonicida* ss *salmonicida* bactrin in the vaccine and also had only 23 fish instead of 55 fish as the other groups while G2 had 1.5%, G3 had 3%, G4 had 5%, G5 had 10%, G6 had 15%, G7 had 20% and G8 had 25% *A. salmonicida* ss *salmonicida* bactrin and G9 was vaccinated with a registered and marketed vaccine for Atlantic salmon with 18% bactrin from *A. salmonicida* ss *salmonicida* and with 50% mineral oil. The test vaccines G1 to G8 contained 20% mineral oil.

The test vaccines had only 40% (Culture E) of the bacterin produced with culture conditions as most registered and marketed vaccines are. The vaccine groups G6, G7, G8 and G9 were protecting best against the acute *A. salmonicida* ss *salmonicida* co-habitation challenge and there is no significant difference in protection between G9, G8 and G7. The registered and marketed vaccine used in G9 were performing somewhat better than the three others in this group of effective vaccines. Vaccine efficacy may be evaluated by measuring the relative percent survival (RPS) at the time when the mortality in the control group is passing 60%. The RPS of G9 is 82, G8 is 67, G7 is 70 and G6 is 70. The RPS of G5 is 42 and of G4 the RPS is 27 and there is a significant difference in protection between G5 and G4 and both the group of effective vaccines (G6, G7, G8, G9) and the group of ineffective vaccines (G1, G2, G3) which is not significant better than the control (G).

Discussion

The test vaccines apparently have the same need for *A. salmonicida* ss *salmonicida* antigens as the commercial vaccine to give the same level of protection. The marketed positive control vaccine G9 most probably has 18% of the bacterins from *A. salmonicida* ss *salmonicida*. The level of bacterins in the test vaccines cultured in the same way as the bacterins of the commercial positive control vaccine is 40% (Culture E) of the total level of bacterins in the test vaccines. The other 60% of the bacterins in the test vaccines are possibly protecting less efficient against acute infections. The challenge situation with a high level of *A. salmonicida* ss *salmonicida* bacteria in the water from the diseased shedder fish. The commercial vaccine is designed almost entirely to protect against furunculosis primed by a large oil component as adjuvant.

This may indicate that the total collection of bacterins of the test vaccines are more efficient in protecting against furunculosis spread from the co-habiting shedders. The test vaccines may have lost some furunculosis protection due to the lower level of oil adjuvant but gained some protection because of more optimal collection of bacterins from *A. salmonicida* ss *salmonicida* and an adjuvant that still have enough mineral oil to protect against furunculosis. A major issue in the industry has been to live with the high level of oil in the adjuvant because of the fear for reduced protection against furunculosis. The way of culturing bacterins with the novel protocol in this application may reduce the need for adding a high level of oil to the adjuvant to get a high protection against furunculosis caused by *A. salmonicida* ss *salmonicida*. The level of mineral oil can be reduced to less than half of the marketed vaccines without loss of protection against furunculosis with an important effect that the heavy side-effects of inflammation and fibrin production in the abdomen can be avoided.

Example 3: Vaccination of Atlantic Salmon Against *Moritella viscosa* Infection

*Moritella viscosa* is considered the main causative agent of the winter ulcer disease of farmed Atlantic salmon. *Aliivibrio wodanis* is a bacterium that is isolated together with *M. viscosa* in ulcers and the head kidney of Atlantic salmon with winter ulcer. *A. wodanis* has been found to a larger degree than *M. viscosa* from ulcers and organs of farmed Atlantic salmon with winter ulcer. However, *A. wodanis* has not been considered of pathogenic importance for the winter ulcer disease since it was not possible to reproduce disease in Atlantic salmon by challenging with *A. wodanis*.

*M. viscosa* and *A. wodanis* are Gram-negative gammaproteobacteria. The *Moritella* genus is a member of the family Moritellaceae, and consists of psychrophilic and barophilic species isolated from deep-sea or marine sediments. *M. viscosa* is the only currently known pathogenic member of the *Moritella* genus. *A. wodanis* belongs to the *Aliivibrio* genus of the Vibrionaceae family. Several species from this family are pathogens causing infections in marine animals.

It has, however, been demonstrated that *A. wodanis* is the major pathogen causing ulcer in farmed salmonids and in cleaner fish farmed or held in captivity. *A. wodanis* is producing a bacteriocin that is inhibiting the growth of *M. viscosa* and other fish pathogens. The bacteriocin genes are located on a plasmid in *A. wodanis*. The bacteriocin production is probably the phenomenon explaining the chronic character of many outbreaks of winter ulcer where *A. wodanis* is isolated together with *M. viscosa*. The bacteriocin system in *A. wodanis* is only activated at physiological salt conditions, i. e. at 0.9% NaCl but not at higher salt concentrations as 2.5% NaCl or similar concentrations mimicking the marine water (Hjerde E, Karlsen C, Sørum H, Parkhill J, Willassen NP, Thomson NR. Co-cultivation and transcriptome sequencing of two co-existing fish pathogens *Moritella viscosa* and *Aliivibrio wodanis*. BMC Genomics. 2015 Jun. 10; 16:447.) During the recent years it has been demonstrated that several novel bacteria are involved in ulcer development in farmed Atlantic salmon and cleaner fish. These novel bacteria are often co-infecting with *A. wodanis* and *M. viscosa* in developing ulcer both in winter and summer. *M. viscosa* is more common in ulcer outbreaks at sea temperatures below 10° C. *M. viscosa* is the only acknowledged causative ulcer pathogen besides *Tenacibaculum* species in salmonid farming. *M. viscosa* is included in the registered and marketed vaccines to prevent winter ulcer in Atlantic salmon. However, the commercial vaccines containing *M. viscosa* is not protecting fully against ulcer disease in particular during the summer period.

It is established a challenge model at VESO research facility for testing the effect of the *M. viscosa* component of batches of the registered and marketed vaccines. The model is based on a bath challenge with *M. viscosa* where the negative control should preferably reach a mortality between 60 and 80% while the mortality of the protective vaccine should stay below a level of 20 to 30%. The problem with this commonly used efficacy model is that it creates a high level of mortality in a short time and it is important to keep the challenge dose low to avoid a mortality that comes close to 100% within a short time. The model seems not to be representative for the regular outbreaks in the field of farming of Atlantic salmon since most of the outbreaks has a more protracted development with a relatively low mortality for weeks and months.

The test vaccines in the planned study was made with various combinations of bacterins from both known and novel ulcer causing bacteria made from cultures according to a protocol with various culture conditions. The level of the various bacterins in the test vaccines were unusual low compared with the level of bacterin from *M. viscosa* in the registered and marketed vaccines. The goal was also to compare the effect of intraperitoneal vaccines with immersion vaccines.

Study Title:
Efficacy of injectable and immersion vaccines against winter ulcers caused by *Moritella viscosa* in Atlantic salmon.

Date:
19 Nov. 2015

Study Objective
To evaluate the efficacy of six vaccines against *Moritella viscosa* using a water borne challenge model.

Study Schedule

TABLE 3

Study schedule

| Task | Activity | Study week | Degree days | Calendar week |
|---|---|---|---|---|
| 1 | Application to FSA | −11 | — | 46/2015 |
| 2 | Fish to 12:12 | −9 | — | 48/2015 |
| 3 | Fish to VESO Vikan | −4 | — | 53/2015 |
| 4 | PIT-tag marking 735 fish | −3 | −250 | 1/2016 |
| 5 | Fish to 24:0 | −3 | −250 | 1/2016 |
| 6 | Vaccination + scan - all groups | 0 | 0 | 4/2016 |
| 7 | Transfer to seawater | 3 | 250 | 7/2016 |
| 8 | Acclimatization to 8° C. seawater | 3-5 | 250-400+ | 4-9/2016 |

TABLE 3-continued

Study schedule

| Task | Activity | Study week | Degree days | Calendar week |
|---|---|---|---|---|
| 9 | Challenge | 5 | 400+ | 9/2016 |
| 10 | Terminate experiment | Ca. 10 | — | 14/2016 |
| 11 | Preparation of report | Ca. 14 | — | 18/2016 |

Test Facilities
VESO Vikan
Vikan
N-7810 Namsos

Study Compounds

TABLE 4

Description of investigational veterinary products.

| Vaccine | Manufacturer | Administration of vaccine | Dose (mL/fish) | Marking |
|---|---|---|---|---|
| 1 | Previwo | Immersion | 60 sec, 1/10 dilution | PIT tags |
| 2 | Previwo | Immersion | 60 sec, 1/10 dilution | PIT tags |
| 3 | Previwo | i.p. injection | 0.1 | PIT tags |
| 4 | Previwo | i.p. injection | 0.1 | PIT tags |
| 5 | Previwo | i.p. injection | 0.1 | PIT tags |
| 6 | Previwo | i.p. injection | 0.1 | PIT tags |
| 7 | Elanco | i.p. injection | 0.1 | PIT tags |

TABLE 5

Description of reference substance.

| Product | Batch number | Manufacturer | Dose (mL/fish) | Marking |
|---|---|---|---|---|
| Saline (0.9% NaCl)* | To be confirmed | Fresenius Kabi | 0.1 | PIT tags |

*produced according to S-1057.

Experimental Fish and Rearing Conditions
Experimental Fish

| Species | Atlantic salmon (*Salmo salar*) |
|---|---|
| Strain | SalmoBreed Standard |
| Origin | VESO Vikan Hatchery, N-7819 Fosslandsosen |
| Average weight | Ca. 40 g at start of smoltification program, ca. 50 g at vaccination |
| Physiological status | Smolt |
| Number of fish | 760 |

Inclusion/Exclusion (Non Inclusion) Criteria
Inclusion Criteria-Immune Status
Samples of the fish population to be used in the trial were documented by testing specific antibody activity in plasma by ELISA. Only unvaccinated fish with ELISA values within the normal range for unvaccinated fish were recruited to the trial.

Inclusion Criteria—Antigen Screening
Fish originated from broodstock that has been screened for ISAV, SPDV, PRV and IPNV by qPCR at a qualified laboratory. Samples of the fish population used in the trial were screened for ISAV, SPDV, PRV and IPNV by qPCR at a qualified laboratory appointed by VESO. Only fish from qPCR-negative fish population and qPCR-negative broodstock were recruited to the trial.

Inclusion Criteria Morphology

Only healthy, intact and sexually immature fish without apparent visual deformities or behavioural abnormalities were recruited to the trial.

Husbandry Management

The fish were acclimatized according to S-2023. The fish and tanks were tended and monitored on a daily basis according to S-2002 and S-2004. Dead fish was collected daily according to S-2000. Environmental parameters were recorded daily. Abnormal or unexpected behaviour, loss of appetite or any unexpected increase in mortality were reported to the Sponsor immediately.

| | |
|---|---|
| Salinity | Seawater |
| Stocking density | Max 20 kg/m$^3$ |
| Temperature | Immunization: 12° C. ± 1° C. |
| | Challenge: 8° C. ± 1° C. |
| Flow | Min. 0.8 L/kg/min. Adjust to min. 80% saturation in effluent water |
| Water discharge | Tube overflow system |
| Cleaning | Once a day |
| Photoperiod regime | L:D = 12:12 before and after smoltification (marking and challenge) |
| | L:D = 24:0 during smoltification (vaccination) |
| Feeding | Automatic feeders |
| Fish husbandry | Daily |
| Humane endpoint | Yes, when fish lose ability fir self-propulsion |

Study Design

Study Regulation and Compliance

The protocol is designed to comply with European Pharmacopoeia monographs:

7.2, 07/2011:0062 Vaccines for veterinary use.

7.0, 04/2013:1521 Furunculosis vaccine (inactivated, oil adjuvanted, injectable) for salmonids.

Design Summary

Eight groups of trial fish were immunised with the experimental vaccines for minimum 400 dd by immersion and intraperitoneal injection. The negative control groups are saline in oil adjuvant, saline or PBS and the positive control is Pentinum Forte Plus (Elanco). Fish were PIT-tagged min. 2 weeks prior to vaccination to facilitate recognition of trial group affiliation.

The immunized fish were challenged with *Moritella viscosa* by water borne. A water borne challenge model was chosen as this is expected to mimic a natural infection route for this disease.

The initial challenge were comprised of 95 fish per trial group-totally 760 trial and control fish.

The principal outcome parameter in the trial is mortality. A mortality rate of minimum 60% were sought.

1. Day 0 Definition

The day of vaccination is Day 0.

2. Marking

The fish were marked by PIT tag marking minimum 2 weeks before vaccination. See Table 2 and Table 3.

3. Vaccination

The fish were acclimatized for minimum one week and starved for minimum 48 hours prior to vaccination. Fish were be randomly selected, anesthetized and intraperitoneally (i.p.) injected with the vaccines or control substances according to Table 2 and Table 3. The immersion vaccines was administered as a 60 second dip, 1/10 dilution at a rate of 500 g/L diluted vaccine.

4. Challenge Procedure

1. Challenge Isolate and Challenge

*Moritella viscosa* (Jno 1016/96). The bacterium was inoculated and dose adjusted according to S-1058 and S-1087. The dose of bacterium was ca. 5×10$^5$ cfu/mL. The challenge was performed as bath challenge where the adjusted bacterial suspension was added to the challenge tank and kept for one hour.

2. Pre-Challenge

Suitable challenge doses were determined by performing a pre-challenge experiment if required.

5. Termination

The initial challenge and back-up challenge (if used) were terminated after an observation period of ca. 4-5 weeks post challenge. Time point for the termination was decided in agreement with the Sponsor. A target mortality rate of >60% is expected.

2. Sampling and Diagnostics

1. Bacteriological Examination

Bacteriological examination was performed on 100% of the fish that die before and after challenge according to S-2001.

No other samples were taken.

3. Evaluation of Test Results

1. Test Validity

The test is invalid if the specific mortality is less than 60% in the control group.

2. Calculation of Relative Percent Survival (RPS)

RPS was calculated at 60% control group mortality and at termination of the challenge according to S-1082.

4. Human Safety

Material Data Safety Sheets must be provided when potentially toxic substances and chemicals are used. The safety sheets must be read by all involved personnel and procedures must be performed according to recommendations. Substances used in the present study are listed in Table 6.

TABLE 6

| Listing of substances | |
|---|---|
| Substance | Application |
| MS222/benzocaine | Anaesthetic |
| Test vaccines | Vaccination of experimental fish |

| 5. STANDARD OPERATING PROCEDURES | |
|---|---|
| S-1007 | Vaccination of fish-intra-peritoneal injection |
| S-1008 | Vaccinaiton of fish-dip |
| S-1012 | Anaesthetisation and sedation of fish |
| S-1024 | Bath challenge |
| S-1033 | Test compounds-receipt, labelling, storage and archives |
| S-1057 | Physiological saline-preparation and storage |
| S-1058 | *Moritella viscosa*-Inoculation and dose adjustment |
| S-1082 | Calculation of relative percent survival (RPS) |
| S-1087 | Frozen inoculation doses-preparation and use |
| S-1097 | PIT tags-marking and recording |
| S-2000 | Mortality records |
| S-2001 | Bacteriological examination of fish |
| S-2002 | Feeding of fish |
| S-2004 | Daily care of fish and tanks |
| S-2013 | Disposal treatment |
| S-2023 | Trial fish-receipt, acclimatisation, documentation and treatment |

Protocol for Vaccine Production in Example 3

Fresh bacterial cells of all the bacterial strains listed in Table 2 were taken from enrichment plates (blood plates for all except *Tenacibaculum* sp for which Marine agar was used) and used for the inoculations in the different media.

Preparation of Cultures a, B, C, and D:

Tubes with following contents, 500 µl in each tube, were prepared:
- a—Physiological saline water, e.g. 0.9% NaCl
- b—Leibowitz medium (cell culture media)
- c—Blood serum from horses Bacterial cells were taken from blood plates (marine agar for *Tenacibaculum dicentrarchi*) (with 2.5% additional NaCl and mixed well into the tubes. Pre-cultures a., b. and c. were allowed to incubate for 1 to 2 hours at 10° C. Then 250 µl from each of tubes a-c were transferred as follows:

From a: 250 µl to tube A: 1000 µl LB (Luria broth) with 0.9% NaCl
From a: 250 µl to tube B: 1000 µl Leibowitz
From b: 250 µl to tube C: 1000 µl Gelatin 3.2% with 1% glucose
From c: 250 µl to tube D: 1000 µl BHI (brain heart infusion) with 1% glucose This gives a total volume of 1250 µl per tube. The cultures were then incubated five days under microaerophilic conditions.

Preparation of Culture E:

5 ml Luria broth (10 g tryptone, 5 g yeast extract, and 25 g NaCl per liter) in an erlenmeyer flask was inoculated with fresh bacteria. The cultures were incubated for four days under shaking to ensure a high $O_2$-level during incubation with addition of fresh growth medium every day during the culture period.

Preparation of Cultures F, G, and H:

Tubes with following contents, 1000 µl in each tube, were prepared:
- F—Physiological saline water, e.g. 0.9% NaCl
- G—Leibowitz (cell culture media)
- H—Blood serum from horses Bacterial cells were taken from blood plates and mixed well into the tubes. These cultures were used directly without incubation.

After preparation of the bacterial cultures A-H as disclosed above, the bacteria were inactivated with 0.6% formalin. The solution with bacterial cells and formalin was stirred in room temperature (22° C.±2° C.) in 48 hours. The cultures were then centrifuged, washed 2× and resuspended in PBS (phosphate buffered saline). After inactivation, all cultures were checked for viability to ensure that all bacterial cells were inactivated. This was performed on blood plates (Marine agar for *T. dicentrarchi*). These controls were incubated for 10 days. The vegetative cells (E) were adjusted with PBS to an OD600=1.0. The other cultures were resuspended in the volumes they were cultured in. The inactivated bacterial cultures were then stored at +4° C.

Preparation of the Vaccine:

A 1:1 volume ratio between the inactivated bacterial cultures and a FICA (Freunds Incomplete Adjuvant)/Curdlan mix was used.

The volume ratio of the different cultures in the bacterial vaccine composition was as follows:

Each protocol culture in percentage for each bacterial strain included:
- A: 10%
- B: 10%
- C: 10%
- D: 15%
- E: 60%
- F: 5%
- G: 5%
- H: 5%

Volume Ratio Adjuvant:
Type of adjuvant
FICA (oil) 40%
Curdlan 60%

Curdlan:
Concentration: 6.7 g/L

The Curdlan is not well mixed in PBS without adjusting the pH to a higher level. Both been mixing on a stirrer for an hour without adjusting the pH, and mixing on a stirrer and slowly adding NaOH till the mixture is homogenous was used. The pH is then around pH 10.5.

Mixing of the Vaccine (Bacterin and Adjuvants):

Two methods for mixing the vaccine:
- A: The syringe method is well known from before, using two 50 mL syringes with Luer-lock, connected together with a valve (ex. Discofix). This is working good when it's few types of bacterins.
- B: Mixing in high speed with a blender for 4-6 minutes. This method is the best when the vaccine is containing several types of bacterins.

The bacterial vaccine composition was a creamy homogenous emulsion, and was stored at +4° C. until use.

TABLE 7

| Bacterial vaccine composition V3559 | IP A | IP B | IP C | IP D | IMM A | IMM B | Total volume of each component as formulated |
|---|---|---|---|---|---|---|---|
| *Vibrio anguillarum*T | 2.5 | 2.5 | 2.5 | 2.5 | | | 10 |
| *Aliivibrio salmonicida* T | 2.5 | 2.5 | 2.5 | 2.5 | | | 10 |
| *Aeromonas salmonicida* ss *salmonicida* | 5 | 5 | 5 | 5 | | | 20 |
| *Moritella viscosa*T | 2.5 | 2.5 | 5 | 2.5 | 215 | 300 | 527.5 |
| *Moritella viscosa* FT | 0 | 0 | 0 | 0 | 215 | | 215 |
| *Aliivibrio wodanis*T | 2.5 | 1.25 | 2.5 | 2.5 | 215 | 200 | 423.75 |
| *Aliivibrio wodanis*FT | 1.25 | 1.25 | 2.5 | 1.25 | 215 | 150 | 371.25 |
| *Aliivibrio friggiae*T | 2.5 | 2.5 | 5 | 2.5 | 140 | 100 | 252.5 |
| *Bizionia piscinecroseptica*T | 1.25 | 0 | 0 | 1.25 | | 50 | 52.5 |
| *Aliivibrio hodis* T | 1.25 | 0 | 0 | 1.25 | | 50 | 52.5 |
| *Aliivibrio heliae* T | 1.25 | 0 | 0 | 1.25 | | 50 | 52.5 |

TABLE 7-continued

| Bacterial vaccine composition V3559 | IP A | IP B | IP C | IP D | IMM A | IMM B | Total volume of each component as formulated |
|---|---|---|---|---|---|---|---|
| *Tenacibaculum dicentrarchi* | 1.25 | 0 | 0 | 1.25 | | 50 | 52.5 |
| *Photobacterium pisciinfectiosa* T | 1.25 | 0 | 0 | 1.25 | | 50 | 52.5 |
| Saline diluent if used | 0 | 7.5 | 0 | 0 | | | 7.5 |
| Total aqueous bacterin | 25 | 25 | 25 | 25 | 1000 | 1000 | |
| Curdlan | 15 | 15 | 15 | 0 | | | 45 |
| Mineral Oil | 10 | 10 | 10 | 25 | | | 55 |
| Total Volume of Vaccine | 50 | 50 | 50 | 50 | | | |

IP A, IP B, IP C and IP D are vaccines made for intraperitoneal injection.

IMM A and IMM B are immersion vaccines.

Results

The bath challenge with a concentration approx. $5 \times 10^5$ cfu/mL of *M. viscosa* is a low challenge dose intended to keep the mortality in the negative control group between 60 and 80% after four weeks. The mortality in the control group only passed 20% after 42 days from the bath challenge and when the study was terminated 54 days from the challenge the negative control group had only reached 25% mortality (FIG. 2).

The mortality in the two immersion vaccine groups arrives 10% at day 11 after challenge while the mortality of the negative control group reaches 10% at 16-17 days. The mortality of the two groups with immersion vaccination stays 5 to 10% above the mortality in the negative control group during throughout the rest of the study.

The ip-vaccine groups have low mortalities as the negative control group or lower during the whole study.

Figure 1:
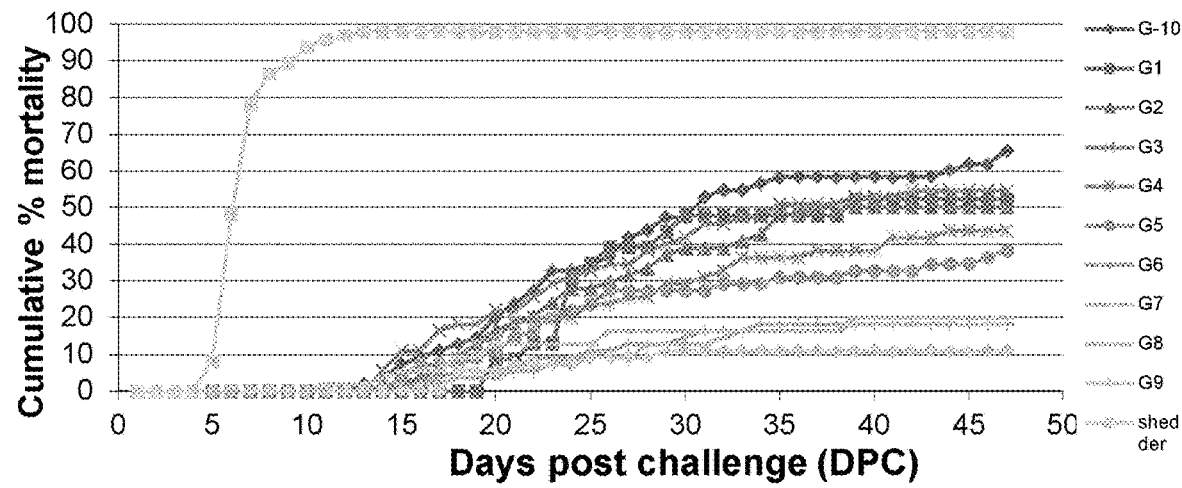
FIG. 1
Figure 2:
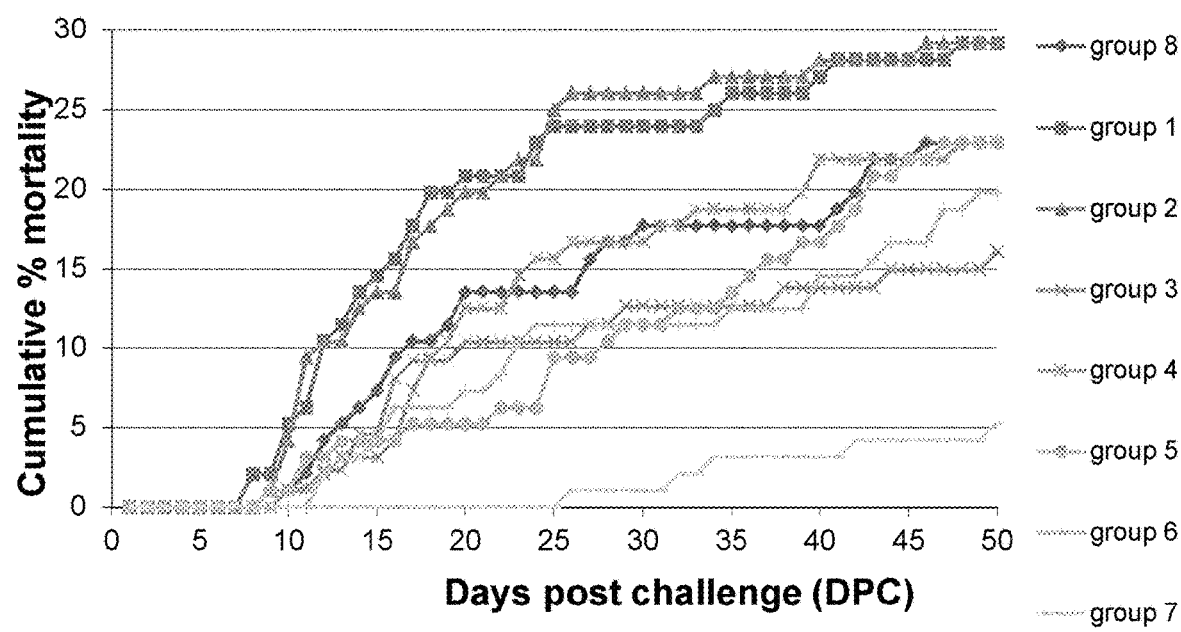

There seems to be a shift in the study three weeks after challenge (FIG. 2). The first three weeks it seems to be a dominating infection caused by the challenge pathogen *M. viscosa* while the rest of the trial seems to be dominated by other ulcer pathogens in the trial tank judged by the shift in the protection pattern between the different vaccine groups based on the bacterins in the various vaccines.

The first dead smolt in the group i.p.-vaccinated with the market leader of the registered vaccines occurred on day 26 after challenge and then increased to 5% at the end of the trial while the mortality at the end of the study varied from 18 to 31% in the other vaccine groups.

Because of the low level of morbidity compared to what was expected the smolts were stressed by reducing the water level twice with an interval of a few days.

Ulcer scoring was performed for every fish included in the trial including all fish that died from disease and all the fish that were euthanized at the end of the trial (FIGS. 3*a* and *b*). Of the 753 smolts that were scored 174 did not show any skin abnormalities (score group 3), while 159 fish showed minor changes like bleedings and oedema in the scale pockets in some areas (score group 0).

The largest group of fish consisting of 368 smolts were found with one or a few small perforating ulcers in the skin. Only 52 fish were found to have more than one large or deep ulcer perforating into the muscle layer subcutaneously.

Discussion

The V-3559 study gave a complex set of results that is dominated by the unexpected low mortality of only 14% in the saline control after 21 days and at the same time no dead smolts in the positive control group (market leader winter ulcer ip vaccine). The two best test vaccine groups had 5 and 7% mortality after three weeks from challenge.

The saline vaccine negative control group will normally have fish that are better protected against low doses of pathogens that are not included in the test vaccines compared to smolt in the vaccinated groups when they meet antigens that are not included in the vaccines. It seems that the challenge dose of $1 \times 10^5$ cfu/ml water of *M. viscosa* that usually gives a high mortality is not bringing enough infective cells of *M. viscosa* to cause an exponential mortality in the control group. One possible mechanism for this unexpected result can be that the flock immunity in the trial tank is stronger than usual because the test vaccines contain a broader variation in the bacterins from *M. viscosa* than in the registered vaccines.

The two vaccine groups with immersion vaccination were more susceptible to the *M. viscosa* challenge than the saline control even if 30% of the bacterins were produced from *M. viscosa*. The challenge dose of *M. viscosa* is relatively high and it is expected that immersion vaccines are not protecting as well as the intraperitoneal vaccines.

From the challenge date to three weeks after there seem to be a dominating infection pressure in the tank caused by *M. viscosa* as expected. However, from three weeks until 54 days at termination there seems to be additional pathogens introduced to the tank. Judged by the shifts in mortality in the different vaccine groups it seems to have been introduced bacterial pathogens that are among the novel and non-acknowledged pathogens introduced as bacterins in the IP A and IP D vaccines. The marine intake water in the VESO research facility at Vikan is UV disinfected but it is known from for instance post smolt farms with flow-through tanks with marine water on land that use of UV disinfection of the intake water does not prevent ulcer problems caused by different known pathogens as *M. viscosa* and *Tenacibaculum* bacteria. This indicates that this trial was *M. viscosa* impacted by additional pathogens after three weeks from *M. viscosa* challenge.

The IP C vaccine had 20% of the bacterins from *M. viscosa* while IP A, IP B and IP D had only 10% of the bacterins from *M. viscosa* and this may explain while IP C protects best against the acute challenge with *M. viscosa* with mortality of 5% at three weeks after challenge. The group with the market leader as positive control vaccine had no mortality three weeks after challenge. This commercial vaccine also has approximately 20% of the bacterins from *M. viscosa*. However, the bacterins are most probably made as culture E in this vaccine preparation protocol tested in this trial. In the four IP test vaccines only 60% of the bacterins is from the culture E. In addition, the high level of mineral oil in the commercial vaccine is expected to protect more effective against acute infections than the less than half amount of mineral oil in the IP test vaccines IP A, IP B and IP C. This is supported by the observation that IP D, which have FICA i.e. 100% mineral oil as adjuvant, is protecting the smolts at the same level as IP C during the first three weeks of the trial even if the level of *M. viscosa* bacterin is only half, i. e. 10%, compared to IP C. IP A and IP B is not protecting well during the three first weeks after challenge and the reason may be that these vaccines only contain 10% of the bacterins from *M. viscosa* and a low level of mineral oil in the adjuvant.

From three weeks after challenge with *M. viscosa* the diverging protection from the various vaccines used it can be indicated that ulcer pathogens other than *M. viscosa* and possibly one or more of the novel bacteria *Aliivibrio hodis, Aliivibrio heliae, Photobacterium pisciinfectiosa, Bizionia piscinecroseptica* or the known *Tenacibaculum dicentrarchi* may have got access to the research tank in spite of desinfection of the intake water. The severity of the infection or co-infection seems to be relatively low compared to the bath challenge with *M. viscosa* on the first day of the experiment. The saline control group has no additional dead fish until 27 days after challenge while the immersion vaccinated groups had a few extra dead smolts from day 24 after initial challenge with *M. viscosa*. This scenario is common in the field when it comes to mortality from ulcer disease; the disease progress is slow and lasts for weeks to months with small peaks in the mortality. The groups of smolt vaccinated with IP B and IP C that has none of the mentioned novel ulcer pathogens included as bacterins are having an increase in mortality from day 21 that is close to 10% for IP B and close to 20% for IP C both ending close to 25% total mortality compared to 8% increase in mortality for the IP A group that has novel species of ulcer bacteria included in the vaccine ending at 18% total mortality; best of the test vaccines.

The IP D vaccine group contains the same bacterin antigens as the IP A group i. e. novel ulcer pathogens but there is a difference in the adjuvant that consists of 100% mineral oil (FICA) for IP D while only 40% mineral oil and 60% curdlan as the adjuvant mix. The high level of mineral oil in the ip vaccine is known to protect better against acute infections as seen for the IP D group the first three weeks of this *M. viscosa* bath challenge study. However, when the disease is developing more chronically it is contra-productive to have a high level of oil in the adjuvant as seen for the group IP D the last couple of weeks of this study. The group vaccinated with the commercial vaccine gains a mortality of 5% during the last month of the study. This result is the best among the groups in the trial when it comes to overall mortality. However, it also demonstrates that a high level of oil that protects against acute infections from bacteria is not enough to inhibit mortality from ulcer pathogens not included in the vaccine when these novel ulcer bacteria is giving mostly chronic infections with low mortality.

Ulcer scoring was performed for every fish included in the trial including all fish that died from disease and all the fish that were euthanized at the end of the trial. Of the 753 smolts that were scored 174 (23%) had no signs of disease in the skin (score 3), 159 (21%) had small bleedings and edema in the scale pockets and raised scales and scale loss in one or more areas of the skin (score 0), 368 (49%) had one or more small perforating ulcers in the skin in addition to the signs of score 0 while 52 (7%) had one or more severe ulcers that perforated the skin and often included the underlying muscle tissue in addition to one or more of the signs in the score 0 and 1 (score 2).

The vaccine groups with the highest level of fish with no disease signs from the skin is the IMM A and IMM B that has close to one third of the fish with no disease signs in the skin. The commercial vaccine (Elanco) used as positive control for protection against *M. viscosa* challenge had only 6% of the 96 fish in the group without any symptoms from the skin. However, this was also the group that had the lowest total mortality among the vaccine groups (5%). It is interesting to compare the results from the immersion vaccine groups (IMM A and IMM B) with the results from the registered and marketed vaccine group. The immersion vaccine is taken up through the skin, gills and mouth and may protect the skin better for that reason. However, the immersion vaccine had the lowest protection against death by bacterial infection from bath challenge with *M. viscosa* among all vaccine groups while the commercial vaccine protected best against mortality. This comparison makes it relevant to indicate that the vaccine protocol used for preparing the study vaccines produces bacterins that protects better against skin infection than the classical way of making bacterins as in the commercial vaccine used in the positive control group. On the other side, the commercial vaccine seems to contain bacterins that prepare the fish to withstand the septicemic infection that easily kills the fish.

The four intraperitoneal test vaccines leave only around 20% of the smolt without skin changes caused by bacterial infections. IP B and IP C without bacterins from the novel bacterial ulcer bacteria seems to protect better against ulcer changes in the skin than IP A and IP B that contain these novel bacterins. IP C protects best against skin infection among these four IP vaccines, and it is in accordance with the level of *M. viscosa* bacterin that is twice the concentration compared to the other IP vaccines.

The ulcer distribution in the saline vaccine control is close to what is seen among the IP vaccine groups. This may indicate that the IP test vaccines produce a total immune response that is close to optimal if it is considered that unvaccinated smolts have a balanced immune system.

In conclusion, the commercial vaccine stimulates to protect better against septicemia and death, and the immersion (IMM A and IMM B) protects better against local skin infection while the ip test vaccines are producing a more balanced immune response in line with the non-vaccinated control fish.

The ulcer scoring indicates as expected that the *M. viscosa* bath challenge is the major reason for the skin changes observed in the trial tank. The bacterins from the novel fish pathogens do not seem to protect against ulcer development in this trial. However, the novel antigens protect best against mortality after week 3 of the study.

Example 4: Efficacy of Dip Vaccination of Salmo Salar Against Ulcerative Conditions in Induced and Natural Seawater Challenge Study Summary

| | |
|---|---|
| Protocol Title | Efficacy of Dip Vaccination of *Salmo salar* Against Ulcerative Conditions in Induced and Natural Sea Water Challenge abbreviated: PW006 |

-continued

| Study Summary | |
|---|---|
| Principal Investigator | Henning Sørum |
| Study Sites | Mølleveien 2, Solbergstrand, 1440 Drøbak, Norway |
| Study Activation Date | 21$^{st}$ May 2015 |
| Planned Accrual | 1200 fish divided in 2 groups of 600 fish in each |
| Duration | 194 days |
| Study Design | 1200 fish was divided in two groups (A and B) of 600 fish which will was divided in 6 subgroups of 100 fish-12 tanks in all. There were 4 immersion vaccines, one IP vaccine and 1 control group in each of the groups A and B. The vaccines were all custom made, further called "Previwo". After immunity was reached (250 atu) group A was bath challenged with *Moritella viscosa* and *Aliivibrio wodanis* at day 42. An additional IP challenge with *Aliivibrio salmonicida* was done at day 117. Group B was subjected to natural sea water challenge and artificially challenge with three different strains of *Moritella viscosa*. Due to low mortality an additional IP challenge with *Aliivibrio friggiae* was performed at day 160. |
| Study Objectives | The objective was to determine the efficacy of multivalent water-based immersion vaccines for ulcerative skin, fins and mouth conditions in vaccinated Atlantic salmon. The protected fraction was desirable to be greater than 0.50 for a claim of efficacy. |
| Inclusion Criteria | The experimental fish were unvaccinated Minimum size was 90 grams and maximum size was 130 grams. Populations entered into the study were documented to be free from exposure to the disease indications by no history of exposure to salt water before and during immunization-confirmed at source. Stocking density did not go above 40 kg/m$^3$ during the trial. |
| Exclusion Criteria | Sexually matured, injured or deformed fish or fish deemed otherwise unhealthy was excluded from the study prior to vaccination. Any more than 10% non-specific mortality during the 35-day (extended to 42 days) observation period in the untreated control population is also an exclusion criteria for the fish group. |
| Study Outcomes | Due to low mortality from ulcerative strains (from 0-6%) IP challenge with *Aliivibrio salmonicida* were performed in group A at day 117 and at day 160 for group B (i.p. challenged with *Aliivibrio friggiae*) Group A: At the end of study (day 134) no significant survival benefit over the controls could be calculated as only one fish survived in the control group. The mortality rates were VP (90.0%), V (97.8%), MVP (89.5%), MV (95.2%), multivalent IP Previwo vaccine (29.0%) and 99.0% for the control group. However-at first day with <50% dead controls (day 121 the two immersion vaccines containing alternative bacterins (VP; Culture A to H and MVP; Culture A to H except for E) and the multivalent IP Previwo vaccine showed a significantly better survival than the controls (p = 0.0056, p = 0.0059 and p < 0.0001 respectively). Further-the vaccine containing only standard cultivated strains (Culture E) showed borderline significance (p = 0.0501) vs controls. In group A the VP, MV (Culture A) and IP vaccine showed a 38.0%, 37.9% and 5.8% mortality rate respectively compared to controls with 57.7% mortality rate at the same time point. The RPS at end of study vs the controls in group A were VP 9.1%, V 1.2%, MVP 9.6%, MV 3.8% and Previwo IP vaccine 70.7%. RPS50 was VP 34.2%, V 24.7, MVP 34.4, MV 18.6 and IP Previwo vaccine 90.0%. The survival plots for group A from day of i.p. challenge with *Aliivibrio salmonicida* at day 117 showed significant p-values for all treated subgroups versus the controls. Statistical differences in mean weight of survivers at end of study were not possible to calculate between treated fish and controls due to few fish survived in the control group although all treated fish had a higher weight than the surviving fish in the control group. Mean weight of live fish at end of study in group A was 489.0 grams (MV), 396.0 grams (V), 463.5 grams (MVP), 461.5 grams (MV), 351 grams (controls, only one surviver) and 469.8 grams (IP vaccine). Mean weight in group A from challenge to end of study, all fish included not dead before challenge, showed that all the treated groups had a significantly higher mean weight than the controls. Mean weight of live fish and dead fish from challenge to end of study in group A was 410.8 grams (MV), 364.0 grams (V), 378.5 grams (MVP), 410.8 grams (MV), 299.7 grams (controls) and 449.5 grams (IP vaccine). |

Study Summary

Group B: Due to low mortality from the sea water (from 0 - 7%) an IP challenge with *Aliivibrio friggiae* was performed in group B at day 160. At end of study (day 194) no significant survival benefit over the controls could be seen. The mortality rates was VP (77.7%), V (78.8%), MVP (83.5%), MV (81.1%), multivalent IP Previwo vaccine (86.7%) and 81.2% for the control group respectively.

At the first day with <50% dead controls (day 174) no significant difference between treated fish and controls were observed.

The survival plots for group B from day of i.p. challenge with *Alliovibrio friggiae* at day 160 showed non-significant p-values for all treated subgroups versus the controls. The MVP and MV group showed borderline significance with a p-value of 0.055 and 0.06 respectively.

The RPS vs the controls in group B at end of study was VP 5.5%, V 2.9%, MVP −2.9%, MV −0.8% and Previwo IP vaccine − 6.8%. RPS50 was VP 8.9%, V 4.6%, MVP ÷ 9.0%, MV ÷ 10.7% and IP Previwo vaccine 1.0%.

Mean weight of live fish at end of study in group B was 590.3 grams (VP), 530.3 grams (V), 512.3 grams (MVP), 521.1 grams (MV), 544.5 grams and 573.8 grams (IP vaccine). None of the weights differed significantly from the controls.

Mean weight of fish in group B from challenge to end of study, all fish included but not dead fish before challenge, showed that none of the treated groups had a significantly higher mean weight than the controls except from the VP group. Mean weight of live fish and dead fish in the period from challenge to end of study in group B was 377.1 grams (MV), 381.4 grams (V), 377.1 grams (MVP), 352.7 grams (MV), 361.2 grams (controls) and 387.9 grams (IP vaccine).

Details of Example 4

Figure 4:
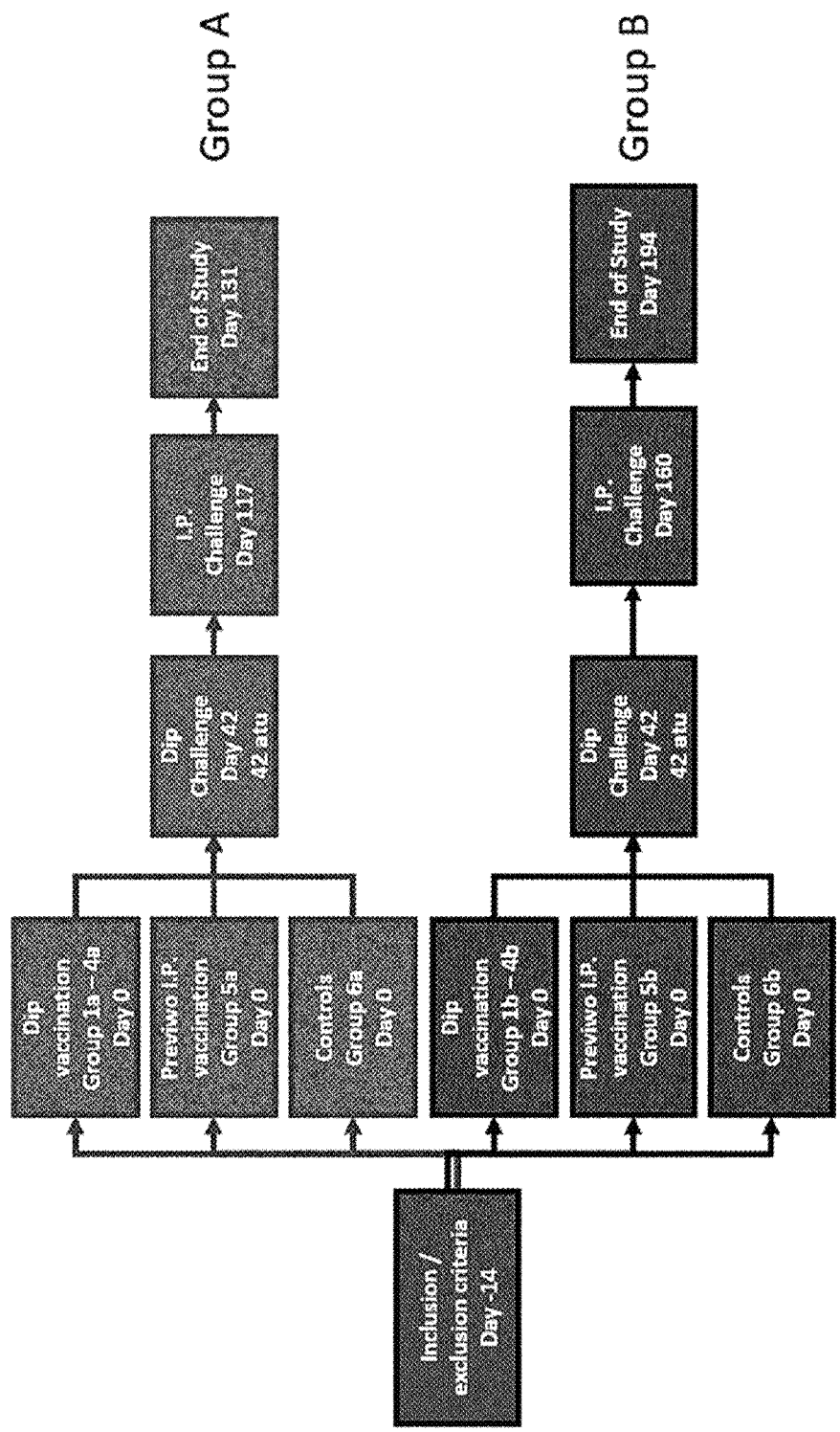

Two cohorts of salmon—A and B—with 6 groups in each cohort were vaccinated with 4 different dip vaccines, one i.p. vaccine made with the novel vaccine preparation protocol and one group in each cohort were unvaccinated controls. After an immunization period of 42 days cohort A was bath challenged with the ulcerative strains *M. viscosa* and *Aliivibrio wodanis* strains (FIG. 4).

Winter ulcer a recurrent problem to the aquaculture industry in Scotland, Iceland, Faroe Islands, Ireland, Canada, Maine in USA and Norway.

Immersion vaccines have been used with success for classical bacterial infections such as *Vibrio* spp and *Yersina ruckeri*, and provide a good protection within a period of six months and are typically used to vaccinate small fish of 1-5 grams. This gives relatively good protection (50-60% RPS) until they are big enough to receive an injection vaccination.

One of the limitations of immersion vaccination are that the immunity does not last over a sufficient period and a booster vaccination is required when the exposure to the infectious agent continues over a longer period. Further, the method has been thought to be impractical for larger size fish due to cost-effectiveness and the stress that could be induced by vaccination unless delivered by bath vaccination at lower dilution for an extended period of time. The fact that there are not available immersion vaccines for all bacterial strains that may cause or be a part of the disease development also make it interesting to make a vaccine that target these bacterial species. It should be taken into consideration that in fish smaller than 1 g, the immune system might still be immature and the vaccine efficacy may be reduced.

A range of bacteria were included in the vaccine (Table 8a) together with morphological different bacterial forms (Table 8b). Each species was produced under varying aerophilic conditions in order to produce the variation in bacterins as is closely described in the PW006 protocol. It was anticipated that vaccines including the various antigenic forms would give additional protection.

In this study the efficacy of several immersion vaccines by dip administration was tested against ulcerative conditions in smolt up to 4 months and 40-70 grams following sea transfer. If immersion vaccines could be shown to provide immunogenicity, they could hold a high value as a smolt transfer vaccine and function also as a primer for an injectable vaccine to be given after the immersion vaccine.

The protocol used in Example 4 aimed to determine the efficacy of multivalent water-based immersion vaccines for ulcerative skin, fins and mouth conditions in vaccinated Atlantic salmon. The results will serve as proof of concept that immersion delivery can result in a sufficient immune response tested at 420 atu (Accumulated Thermal Units) post-vaccination. The protected fraction was desired to be greater than 0.50 for a claim of efficacy. A separate vaccinated group was vaccinated by the injectable Previwo vaccine intraperitoneally to compare the expected stronger effect of this vaccine to the immersion-vaccinated groups.

The inactivated bacteria used as immunogens in this trial were bacteria known to induce winter ulcers in salmon included all the classical strains of bacterin of vibrios and *Aeromonas salmonicida* subspecies *salmonicida* (Table 8a). Seven bacterin forms (Culture A to H minus Culture E) of each bacterium were also grown in addition to the classical (Culture E) form (8b).

TABLE 8a

List of inactivated bacterial strains used in the dip vaccine

| Strain No. | Bacterial Strains in vaccines |
|---|---|
| S1 | *Aliivibrio wodanis* T NCIMB 13582 |
| S3 | *Moritella viscosa* T NCIMB 13584 |

TABLE 8a-continued

List of inactivated bacterial strains used in the dip vaccine

| Strain No. | Bacterial Strains in vaccines |
|---|---|
| S5 | *Aliivibrio friggiae*T NCIMB 42181T |
| S6 | *Aliivibrio heliae*T NCIMB 42953T |
| S7 | *Bizionia piscinecroseptica*T NCIMB 42181T |
| S8 | *Aliivibrio salmonicida*T NCIMB 2262T |
| S9 | *Vibrio anguillarum*T ATCC 14181T |
| S10 | *Aeromonas salmonicida* ss *salmonicida* 1282/94 |
| S11 | *Photobacterium* sp. |
| S14 | *Tenacibaculum* sp. 1-15 L |
| S15 | *Vibrio hodis*T NCIMB 42952T |
| S16 | *Aliivibrio wodanis*T NCIMB 42121 |

Four immersion vaccines were made by a combination of classically grown bacteria with or without alternatively grown bacteria (Table 8b) grown under normal- or microaerophilic conditions. All bacteria were produced separately and in four lots. The first lot produced a combination of classical exponential grown bacteria and alternatively grown bacteria, the second lot resulted in a majority of traditional bacterins. The third and fourth lot contained combination of the same bacterins as lots 1 and 2 but were grown under microaerophilic conditions. The amounts of bacterins were 1:11 solution in the final vaccine (50% bacterins and 50% water/emulsion).

TABLE 8b

| Strains in Immersion vaccine | % bacterin |
|---|---|
| *Moritella viscosa*$^T$ | 30 |
| *Aliivibrio wodanis*$^T$ | 20 |
| *Aliivibrio wodanis*$^{FT}$ | 15 |
| *Aliivibrio friggiae*$^T$ | 10 |
| *Bizionia piscinecroseptica*$^T$ | 5 |
| *Aliivibrio hodis*$^T$ | 5 |
| *Aliivibrio heliae*$^T$ | 5 |
| *Tenacibaculum* sp. | 5 |
| *Photobacterium* sp. | 5 |

Formulation of dip vaccine. Acute strains not included in order to reach threshold values for bacterin of auxiliary strains.

TABLE 9

Vaccine groups, challenge form, water quality and number of fish

| Vaccine | Vaccine Group | Challenge | Water and # | Total No. Fish |
|---|---|---|---|---|
| Vaccine 1 | Veg + Post (VP) | Dip, n = 100 | Seawater, n = 100 | 200 |
| Vaccine 2 | Veg − Post (V) | Dip, n = 100 | Seawater, n = 100 | 200 |
| Vaccine 3 | Mic + Post (MVP) | Dip, n = 100 | Seawater, n = 100 | 200 |
| Vaccine 4 | Mic − Post (MV) | Dip, n = 100 | Seawater, n = 100 | 200 |
| Vaccine 5 | Previwo i.p. | Dip, n = 100 | Seawater, n = 100 | 200 |
| No vaccine | Treat as dip gr. | Dip, n = 100 | Seawater, n = 100 | 200 |
| Total | | 600 | 600 | 1200 |

Vaccine 1, 3 and 5 contained alternative bacterins (Post; Culture A to H minus E) in addition to the classical bacterins (Veg; Culture E).

Vaccine VP consists of Culture A to H
Vaccine V consists of Culture E
Vaccine MVP consists of Culture A to H except E
Vaccine MV consists of Culture A Vaccination and challenge: Fish in group 1a-4a and 1b-4b were dip vaccinated in fresh water for 30 seconds before transported to a group (a and b) specific tank were the fish in both tanks were kept for 42-43 days before challenge by bath (A) or natural seawater (B). The fish that were i.p. vaccinated in the two groups did not go through the dip vaccination procedure (FIG. 4).

Results

Group A—Induced Challenge

Fish were kept in tanks for 42 days for immunization and monitored on a daily basis. After an initial immunization period fish in group A were bath challenged with the ulcerative strains *Moritella viscosa* and *Aliivibrio wodanis*. At day 117 fish were i.p. challenged with *Aliivibrio salmonicida* (Table 8a above).

All dead fish were collected on a daily basis during the study and cause of death confirmed. Biopsies were taken from all fish with ulcers, dead during the study and alive at end of study, in order to confirm strain of bacteria leading to ulcers and/or death.

The two bath vaccinated groups containing alternative bacterins (Culture A to H minus E) and the IP all showed a higher survival rate than the controls at end of study. However—due to the high mortality in the control group $X^2$ values could not be calculated.

TABLE 10

Group A End of study (day 131)

| Group | Vaccine | Total n EoS$^1$ | Dead at EoS | % dead | RPS | Chi$^2$ p-value vs ctrl |
|---|---|---|---|---|---|---|
| 1 | VP | 100 | 90 | 90.0 | 9.1% | NA |
| 2 | V | 92 | 90 | 97.8 | 12% | NA |
| 3 | MVP | 95 | 85 | 89.5 | 9.6% | NA |
| 4 | MV | 83 | 79 | 95.2 | 3.8% | NA |
| 5 | Previwo ip | 69 | 20 | 29.0 | 70.7% | NA |
| 6 | Controls$^4$ | 97 | 96 | 99.0 | — | — |

*Mortality rates Group A at end of study (day 131). Dip challenged with *Moritella viscosa* and *Aliivibrio wodanis* after 42 days and i.p. challenged with *Aliivibrio salmonicida* 75 days later. MV = Veg + Post. V = Veg − Post. MVP = Microaerophilic + Post. MV = Microaerophilic − Post.
*No values can be calculated for comparison with the controls as only one value is available.

After day 75 mortality from the tested challenge strains were low and in order to increase mortality additional challenges were performed. All surviving fish were IP challenged with *A. salmonicida* which increased mortality significantly. The first day the mortality reached more than 50% (58%) for the controls was day 79 after first bath challenge (121 days after start of study).

One hundred fish were allocated to each of the six subgroups in group A. However—some fish in each group died during the immunization period due to circumstances not related to the vaccination (some died from hypoxia during tank transfer, some jumped out of the tank etc). In addition, some fish were hard to group as colour and clipping fades over time.

At the end of the study a total of 64 of 600 fish were missing/unclassifiable due to difficulties reading the group markings.

Looking at the relative percent survival it can be seen that the Previwo I.P. vaccine had 70.7% while the four bath vaccines all has RPS below 50% (Table 10).

TABLE 11

Group A-Weight of live fish at end of study (day 131)

| Treatment | Weight (gram) | Weight gain vs. controls | % weight gain | Chi$^2$ p-value vs ctrl |
|---|---|---|---|---|
| VP | 489.0 | 138.0 | 39.3 | NA |
| V | 396.0 | 45.0 | 12.8 | NA |
| MVP | 463.5 | 112.5 | 32. | NA |
| MV | 461.5 | 110.5 | 31.5 | NA |
| i.p. | 469.8 | 118.8 | 33.8 | NA |
| Controls* | 351.0 | — | — | — |

VP: Veg including Post,
V: Veg no Post,
MVP: Microaerophilic including Post,
MV: Microaerophilic no Post,
I.P, Previwo i.p. vaccine.
*Until end of study at day 131 only one surviving fish. No statistics can be calculated from less than 5.

Figure 5:
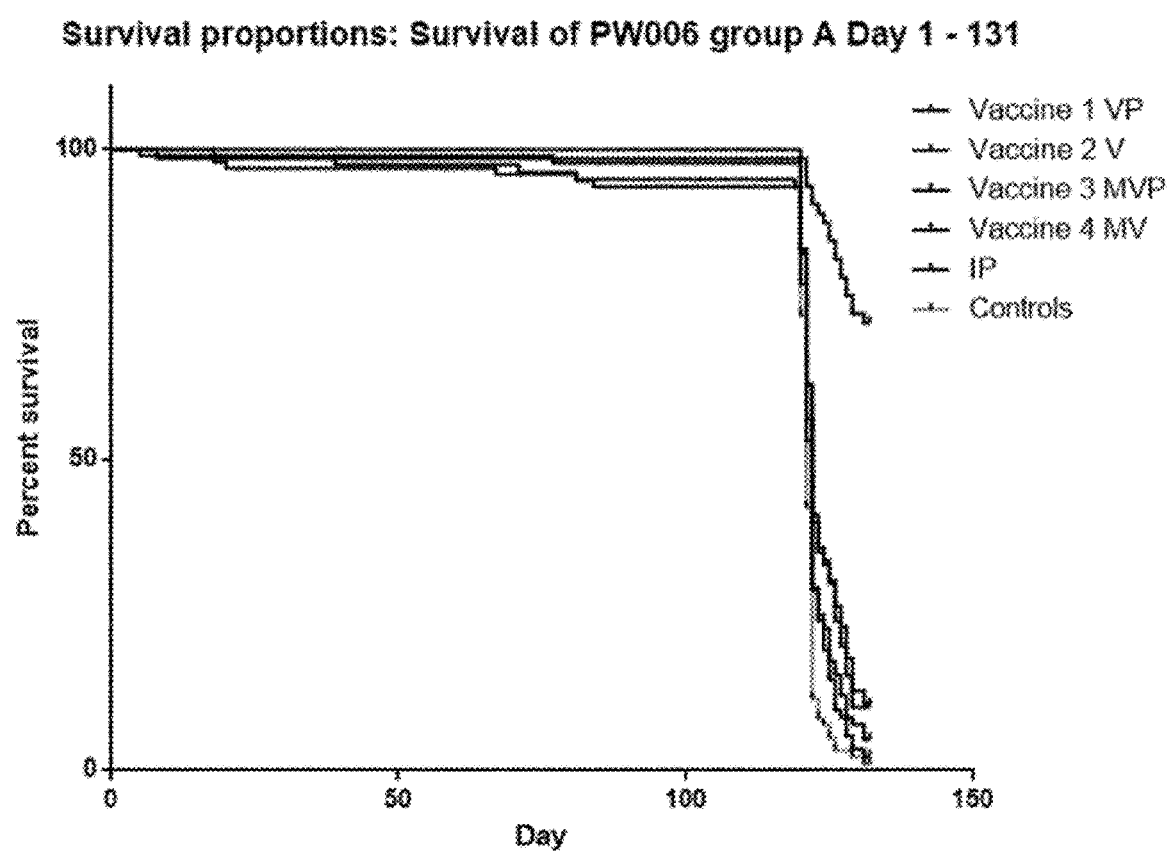

Looking at the survival curves after IP challenge with *Aliivibrio salmonicida* at day 117 a high mortality can be observed (FIG. 5). The IP vaccine performs very well and the survival in this group is 73.1% vs controls at 1.0% (Table 12). The two best performing dip vaccines were the two vaccines containing alternative bacterins (VP and MVP) which had a survival rate of 10.6% and 10.5% respectively. The classical and microaerophilic cultured vaccines showed a survival rate of 5.1% and 3.3%.

From the survival curves it can be observed that the controls show a more rapid mortality rate after 5 days than especially the i.p. vaccine but also all the bath vaccines in general (FIG. 5).

TABLE 12

Group A - survival curves comparison (day 117-131)

| Group A | p-value vs controls | Day 117 | Day 131 | Per cent survivers From Day 134 | RPS |
|---|---|---|---|---|---|
| VP | <0.0001 | 94 | 10 | 10.6% | 9.1% |
| V | 0.0023 | 90 | 3 | 3.3% | 1.2% |
| MVP | <0.0001 | 95 | 10 | 10.5% | 9.6% |
| MV | 0.0051 | 79 | 4 | 5.1% | 3.8% |
| i.p.vaccine | <0.0001 | 67 | 49 | 73.1% | 70.7% |
| Controls | NA | 97 | 1 | 1.0% | — |

Data shown for survival curves after i.p. challenge at day 117, and until day 131 (end of study).

Figure 6:
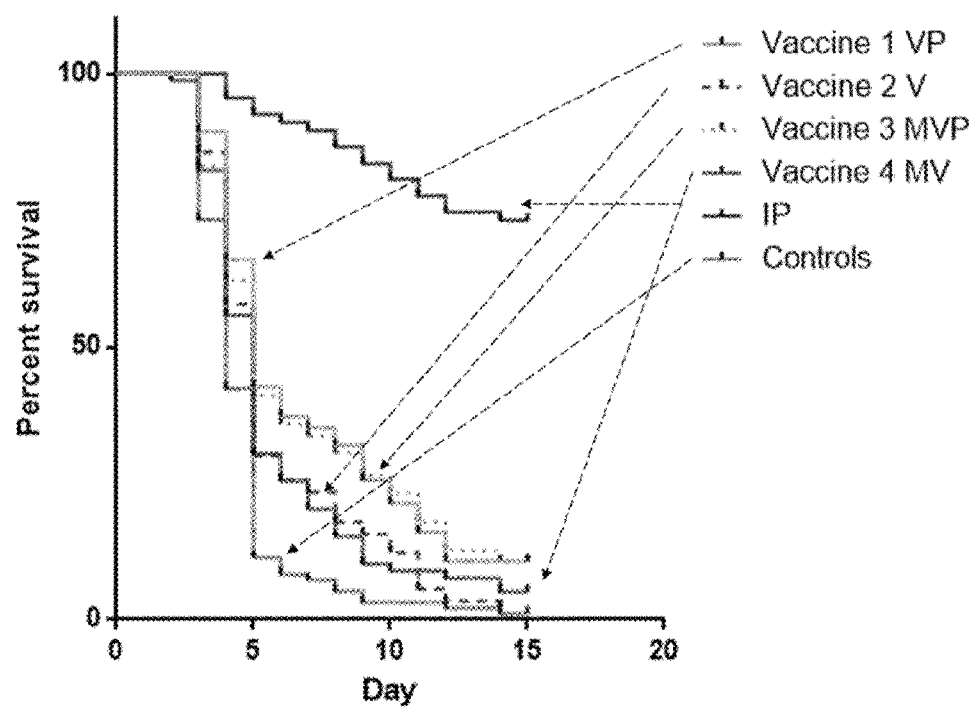

Comparing the relative percent survival between subgroups in group A shows that groups treated with vaccines containing alternative bacterins did significantly better than vaccines containing classical bacterins only (Table 8b) in the survival plot (FIGS. 5 and 6).

Results showed that the intraperitoneally vaccinated fish had a significantly higher relative percent survival (RPS) over the 132 days than both controls and dip vaccinated fish (Table 12). RPS for dip vaccinated fish did also show a significantly higher RPS than the controls.

RPS=1-( )

Despite the fact that the first challenge did not induce the expected mortality it is a high probability that the challenge had an impact on the immune system of the fish which in turn made fish more susceptible for mortality by the second challenge. Most of the fish had bleedings in the skin under the abdomen indicating that most of the salmon had subclinical infections from the bath challenge at day 42.

TABLE 13

Group A—RPS50 mortality data at 58% dead controls (day 122).

| Group | Vaccine | Total n EOS$^1$ | Dead | % dead | RPS | Chi$^2$ p-value vs controls |
|---|---|---|---|---|---|---|
| 1 | VP | 100 | 38 | 38.0 | 34.2% | 0.0056 |
| 2 | V | 92 | 40 | 43.5 | 24.7% | 0.0501 |
| 3 | MVP | 95 | 36 | 37.9 | 34.4% | 0.0059 |
| 4 | MV | 83 | 39 | 47.0 | 18.6% | 0.1501 |
| 5 | i.p. | 69 | 4 | 5.8 | 90.0% | <0.0001 |
| 6 | Contrs$^4$ | 97 | 56 | 57.7 | — | — |

Mortality rates Group A at 58% dead control fish at day 122 of the study (day 4 after IP challenge). Dip challenged with *Moritella viscosa* and *Aliivibrio wodanis* after 42 days and i.p. challenged with *Aliivibrio salmonicida* 75 days later. MV=Veg+Post, V=Veg−Post, MVP=Microaerophilic+Post, MV=Microaerophilic−Post.

TABLE 14

Group A - Weight of live fish at end of study.

| Treatment | Weight (gram) |
|---|---|
| VP | 414.0 |
| V | 362.9 |
| MVP | 364.6 |
| MV | 400.4 |
| i.p. vaccine | 415.0 |
| Controls | 302.6* |

*Only one fish survived in the control group which do not allow statistic calculations.
VP: Veg including alternative bacterins,
V: Veg no alternative bactgerins,
MVP: Microaerophilic including alternative bacterins.
MV: Microaerophilic no alternative bacterins,
I.P. Previwo i.p. vaccine In addition to survival mean weight of the fish differed significantly between all treated groups and the controls at end of study.

TABLE 15

Group A - Weight of all fish dead and a live from IP challenge to end of study.

| Treatment | Weight (gram) | p-value |
|---|---|---|
| VP | 421.5 | <0.0001 |
| V | 364.0 | 0.0005 |
| MVP | 378.5 | <0.0001 |
| MV | 410.8 | <0.0001 |
| i.p. vaccine | 449.5 | 0.0001 |
| Controls | 299.7 | NA |

VP: Veg including alternative bacterins,
V: Veg no alternative bacterins,
MVP: Microaerophilic including alternative bacterins.
MV: Microaerophilic no alternative bacterins,
I.P. Previwo i.p. vaccine
Weight of all groups compared to mean absolute weight of controls.

It is anticipated that the weight of the fish has changed marginally between the different groups over the 15 days from challenge to end of study. Looking at the weight of the fish dead over this period in combination with the fish live at end of study the results show that the IP vaccinated fish have the highest absolute mean weight (449.5 grams) while the VP vaccine as second highest absolute mean weight (421.5 grams). Worst off are the controls (299.7 grams). All mean weights in the treated fish groups turns out to be significantly higher than the mean weight of the control fish.

Group B—Seawater Challenge

Figure 7:
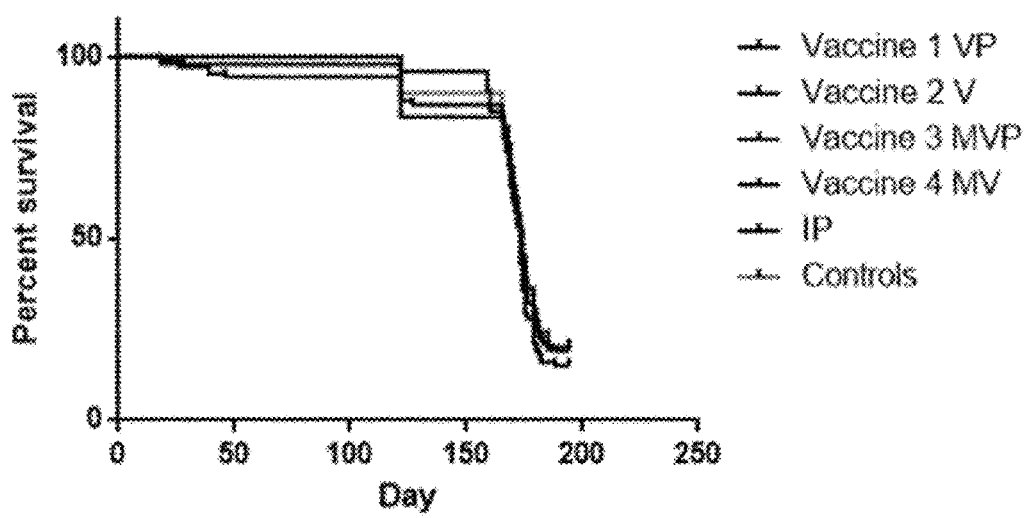
Figure 8:
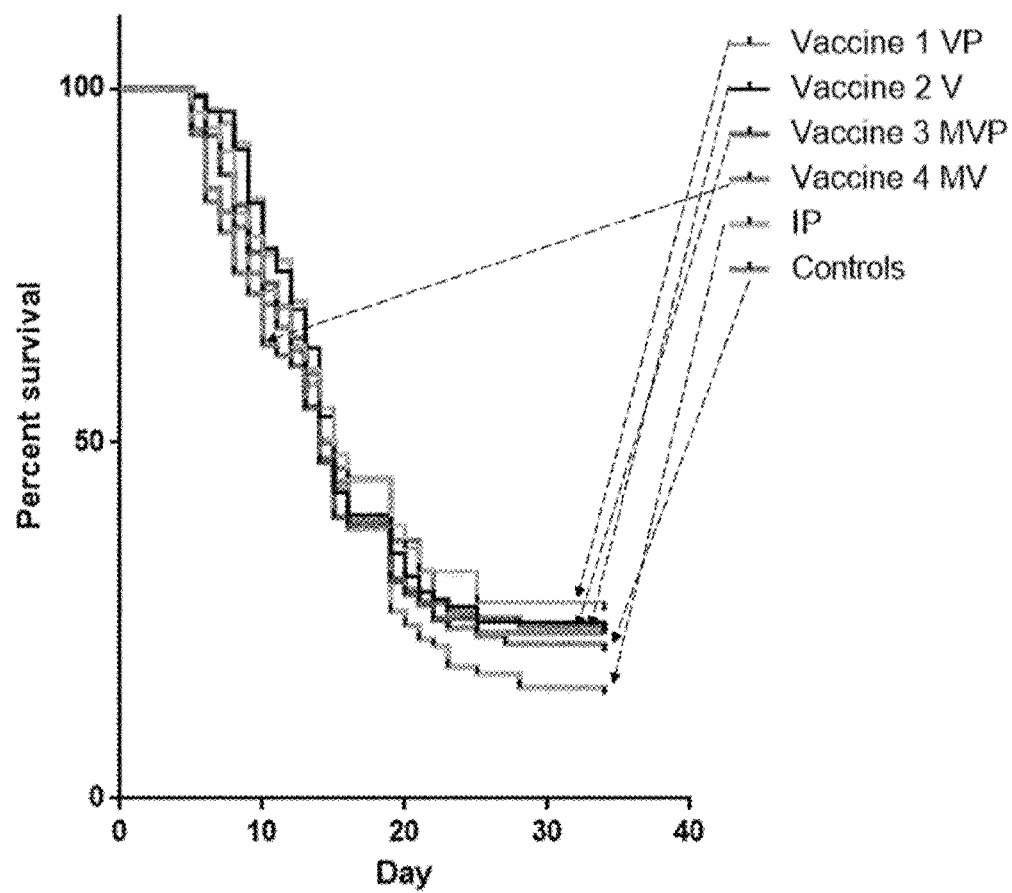

Fished were kept in tanks for 43 days for immunization and monitored on a daily basis and 16 fish died from unspecific causes. After the initial immunization period fish in group B were challenged with natural sea water without added pathogens. However, it is expected some low mortality 5 to 10% during the three to four months after sea launch. A very low mortality was observed (3 fish) from the sea water challenge in the period of 74 days after sea launch and it was decided that group B also should be subjected to artificial challenge with a bath with 3 different strain of *Moritella viscosa* in order to increase mortality at day 117 (FIGS. 7 and 8). After 5 days an increase in mortality were observed (40 fish) only to stop again the next day and a low mortality were observed the next 38 days. At day 160 it was decided to i.p. challenge the remaining fish with *Aliivibrio friggiae* in order to increase mortality. This challenge was successful and at day 174 it was observed a mortality of 55% among the control fish.

TABLE 16

Total mortality rates Group B at day 194.

| Group | Vaccine | Total n EOS[1] | Dead at EOS | % dead | RPS | Chi$^2$ p-value vs controls |
|---|---|---|---|---|---|---|
| 1 | VP | 103 | 79 | 23.3 | 5.5% | 0.432 |
| 2 | V | 104 | 82 | 21.2 | 2.9% | 0.675 |
| 3 | MVP | 91 | 76 | 16.5 | −2.9% | 0.673 |
| 4 | MV | 88 | 72 | 18.2 | −0.8% | 0.911 |
| 5 | i.p. | 113 | 98 | 13.3 | −6.8% | 0.269 |
| 6 | Contr | 101 | 92 | 18.1 | — | — |

Dip challenged with three strains of *Moritella viscosa* at day 117 and i.p. challenged with *Aliivibrio* friggiae at day 160. None of the treated groups showed a significant survival compared to controls at end of study (day 194).

All dead fish were collected on a daily basis during the study and cause of death confirmed. Biopsies were taken from all fish with ulcers, dead during the study and alive at end of study, in order to confirm strain of bacteria leading to ulcers and/or death. At the end of the study a total of 600 fish were accounted for. However—the number in each group varied somewhat from the planned 100 (Table 16 above). This is most likely due to errors from reading of markings on the fish or a small miscalculation at start of study.

TABLE 17

Mortality data at 55% dead controls in group B day 174.

| Group | Vaccine | Total n EOS[1] | Dead | % dead | RPS | Chi$^2$ p-value vs controls |
|---|---|---|---|---|---|---|
| 1 | VP | 103 | 52 | 50.5% | 8.9% | 0.4777 |
| 2 | V | 104 | 55 | 52.9% | 4.6% | 0.7129 |
| 3 | MVP | 91 | 55 | 60.4% | −9.0% | 0.4839 |
| 4 | MV | 88 | 54 | 61.4% | −10.7% | 0.4105 |
| 5 | i.p. | 113 | 62 | 54.9% | 1.0% | 0.9323 |
| 6 | Contr[4] | 101 | 56 | 55.4% | — | — |

Mortality rates Group B at 55% dead control fish at day 174. None of the treated groups showed a significant survival compared to controls at end of study (day 194).

At end of study weight for all surviving fish were captured. Numbers show that none of the treated groups had a significant weight gain compared to controls (Table 19).

TABLE 18

Survival data group B

| Group | Group B | Alive at Day 160 | Alive at Day 194 | Per cent survivers | p-value vs controls Survival curve | Chi$^2$ p-value vs controls |
|---|---|---|---|---|---|---|
| 1 | VP | 92 | 24 | 26.1% | ns | 0.949 |
| 2 | V | 92 | 22 | 23.9% | ns | 0.525 |
| 3 | MVP | 85 | 15 | 17.7% | ns | 0.055 |
| 4 | MV | 70 | 16 | 14.3% | ns | 0.060 |
| 5 | i.p. vaccine | 102 | 15 | 14.7% | ns | 0.138 |
| 6 | Controls | 91 | 19 | 20.9% | — | NA |

No added survival benefit for groups vaccinated in cohort B was observed when tested by survival curves or Chi2.

TABLE 19

Group B* - Weight of live fish at day 194.

| Treatment | Weight (grams) | Weight gain vs. controls (grams) | Weight gain vs controls (%) | Chi$^2$ p-value |
|---|---|---|---|---|
| VP | 590.3 | 45.8 | 8.4% | 0.449 |
| V | 530.3 | −14.2 | −2.6% | 0.809 |
| MVP | 512.3 | −32.2 | −5.9% | 0.582 |
| MV* | 521.1 | −23.4 | −4.3% | 0.704 |
| I.P. | 576.8 | 29.3 | 5.4% | 0.652 |
| Controls | 544.5 | — | — | — |

*18 fish - missing weights for 4 fish

After weighing the surviving fish at end of study no difference could be observed between treated fish and controls in group B.

It is anticipated that the weight of the fish has changed somewhat between the different groups over the 35 days from challenge to end of study but believe that as the majority of the fish were alive at the day of IP challenge the weight would still give a good representation of the status of the fish over this time.

TABLE 20

Group B - Weight of all fish dead and alive from IP challenge to end of study.

| Treatment | Weight (gram) | p-value |
|---|---|---|
| VP | 407.2 | 0.0420 |
| V | 381.4 | 0.3713 |
| MVP | 377.1 | 0.4758 |
| MV | 352.7 | 0.6949 |
| i.p. vaccine | 387.9 | 0.1793 |
| Controls | 361.2 | NA |

VP: Veg including alternative bacterins, V: Veg no alternative bacterins, MVP: Microaerophilic including alternative bacterins. MV: Microaerophilic no alternative bacterins, I.P. Previwo i.p. vaccine.

Weight of all groups compared to mean absolute weight of controls.

Looking at the weight of the fish dead over this period in combination with the fish live at end of study the results show that the VP vaccinated fish have the highest absolute mean weight (407.2 grams) with the IP vaccine as second highest absolute mean weight (387.9 grams). Worst off is the MV group (352.7 grams) although it was not significantly lower than the controls. Only the VP group turned out to have a significantly higher mean weight than the controls.

Discussion

At the end of study number of control fish in group A was only one which put some restrictions on what statistics to use. The results were also influenced by the fact that the bath challenge models did not work as effectively as intended, and the i.p. challenge done later in the study proved to give a very rapid mortality. As the groups were challenged multiple times and with more than one bacterium the information from this trial will give a more general view of the efficacy of the vaccines against the bacteria used in the challenge and not all strains in the vaccines.

However—although the i.p. challenge at the end of study in group A proved to be very effective, data at first day of more than 50% dead controls (58%) show a significant survival benefit for the two groups containing Culture A to H except E (MV and MVP). These two groups showed an RPS of 34% over the controls. The Previwo i.p. vaccine performed well and had a 90.0% RPS over the controls at day 122, which show a very good effect of the IP vaccine. Though—the good effect of the IP vaccine might also partly be due to a general effect of the vaccination treatment per se, as any vaccination with an adjuvant without bacterins are known to activate the immune system to some degree.

The survival curves in group A also show a significant difference between the different treatments where all groups perform better than the controls. An effect of the bacterins from Culture A to H except H may also be attributed to the two vaccines containing these. It should be noted however, that the protection from vaccination is limited probably because the intense challenge pressure from the i.p. injected *Aliivibrio salmonicida*. The effect of the dip vaccination was not sufficient to claim efficacy compared to controls. This is in part due to the fact that the challenge as described in the protocol did not turn out with as dead fish as anticipated which made it necessary to introduce more dip challenges and at the end also i.p. challenge in order to observe a high mortality. These were different for group A and B. This makes comparing the groups A and B not expedient. The single surviving fish in the control group in cohort A also made any comparison of weight gain unattainable. However—if mean weights from challenge to end of study is compared to the control group it is found that that all groups perform better than the controls. It is reasonable to anticipate that the weight gain difference would be very limited for the fish over the short period of 15 days. The differences in weight gain between the different vaccine groups from sea launch to end of the study 131 days later were considerable in the favor of the vaccinated groups in Tank A. The ip-vaccinated fish had 50% larger weight than the control fish after 131 days in sea water. The two dip vaccinated groups with the best weight gain had 41% (VP; Culture A to H) and 37% (MV; Culture A) better growth in the study period of 131 days in sea water compared to the control group. The two other dip vaccinated groups had 26% (MVP; Culture A to H except E) and 21% (V; Culture E) better growth than the control group.

In tank B—which was first challenged with natural sea water—a sufficient number of control fish survived to support statistical analysis. However—none of the treated groups showed superior survival effect of the vaccines at end of study or at first day of dead controls over 50%. Neither it was observed any significant differences when looking at the survival curves. It is hard to draw any firm conclusion to why no differences could be observed as in group A, but it might that the vaccines do not protect sufficiently against the challenge regime done in group B.

The weight of the treated fish was not shown to be significantly higher than the controls at the end of the study in group B although some had a gain in weight. However— if mean weights from start of challenge to end of study is compared to the controls it is found that the VP (Culture A to H) group performs significantly better than the controls with 13% more weight gain than the control fish during the study period of 194 days.

The results from this study was clouded by the fact that the challenge models were hard to implement successfully as these are still under development. No such models are currently available for chronic ulcerative conditions causing long term incremental deaths for the cohort, and until such challenges are available, proof of efficacy for the immersion vaccine(s) may have to be verified under natural field condition where the multiplex of infectious materials can be used to differentiate treatment effect. However, there is reason to believe that the bath challenge at Day 42 in Tank A with *M. viscosa* and *A. wodanis* may have created a sub-clinical infection that have made the immune system to fight against the infection for 75 days. The bleedings discovered on the ventral skin of the salmon in Tank A at the end of study suggest such a subclinical infection caused by *M. viscosa* and *A. wodanis*. The salmon in Tank B did not have bleedings in the skin to the same extent even if the fish in this tank was bath challenged at Day 117. Before Day 117 Tank B had got only natural sea water to measure how the test vaccines were able to protect against the regular infections coming with the sea water that often cause a low level of mortality caused by skin ulcers and fin rot. The level of pathogens seemed to be low in the sea water and therefore it was decided to bath challenge with *M. viscosa*. In the long period with low pathogen levels in the water the vaccines are not so necessary as during infectious pressure and the fish can grow well even without vaccines as was demonstrated by the control fish. It is also a cost to be vaccinated and this is demonstrated by three of the dip vaccine groups that were gaining some less weight than the control fish.

Conclusion

By looking at the survival curves in cohort A, it can be seen that all treatment groups differ significantly from the control group. It can be concluded that proof the immunogenicity of the delivery route via bath administration was observed and that at least in the Cohort group A, a significant protection was observed at 50% mortality point vs the control group after IP challenge for all vaccine treatment groups. This was also apparent if mean weight of the fish in cohort A were compared to the controls in the period from first day of challenge to end of study.

This survival benefit was however not observed in cohort B neither at end of study or at first day <50% of control fish had died. The weight did not differ between most groups and the controls so it can not be concluded that a weight gain vs controls for this cohort at end of study or from challenge to end of study is present.

The effect of dip vaccination is not optimally tested by ip challenge 3 months or so later, the high level of infectious agents easily overrun the protection compared to intraperitoneal vaccination.

The study demonstrates a strong link between chronic bacterial infections and growth which underlines that it is important to control chronic infections not only to reduce the loss of fish but more so to avoid reduction in growth and weight gain. The novel vaccine protocol can be used to produce bacterial antigens that prevent chronic ulcer disease and increase growth in farmed Atlantic salmon in the sea.

Example 5: Vaccination of Dogs Against Skin Infections Caused by *Staphylococcus Pseudintermedius*

Vaccination of dogs against skin infections caused by *Staphylococcus pseudintermedius*.

The dog has been kept by the human being as an animal for companion and assistance for thousands of years. After centuries of breeding more than 250 different breeds of dogs have been developed. The various breeds vary in size from a couple of kilograms to the size of an adult person. The anatomy and functionality of the different dog breeds vary extensively.

The mammals have similar diseases between most of the species.

Infections in the skin caused by staphylococcal bacteria is common among the various dog breeds. Among the different animal species treated in veterinary medicine the dog is the most important companion animal. One third of all veterinary medical diagnoses in dogs is connected to diseases in the skin and the most important bacterium connected to infections in the skin is *Staphylococcus pseudintermedius*. *S. pseudintermedius* is the most important staphylococcal pathogen of the dog as *Staphylococcus aureus* is the most important staphylococcal pathogen of the human species. The different diseases caused by staphylococci in various mammals are connected to all organs of the body but the skin and skin-related organs as the ear and mammary gland are far the most important locations for diseases caused by staphylococci.

Deep infections in the skin of dogs are given the name "furunculosis" because nodules of infected tissue develops and often opens to the surface as small abscessa. These infections are almost always caused by *S. pseudintermedius*. Furunculosis develops into chronically serious infections involving relatively large areas of the skin on the head, under the abdomen and on the feet especially between the toes of all four legs. Furunculosis has for more than 60 years been controlled with antibiotics. The last decades cephalosporins have been most extensively used to control furunculosis and other related skin infections. The effect of the antibiotics is relatively slow and the dogs need to use antibiotics for three to five weeks to control the deep infections in a way that the dog is relieved for the symptoms of the infection.

Commonly the infection relapses typically a couple of weeks after termination of the antibiotic treatment. The disease develops again in a few weeks into the same extent as before the antibiotic treatment and the affected dog needs a repeated antibiotic cure. The furunculosis dogs often needs three to five antibiotic cures per year for several years for the rest of their life. The result is development of antibiotic multi-resistance in *S. pseudintermedius* strains in the different diseased dogs and also among *S. pseudintermedius* in general in the various dog populations globally. Methicillin resistant *S. pseudintermedius* strains have evolved in many countries and they are called MRSP as methicillin resistant *Staphylococcus aureus* in humans are called MRSA.

Furunculosis and more superficial infections in the skin of dogs caused by *S. pseudintermedius* may start when the dog is a puppy of a few months or it may develop when the dog is from one to five years old. Often these dogs also have ear infections caused by *S. pseudintermedius*. The ear infections may also establish in young age and continue throughout the life of the dogs. The ear infections are also most commonly treated by applying antibiotics locally into the ears. The effect is also often short with the need of repeated treatments.

There is no registered and marketed vaccines against skin infections caused by *S. pseudintermedius*. Autovaccines made by the use of the *S. pseudintermedius* strain of the particular diseased dog in making a vaccine for the single dog individually have been made for some decades without a clear good effect. The effect of autovaccines may vary from dog to dog and the duration may also vary and in all cases the infection is not controlled permanently and use of antibiotics or another autovaccine is almost invariably necessary.

A common medical treatment in dogs with skin infections caused by *S. pseudintermedius* is the use of corticosteroids systemically for periods of weeks to reduce the symptoms of the infection in the skin. The use of corticosteroids is an emergency treatment to reduce the acute symptoms that often reduces the animal welfare of the dog extensively.

The symptoms include local swelling and redness in the skin. After weeks and months the diseased skin develops nodules that are painful and larger areas of the skin are developing every sign of a classical infection which increases the dogs' need to lick and scratch because of an itching in the skin. The most severely affected dogs are after some years of ineffective treatment euthanized because of animal welfare reasons and to end the need of extensive labor related to the inefficient treatment strategies.

Study Objective

The intention of the study was to demonstrate that the novel vaccination protocol could control the various types of skin disease in dogs caused by *S. pseudintermedius*.

Study Population

Three dogs with symptoms of chronic skin infection caused by *S. pseudintermedius* were selected in 2014 for testing the novel vaccine development protocol.

Dog 1 was a female boxer with deep furunculosis on the head and on the feet that started to develop when the dog had passed five years of age. Dog 2 where a male German shepherd dog with deep furunculosis under the abdomen and on the legs and feet since the dog was two years of age. The German shepherd dog where trained as a professional dog in the army and had a high value for his service. Dog 3 was an intermediate sized mixed breed that had a severe superficial infection in the skin mostly on the abdomen causing a red itching skin. The causative strain of the superficial skin infection of Dog 3 where multi-resistant to all relevant antibiotics and the dog where considered for euthanisation.

In December 2018 three English bulldog males with deep furunculosis in the skin of the mandibula and on the feet where vaccinated with a vaccine produced according to the same novel vaccine protocol as used in 2014 to vaccinate Dog 1, 2 and 3. One of the three English bulldogs, Dog 4, two year old, had a chronic furunculosis caused by an MRSP and the owner considered to have his dog euthanized due to the risk of transferring the MRSP to human medical patients since the owner had his profession related to a hospital as a health worker.

Dog 5, two years old, and Dog 6, seven years old, were both living in the same family. The dog owner was worried of transferring *S. pseudintermedius* to her old family member that she visited in an elderly home frequently. The owner of the two dogs was also worried about possible transfer of *S. pseudintermedius* to other patients in the elderly home she visited with the dogs since the elderly people petted the dogs a lot and they wanted her to bring her two dogs when at visit.

Methods

Vaccine Preparation in Example 5

For Dog 1, 2 and 3 three different vaccine batches were made from an individual isolate of *S. pseudintermedius* isolated from each of the three separate dogs making the vaccines per definition autovaccines. For Dog 4, 5 and 6 the *S. pseudintermedius* of dog 5 was used to make a common vaccine batch for all three of the dogs.

The vaccine protocol described in Example 1 of this application was used in making all four test batches of the vaccine containing *S. pseudintermedius* bacterins and the ratio of mixing the cultures A to H were the following: A 10%, B 10%, C 10%, D 10%, E 40%, F 5%, G 5% and H 5%. The adjuvant added to all four vaccine batches made were identically mixed as 60% of curdlan and 40% of FICA as mineral oil.

Vaccination of Dogs

All six dogs were injected with 1.0 ml of the test vaccine subcutaneously dorsally on the neck and for Dog 1, 2 and 3 a second dose of 0.8 ml of the same vaccine batch as used the first time was injected in the same area of the neck four weeks after the first injection of vaccine.

It was developing an inflammation subcutaneously at the site of vaccination after the second vaccination for Dog 1 and 2 and for Dogs 4 and 5 after the first vaccination dose. Dog 4 and 5 were given a three day-regimen of tablets containing non-steroid anti-inflammatory drug (NSAID, Metacam®) from day 4 after vaccination to reduce the edema and the size of the inflamed subcutaneous tissue that were between 5 to 10 cm in diameter. The inflamed tissue was being reduced in size in all dogs showing this type of reaction from 10 days after vaccination independent of the treatment with NSAIDS or not.

Results

All six dogs demonstrated improvements in the clinical condition starting from three to four days after the first vaccination doses were administered to the dogs. The improvement of the clinical condition in the dogs with deep furunculosis continued to develop through the three months after the primary vaccine dose.

Dog 1, the female boxer had clearly reduced itching in the skin from four days after the first vaccine dose was given 24 Jul. 2014. Dog 4 the English bulldog with MRSP infection demonstrated less intense inflammation in the skin on the mandibula from the third day after vaccination. During the first week after the first vaccine dose was given the intensity of the inflammation in the infected skin was reduced with less redness in the skin and with a reduced size of the nodules of the skin were seen. In the second week after vaccination the nodules in the skin typically was reduced in size but an opening in the skin on top of the nodule often developed with protrusion of a somewhat light viscous liquid with a grey to light pink colour. After being emptied for this viscous grey liquid, the opening were closed for some days before it opened again emptying even more of the same liquid. This could go on for a few weeks while the nodule was reduced in size and finally the skin in the area developed a normal structure with hair starting to grow and the area could be defined as healthy.

The grey and light pink viscous liquid that came from the skin nodules was not seen from the abscessa before vaccination. Before vaccination the abscessa typically could become open with a more yellowish puss that was followed by a serum-like liquid for a couple of days and the nodule was not reduced in size and typically was painful when touched or handle. After vaccination the nodules became painless and the dogs did not react when the pustules where pressed by fingers to squeeze out the viscous contents.

The grey-pink viscous contents of the healing nodules or abscessa where found to contain a large amount of immune cells typically with macrophages/monocytes as half of the cell population while the other half of the cells where neutrophil granulocytes as judged by staining the cells and observing them in a microscope. The macrophages contained a large amounts of bacterial cells while the neutrophils did not contain visible remnants of bacterial cells inside the cells.

From the third month after vaccination Dog 1 and 2 developed typically one or maybe two swellings subcutaneously on the legs or on the back mostly in areas without earlier skin symptoms. These swellings were painless and without any irritation to the dog and they slowly retarded and the skin turned normal again after some weeks. These nodules also contained the same viscous grey liquid as from the healing pustules. Microscopically they also represented the same cells also with many bacterial structures intracellular in the macrophages. Possibly these liquid containing swellings is a novel side-effect from the novel vaccine used. Theoretically the "cold-abscessa" seen represent "artificial lymph nodes" because a large number of immune cells in the skin start to attract each other instead of travelling directly to the lymph nodus draining the area of infection in the skin. The veterinarian routinely following the army service German shepherd probably misjudged the appearance of the novel "cold-abscessa" that appeared on the legs of Dog 2 as more malignant to the dog than what was the case and for this and also of irrelevant reasons euthanized Dog 2 about 8 months after the first vaccine dose was given. This veterinarian was not properly informed on the use of the novel vaccine and believed the dog developed into a new different and serious stage of the furunculosis disease even if the symptoms of furunculosis had disappeared at the time of when the dog was euthanized.

The lymph nodes of all the vaccinated dogs whatever age of the animal became larger and more swollen compared to what was observed prior to the vaccination. This enlarged active lymph nodes became permanent for the rest of the observed period after vaccination.

Dog 3 became completely rid of the superficial skin infection within a few weeks after the first vaccine were administered and had no symptoms at the revaccination after four weeks. The dog owner has only reported a healthy dog after the vaccination of Dog 3.

Dog 1, Belle, the female boxer, became almost completely free of symptoms of skin infection after three months, the skin normalized and the chronic outer ear infection in both ears also terminated within the same period. The dog did not need any form of extra medication due to skin or ear infection after the vaccination with *S. pseudintermedius* bacterins made by using the novel vaccine protocol. In periods of stress as caused by heat periods or mental stress the symptoms of superficial infection of the skin could reappear for less than a week but always disappeared without the need of treatment. This indicates that the vaccine is not helping the dog to get rid of the *S. pseudintermedius* pathogen from the skin tissue. However, the vaccine with the novel bacterins is making the immune system of the dog able to control the infection actively and efficient. Dog 1 was euthanized at the age of nine years due to a heart valve infection caused by *S. pseudintermedius*, probably the same strain as was causing the skin infection. During three and a half year after infection Dog 1 had no need for treatment against skin and ear infection and was considered fully healthy without symptoms from the skin and ears. Dog 1 was considered for being euthanized at the time of vaccination due to three years of serious furunculosis infection. The vaccination was in other words giving Dog 1 a life-long control of the S. pseudintermedius infection of the skin and ears. However, it cannot be excluded that the heart valve infection by S. pseudintermedius can be considered as a result of an increased risk of the vaccination against furunculosis because a shift in the immune protection towards a more intense activity in the skin.

Figure 9:
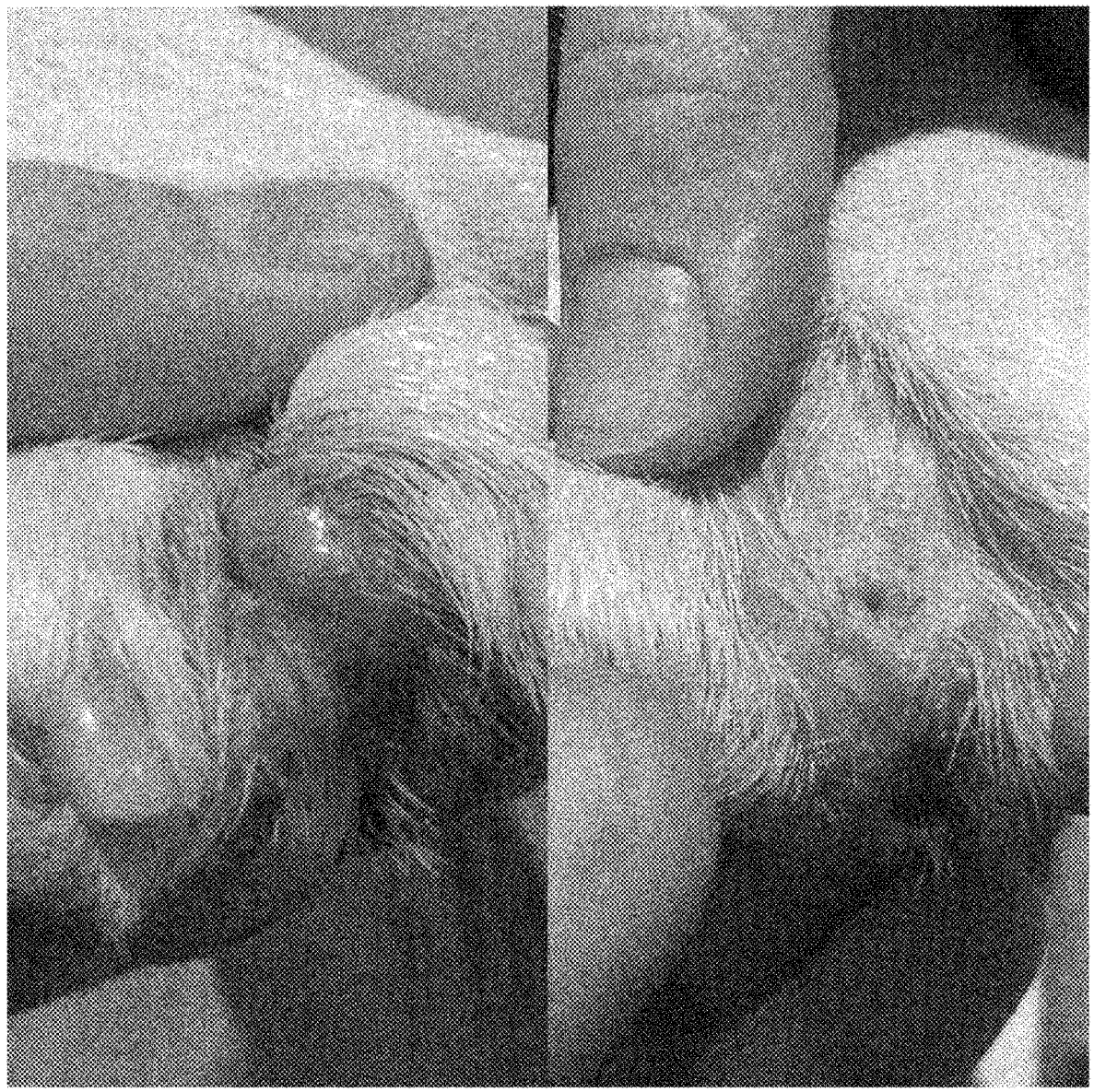
Figure 10:
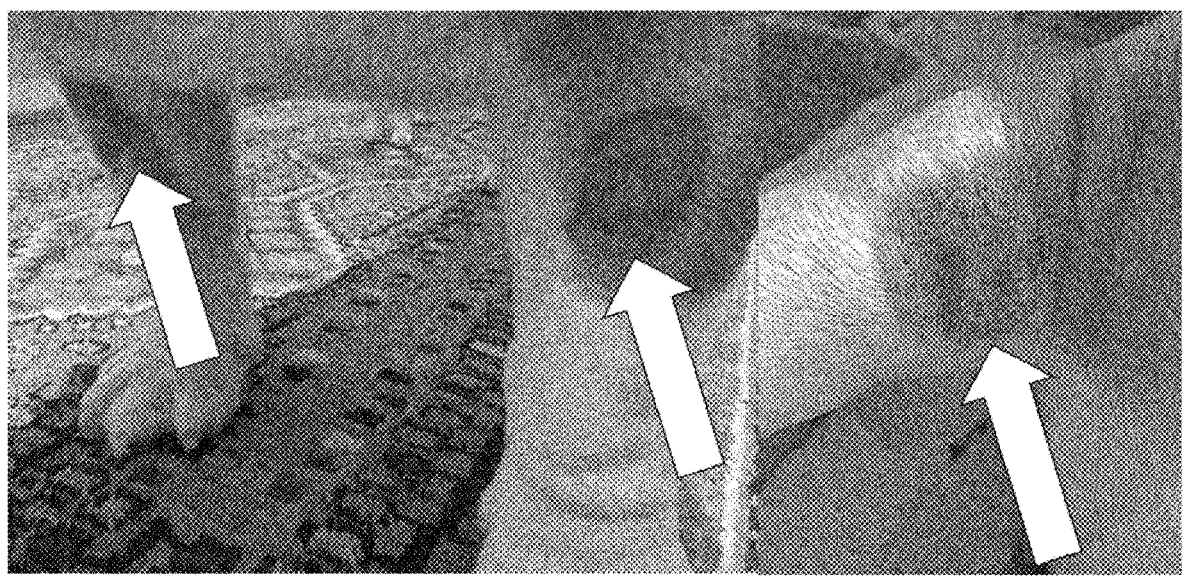
Figure 11:
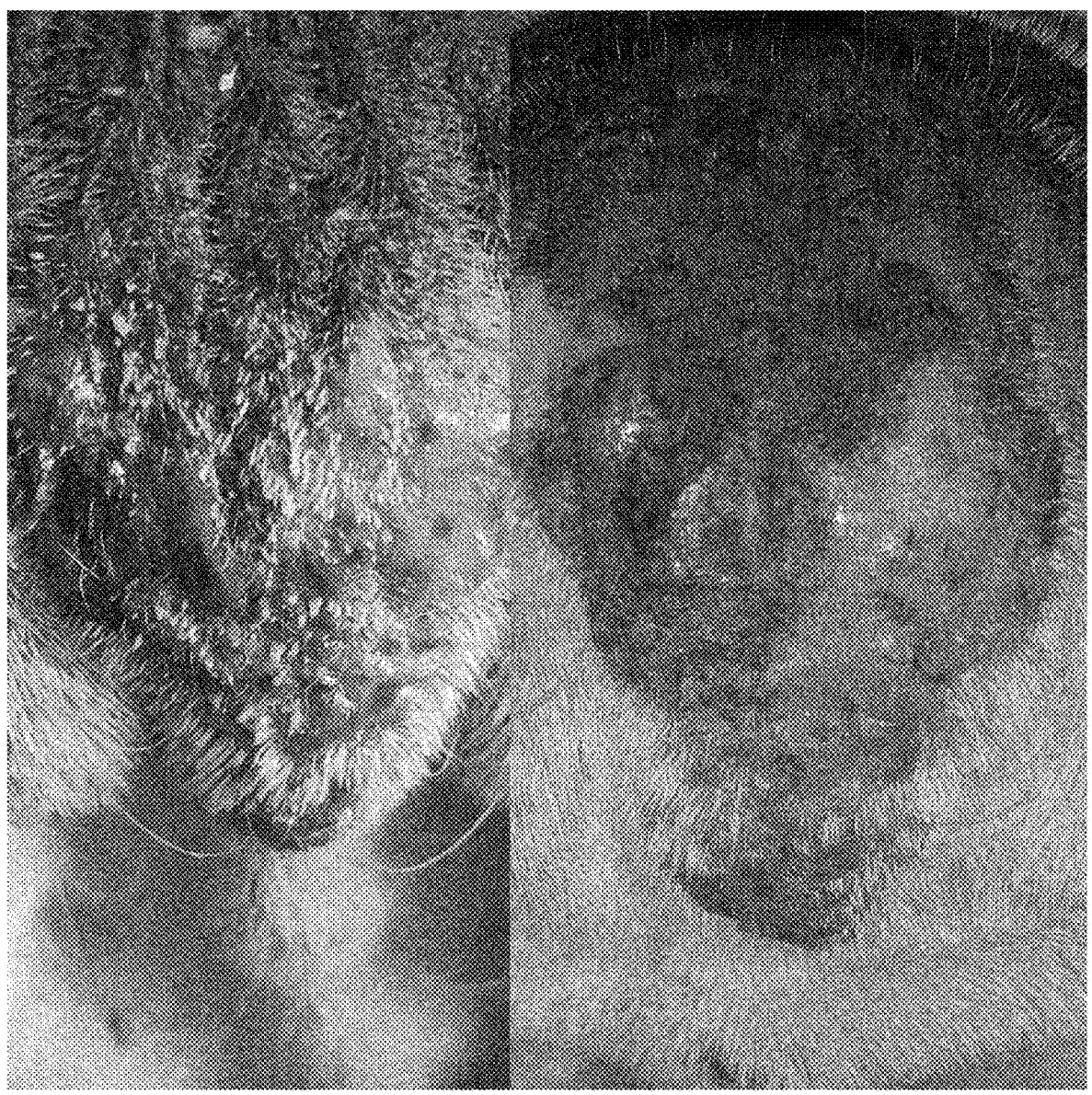

Dog 4, 5 and 6 all male English bulldogs with deep furunculosis and ear infections are all demonstrating the same improvement as Dog 1 and 2 after a period of two weeks after the first vaccine dose was given (FIGS. 9, 10 and 11). Dog 4 developed an abscess on the injection site for the vaccine after 10 weeks. The abscess self-drained after 6 weeks and after 6 months from vaccination there were no signs of abscess or scar tissue at the injection site. The reason for development of an abscess in dog 4 was speculated to be that some of the vaccine dose was injected into the muscle tissue in the neck. All three English bulldogs (Dog 4, 5 and 6) were having periods of weak symptoms from skin infections in periods of one to two weeks before symptoms disappeared during the first 6 months after vaccination. Dog 4, 5 and 6 were only given one dose of vaccine while Dog 1, 2 and 3 were given a booster dose after 3 to 4 weeks. After 7 months we tested if a short 7-day oral treatment with cephalexin (Keflex®) could have a beneficial effect for dogs 5 and 6 reducing the remaining 10 to 20% level of symptoms that appeared in periods after the first vaccine dose was given. The effect of cephalexin was clear after a few days and all weak remaining symptoms disappeared for several weeks after the short period of using cephalexin orally. Dog 5 and 6 have been have only had minimal symptoms of skin infection after the short antibiotic treatment at 7 months after vaccination and up to one year after vaccination with one single dose of vaccine.

Dog 4 were infected with a strain of MRSP and therefore a second dose of 1 ml of the same vaccine as used for the first vaccination 10 months earlier was administered subcutaneously on the neck at a site 10 cm away from the injection site of the first vaccine dose 10 months after the first dose was given to evaluate if a revaccination could reduce the low level of symptoms that could persist for one to two weeks periodically as with Dogs 5 and 6. The vaccine had been stored at +4° C. Also at revaccination Dog 4 developed an abscess at the injection site. The development, maturation and healing of the abscess went at approximately half of the time compared to after the first vaccine dose were given. Dog 4 has been without clinical symptoms after revaccination and has stopped licking his paws as he did in periods after the first vaccine dose was given. The owner observes that the welfare of Dog 4 has increased even more after the revaccination related to "happiness, energy, activity and appetite for feed".

Discussion

The novel vaccine protocol in which the cultures A to H were made according to the various steps of the protocol and subsequently combined into a mix of bacterins from Staphylococcus pseudintermedius is verified to be an effective tool for controlling all variants of infections in the skin and skin-related organs of the dog caused by S. pseudintermedius. The vaccine can typically be used as a therapeutic vaccine to stop chronic serious infections in the skin or skin-related organs. However, there is reason to believe that other infections caused by S. pseudintermedius in the dog like joint infection, osteomyelitis, secondary infection in surgery wounds et cetera can be cured by administering the vaccine prepared according to the novel protocol. It is also reason to believe that vaccines made against staphylococci according to the novel protocol can be used as a preventive tool as most vaccines today are used.

It is also reason to believe that the novel vaccine protocol can be used for preparing effective therapeutic vaccines in other animal species typically mammals and birds including the human being.

The dramatic benefits of the novel vaccine protocol will probably be large reductions in antibiotic usage to companion animals as typically dogs in veterinary medicine in the future. This will reduce the development of antibiotic resistance in the veterinary medicine in general. The same trend will potentially be seen in human medicine when the novel vaccine protocol is developed for producing effective vaccines against staphylococci in human medicine.

As per today there is still no good protocol to prepare guaranteed effective vaccines against bacterial infections either acute or chronic. The only efficient vaccines made against bacterial diseases are made by formalin inactivated toxins so called toxoid vaccines against diphtheria, tetanus et cetera where the main virulence factors are toxins.

Example 6—Vaccination Against Sarcoidosis in Horses

The horse species is the animal that has contributed most to the development of the human society. Still the designation "horse power" is the most used description unit of the energy needed in all transportation vehicles used for both goods and people. The need of controlling diseases related to castration of stallions for the armed forces was one of factors that led to an economic funding of the first school of veterinary medicine in Lyon, France in 1761 by Claude Bourgelat. Before a specific veterinary education was established the doctors treated both humans and animals when needed.

The horse has many parallel diseases to other mammalian species. The horse as the human being are rarely suffering from a chronically developing disease called sarcoidosis. Sarcoidosis has no known cause either in horses, other species or humans. Sarcoidosis is a disease with typically a cutaneous form and a lung form. In the horse the cutaneous form is the most common and appears as nodules in the skin that develops into neoplastic tissue developing from the connective tissue subcutaneously. The development is relatively slow and sometimes the neoplastic changes can disappear after some months or years without any treatment. However, most commonly the neoplastic development becomes large and may involve larger areas of the skin and the subcutaneous tissue inhibiting the activity of the horse either for its movement or for the use of saddle or other equipment needed for riding or traction of wagons et cetera.

The neoplastic tissue can be removed surgically but invariably small infiltrations of neoplastic tissue remaining in the surgery area develop into re-occurring neoplastic tissue with a high level of growth. This regrowth makes the situation worse than it was before surgery within a few weeks and it is not considered a good option for treatment. Different treatments have been tested against cutaneous sarcoidosis in horses and a protocol which includes vaccination of the affected horse with some of the neoplastic tissue removed from the affected area of the skin has been demonstrated to be effective in most cases. The protocol involves freezing of a few $cm^3$ of neoplastic tissue in liquid nitrogen and then applying the frozen tissue subcutaneous on the side of the neck. This "vaccination" procedure makes the immune system of the horse to react against the neoplastic tissue and subsequently up to 70% of the horses treated get rid of the cutaneous sarcoidosis.

Study Objective

There has been indicated that cutaneous sarcoidosis in horses may be caused by a herpes virus since the virus has been repeatedly isolated from neoplastic tissue from horses with sarcoidosis. The intention of this study was to test if bacteria isolated from the neoplastic tissue could be fully or partially responsible for development of the neoplastic tissue in the sarcoid disease in horses.

Study Population

Two horses with cutaneous sarcoidosis was selected for testing the novel vaccine protocol.

Horse 1 was a 13 year old mare, New Forest riding pony, Danica, with sarcoidosis on the medial side of left hind leg close to the abdomen. Horse 2, a 9 year old mare of Norwegian heavy breed, with cutaneous sarcoidosis in the front between the two legs under the breast muscles.

Methods

A 10 cm$^3$ piece of neoplastic tissue was surgically removed from both Horse 1 and 2. Bacterial growth was screened for by inoculating from several sterile made sections of the surgically removed neoplastic tissue of the two horses. From Horse 1 it was found growth of the bacterium *Staphylococcus aureus* from several of the inoculations from the tissue. From the neoplastic tissue removed from Horse 2 it was in the same way found repeated growth on blood agar plates of the bacterium *Streptococcus equi* subspecies *zooepidemicus*.

The novel vaccine protocol was applied in making bacterins from culture A to H by involving a *Staphylococcus aureus* isolated from the neoplastic tissue of Horse 1 and a strain of *Streptococcus equi* subspecies *zooepidemicus* from Horse 2.

The mixture of the bacterins of cultures A to H made according to the novel protocol from *S. aureus* from Horse 1 and *Streptococcus equi* subspecies *zooepidemicus* from Horse 2 was according to the alternative 1 in the Experiment 1 i. e. in the ratio of mixing the cultures A to H were the following A 8.6%, B 8.6%, C 8.6%, D 8.6%, E 40%, F 8.6%, G 8.6% and H 8.6% The adjuvant added to both vaccine batches made were identically mixed as 60% of curdlan and 40% of FICA as mineral oil.

Horse 1 and Horse 2 were injected 1.5 ml of vaccine subcutaneously on the left side of the neck and revaccinated after four weeks. When Horse 2 was re-vaccinated with the *S. equi* ss *zooepidemicus* bacterins an area of inflammation around the site of vaccination developed and within 10 hours after the re-vaccination the horse got stiff in the neck and developed fever. The horse was given NSAIDS and the symptoms revealed within the next day.

Results

Figure 12:

Both Horse 1 and Horse 2 were monitored carefully for development of the neoplastic tissue for six months. In both horses the development of neoplastic nodules stopped completely for most of the neoplastic tissue existing on the time of vaccination (FIG. 12).

After two to three months some of the small nodules in the skin started to develop and in total the vaccine may have stopped and slowed down the neoplastic development of the existing neoplastic tissue. However, there is reason to believe that additional factors may act together with the bacteria in the tissues with cutaneous sarcoidosis at an early stage of the disease.

Discussion

Cutaneous sarcoidosis in horses may have different bacterial causative agents as an important part of the pathogenesis. The vaccination of Horse 1 and 2 with bacterins from *Staphylococcus aureus* and *Streptococcus equi* subspecies *zooepidemicus* isolated from the neoplastic tissue of the patient seems to have a therapeutic impact that can be used in the future control of sarcoidosis. The novel protocol of preparing antigens under various culture conditions are assumed to produce bacterins that are more optimal than others.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

Unless expressly described to the contrary, each of the preferred features described herein can be used in combination with any and all of the other herein described preferred features.

Items

1. A method for producing a bacterial vaccine composition against a bacterial disease in an animal, such as a tetrapod and/or a fish, wherein said bacterial vaccine composition comprises inactivated bacteria of the bacterium causing said bacterial disease, said method comprising preparing one or more of cultures A to H by:
    i) preparing a culture A by first preparing a pre-culture a. by inoculating said bacterium in 0.5 to 3.5%, such as 0.9% NaCl, and incubating before transferring said pre-culture a. to a nutrient-rich bacterial growth medium, such as Luria broth with 0.5% to 3.5%, such as 0.9% NaCl, and incubating under microaerophilic conditions to prepare culture A;
    ii) preparing a culture B by first preparing a pre-culture a. by inoculating said bacterium in 0.5 to 3.5%, such as 0.9% NaCl and incubating before transferring said pre-culture a. to cell culture medium for fish or mammalian cells, such as RPMI medium 1640, DMEM+GlutaMAX®, AIM-V+AlbuMAx®, or Leibowitz medium, and incubating under microaerophilic conditions to prepare culture B;
    iii) preparing a culture C by first preparing a pre-culture b. by inoculating said bacterium in a cell culture medium for fish or mammalian cells, such as RPMI medium 1640, DMEM+GlutaMAX, AIM-V+AlbuMAx, or Leibowitz medium, and incubating before transferring said pre-culture b. to a solution typically comprising about 0.5 to 15% (w/v) gelatin, such as 3.2% (w/v), with 0.05 to 1.5% glucose, such as 1% glucose, such as in a ratio of ¼ of culture b. to the gelatin/glucose solution and incubating under microaerophilic conditions to prepare culture C;
    iv) preparing a culture D by first preparing a pre-culture c. by inoculating said bacterium in blood, plasma or serum, e.g. from horses, and incubating before transferring said pre-culture c. to brain heart infusion medium with 0.05 to 1.5% glucose, such as 1% glucose, such as in a ratio of ¼ of culture c. to brain heart infusion medium and incubating under microaerophilic conditions to prepare culture D;
    v) preparing a culture E by inoculation said bacterium in enrichment broth and incubating under aerobic conditions to prepare culture E;

vi) preparing a culture F by transferring bacteria from culture E or from enrichment medium containing for example blood, plasma and/or serum to 0.5 to 3.5% NaCl, such as 0.9% NaCl;

vii) preparing a culture G by transferring bacteria from culture E or from enrichment medium containing for example blood, plasma and/or serum, to a cell culture medium for fish or mammalian cells, such as RPMI medium 1640, DMEM+GlutaMAX, AIM-V+ AlbuMAX, or Leibowitz medium;

viii) preparing a culture H by transferring bacteria from culture E or from enrichment medium containing for example blood, plasma and/or serum to blood or plasma serum, e.g. from horses;

ix) inactivating the bacteria of cultures A-H;

x) optionally washing the inactivated cultures of step ix), such as in phosphate buffered saline (PBS); and xi) if more than one culture is prepared, mixing the optionally washed and resuspended inactivated cultures to prepare the bacterial vaccine composition;
wherein step xi) of mixing optionally may be performed before step ix) or before step x) instead of after step x);
with the proviso that if culture E is prepared, then at least one of cultures A-D or F-H is also prepared.

2. The method according to item 1, wherein step ix) is performed directly following step viii).

3. The method according to item 1 or 2, wherein said bacterial disease is a co-infection.

4. The method according to items 1-3, wherein said method comprises preparing two or more of the cultures A-H.

5. The method according to items 1-4, wherein said method comprises preparing three or more of the cultures A-H, such as three, four, five, six, seven, or eight of the cultures A-H.

6. The method according to any one of any one of the preceding items, wherein one of the cultures is culture A.

7. The method according to any one of any one of the preceding items, wherein one of the cultures is culture D.

8. The method according to any one of any one of the preceding items, wherein one of the cultures is culture B.

9. The method according to any one of any one of the preceding items, wherein one of the cultures is culture C.

10. The method according to any one of any one of the preceding items, wherein one of the cultures is culture E and at least one of cultures A-D or F-H.

11. The method according to any one of any one of the preceding items, wherein one of the cultures is culture F.

12. The method according to any one of any one of the preceding items, wherein one of the cultures is culture G.

13. The method according to any one of any one of the preceding items, wherein one of the cultures is culture H.

14. The method according to any one of any one of the preceding items, wherein said method comprises preparing all of cultures A-H.

15. The method according to any one of items 1-5, wherein the cultures of the bacterial vaccine composition comprises or consist of cultures E, F, and H.

16. The method according to any one of items 1-5, wherein the cultures of the bacterial vaccine composition comprises or consist of cultures A, B, C, G, and H.

17. The method according to any one of items 1-5, wherein the cultures of the bacterial vaccine composition comprises or consist of cultures B, C, E, G, and H.

18. The method according to any one of items 1-5, wherein the cultures of the bacterial vaccine composition comprises or consist of cultures A, B, C, F, and G.

19. The method according to any one of items 1-5, wherein the cultures of the bacterial vaccine composition comprises or consist of cultures A, B, C, E, and H.

20. The method according to any one of items 1-5, wherein the cultures of the bacterial vaccine composition comprises or consist of cultures B, C, E, G, and H.

21. The method according to any one of items 1-5, wherein the cultures of the bacterial vaccine composition comprises or consist of cultures A, B, D, E, G, and H.

22. The method according to any one of items 1-5, wherein the cultures of the bacterial vaccine composition comprises or consist of cultures A, B, C, D, and G.

23. The method according to item 14, wherein the ratio of cultures A-H is:

| Culture | Relative % |
|---------|------------|
| A | 8.6% |
| B | 8.6% |
| C | 8.6% |
| D | 8.6% |
| E | 40% |
| F | 8.6% |
| G | 8.6% |
| H | 8.6% |

24. The method according to item 14, wherein the ratio of cultures A-H is

| Culture | Relative % |
|---------|------------|
| A | 10% |
| B | 10% |
| C | 10% |
| D | 15% |
| E | 40% |
| F | 5% |
| G | 5% |
| H | 6% |

25. The method according to any one of the preceding items, wherein said cell-culture medium for fish or mammalian cell is Leibowitz medium.

26. The method according to any one of the preceding items, wherein the method is followed by mixing the bacterial vaccine composition obtained in said method with an adjuvant.

27. The method according to item 18, wherein said adjuvant is a mixture of Freunds Incomplete Adjuvant (FICA) and Curdlan.

28. The method according to item 27, wherein said FICA and Curdlan are present in a ratio of 40% to 60%, 50% to 50% or 60% to 40%.

29. The method according to any one of the preceding items, wherein said bacterium is selected from the group consisting of *Staphylococcus pseudintermedius, Aeromonas salmonicida, Tenacibaculum dicentrarchi, Moritella viscosa, Aliivibrio wodanis. Vibrio anguil-*

*larum, Aliivibrio salmonicida, Aliivibrio friggiae, Bizionia piscinecroseptica, Aliivibrio hodis, Aliivibrio heliae, Photobacterium pisciinfectiosa, Staphylococcus aureus, Streptococcus equi.*

30. The method according to any one of the preceding items, wherein said mammal is a tetrapod, such as a mammal, bird or amphibia alike.

31. The method according to item 30, wherein said mammal is a dog, a cat, a horse, a cow, a sheep, a goat, a pig, or a human.

32. The method according to item 30, wherein said bird is a chicken, a hen or a turkey.

33. The method according to any one of items 1-29, wherein said fish is a teleost, such as salmon, sea bass, or trout.

34. A bacterial vaccine composition obtainable or obtained by the method according to any one of the preceding items.

35. A bacterial vaccine composition according to item 34 for use in the treatment and/or prevention of a bacterial disease caused by said bacterium in said bacterial vaccine composition.

36. The bacterial vaccine composition for use according to item 35, wherein said bacterial disease an infection caused by *Staphylococcus pseudintermedius*, such as a skin infection, such s deep furunculosis or superficial impetigo and/or ear infection.

37. The bacterial vaccine composition for use according to item 35, wherein said bacterial disease is winter ulcer, ulcer rot, fin rot, vibriosis, cold-water vibriosis and/or furunculosis.

38. The bacterial vaccine composition for use according to any one of items 35-37, wherein said bacterial vaccine composition is administered via bath vaccination, dip vaccination, intraperitoneally, subcutaneously, topically and/or by oral vaccination.

39. Use of a bacterial vaccine composition according to item 34 for the manufacture of a vaccine for the treatment and/or prevention of bacterial diseases caused by said bacterium in said bacterial vaccine composition.

40. The use according to item 39, wherein said bacterial disease an infection caused by *Staphylococcus pseudintermedius*, such as a skin infection, such as deep furunculosis or superficial impetigo and/or ear infection.

41. The use according to item 39, wherein said bacterial disease is winter ulcer, ulcer rot, fin rot, vibriosis, cold-water vibriosis and/or furunculosis.

42. The use according to any one of items 39-41, wherein said bacterial vaccine composition is administered via bath vaccination, dip vaccination, intraperitoneally, subcutaneously, topically and/or by oral vaccination 43. A method for treating or preventing a bacterial infection, said method comprising administering a pharmaceutically effective amount of a bacterial vaccine composition according to item 34 to a subject in need thereof.

44. The method according to item 43, wherein said bacterial disease an infection caused by *Staphylococcus pseudintermedius*, such as a skin infection, such s deep furunculosis or superficial impetigo and/or ear infection.

45. The method according to item 43, wherein said bacterial disease is winter ulcer, ulcer rot, fin rot, vibriosis, cold-water vibriosis and/or furunculosis.

46. The method according to any one of items 43-45, wherein said bacterial vaccine composition is administered via bath vaccination, dip vaccination, intraperitoneally, subcutaneously, topically and/or by oral vaccination.

The invention claimed is:

1. A method for producing a bacterial vaccine composition against a bacterial disease in a tetrapod and/or a fish, wherein said bacterial vaccine composition comprises inactivated bacteria of the bacterium causing said bacterial disease, said method comprising:
   i) preparing cultures A, B, C, D, F, G and H, or preparing all of cultures A to H, wherein:
      culture A is prepared by first preparing a pre-culture "a" by inoculating said bacterium in 0.5 to 3.5% NaCl, and incubating before transferring said pre-culture "a" to a nutrient-rich bacterial growth medium with 0.5% to 3.5% NaCl, and incubating under microaerophilic conditions to prepare culture A;
      culture B is prepared by first preparing a pre-culture "a" by inoculating said bacterium in 0.5 to 3.5% NaCl and incubating before transferring said pre-culture "a" to cell culture medium for fish or mammalian cells, and incubating under microaerophilic conditions to prepare culture B;
      culture C is prepared by first preparing a pre-culture "b" by inoculating said bacterium in a cell culture medium for fish or mammalian cells, and incubating before transferring said pre-culture "b" to a solution typically comprising about 0.5 to 15% (w/v) gelatin with 0.05 to 1.5% glucose and incubating under microaerophilic conditions to prepare culture C;
      culture D is prepared by first preparing a pre-culture "c" by inoculating said bacterium in blood, plasma or serum and incubating before transferring said pre-culture "c" to brain heart infusion medium with 0.05 to 1.5% glucose and incubating under microaerophilic conditions to prepare culture D;
      culture E is prepared by inoculating said bacterium in enrichment broth and incubating under aerobic conditions to prepare culture E;
      culture F is prepared by transferring bacteria from culture E or from enrichment medium containing for example blood, plasma and/or serum to 0.5 to 3.5% NaCl;
      culture G is prepared by transferring bacteria from culture E or from enrichment medium containing for example blood, plasma and/or serum, to a cell culture medium for fish or mammalian cells;
      culture H is prepared by transferring bacteria from culture E or from enrichment medium containing for example blood, plasma and/or serum to blood or plasma serum;
   ii) inactivating the bacteria of the prepared cultures;
   iii) optionally washing the inactivated cultures of step ii); and
   iv) mixing the optionally washed and resuspended inactivated cultures to prepare the bacterial vaccine composition;
      wherein step iv) of mixing optionally may be performed before step ii) or before step iii) instead of after step iii).

2. The method according to claim 1, wherein step ii) is performed directly following step i).

3. The method according to claim 1, wherein said bacterial disease is a co-infection.

4. The method according to claim 1, wherein the ratio of cultures A-H is:

| Culture | Relative % |
| --- | --- |
| A | 8.6% |
| B | 8.6% |
| C | 8.6% |
| D | 8.6% |
| E | 40% |
| F | 8.6% |
| G | 8.6% |
| H | 8.6%. |

5. The method according to claim 1, wherein the ratio of cultures A-H is

| Culture | Relative % |
| --- | --- |
| A | 10% |
| B | 10% |
| C | 10% |
| D | 15% |
| E | 40% |
| F | 5% |
| G | 5% |
| H | 5%. |

6. The method according to claim 1, wherein said cell-culture medium for fish or mammalian cell is Leibowitz medium.

7. The method according to claim 1, wherein the method is followed by mixing the bacterial vaccine composition obtained in said method with an adjuvant.

8. The method according to claim 7, wherein said adjuvant is a mixture of Freunds Incomplete Adjuvant (FICA) and Curdlan.

9. The method according to claim 1, wherein said bacterium is selected from the group consisting of *Staphylococcus pseudintermedius, Aeromonas salmonicida, Tenacibaculum dicentrarchi, Moritella viscosa, Aliivibrio wodanis, Vibrio anguillarum, Aliivibrio salmonicida, Aliivibrio friggiae, Bizionia piscinecroseptica, Aliivibrio hodis, Aliivibrio heliae, Photobacterium pisciinfectiosa, Staphylococcus aureus*, and *Streptococcus equi*.

10. The method according to claim 1, wherein said tetrapod is a mammal, bird or amphibia.

11. The method according to claim 1, wherein said fish is a teleost.

12. A bacterial vaccine composition obtainable or obtained by the method according to claim 1.

13. The method according to claim 1, wherein:
in the preparation of culture A, the nutrient-rich bacterial growth medium with 0.5% to 3.5% NaCl is Luria broth with 0.5% to 3.5% NaCl;
in the preparation of culture B, the cell culture medium for fish or mammalian cells is RPMI medium 1640 or Leibowitz medium;
in the preparation of culture C, the cell culture medium for fish or mammalian cells is RPMI medium 1640 or Leibowitz medium;
in the preparation of culture C, the 0.5 to 15% (w/v) gelatin is 3.2% (w/v) gelatin;
in the preparation of culture C, the 0.05 to 1.5% glucose is 1% glucose;
in the preparation of culture C, the pre-culture "b" is transferred to the gelatin/glucose solution in a ratio of ¼ of culture "b" to the gelatin/glucose solution;
in the preparation of culture D, the 0.05 to 1.5% glucose is 1% glucose;
in the preparation of culture D, the pre-culture "c" is transferred to the brain heart infusion medium in a ratio of ¼ of culture "c" to the brain heart infusion medium;
in the preparation of culture F, the 0.5 to 3.5% NaCl is 0.9% NaCl; and/or
in the preparation of culture G, the cell culture medium for fish or mammalian cells is RPMI medium 1640 or Leibowitz medium.

14. The method according to claim 8, wherein said FICA and Curdlan are present in a ratio of 40% to 60%, 50% to 50% or 60% to 40%.

15. The method according to claim 10, wherein said mammal is a dog, a cat, a horse, a cow, a sheep, a goat, a pig, or a human; or wherein said bird is a chicken, a hen or a turkey.

16. The method according to claim 11, wherein said teleost is salmon, sea bass, or trout.

* * * * *